US012376845B2

(12) United States Patent
Roorda et al.

(10) Patent No.: US 12,376,845 B2
(45) Date of Patent: Aug. 5, 2025

(54) SYSTEMS, METHODS, AND DEVICES FOR CLOSING HOLES IN BODY LUMENS

(71) Applicant: Abbott Cardiovascular Systems, Inc., Santa Clara, CA (US)

(72) Inventors: Wouter E. Roorda, Palo Alto, CA (US); Douglas H. Mehl, Redwood City, CA (US); Rizza A. Garcia, Newark, CA (US); Timothy C. Reynolds, Sunnyvale, CA (US); Dinorah V. Merrill, Modesto, CA (US); Dawn Ma, San Jose, CA (US); David J. Milazzo, Santa Clara, CA (US); Aaron M. Fortson, Fremont, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 18/498,282

(22) Filed: Oct. 31, 2023

(65) Prior Publication Data
US 2024/0057995 A1 Feb. 22, 2024

Related U.S. Application Data

(60) Continuation of application No. 17/130,764, filed on Dec. 22, 2020, now Pat. No. 11,839,351, which is a
(Continued)

(51) Int. Cl.
*A61B 17/04* (2006.01)
*A61B 17/06* (2006.01)
*A61B 17/00* (2006.01)

(52) U.S. Cl.
CPC .... *A61B 17/0469* (2013.01); *A61B 17/06061* (2013.01); *A61B 2017/00637* (2013.01);
(Continued)

(58) Field of Classification Search
CPC .. A61B 2017/00663; A61B 2017/0472; A61B 17/0057; A61B 17/0469;
(Continued)

(56) References Cited

U.S. PATENT DOCUMENTS

| 312,408 A | 2/1885 | Wackerhagen |
| 597,165 A | 1/1898 | Hall |

(Continued)

FOREIGN PATENT DOCUMENTS

| DE | 0912619 C | 5/1954 |
| DE | 9217932 U1 | 6/1993 |

(Continued)

OTHER PUBLICATIONS

Notice of Allowance received for U.S. Pat. No. 6,206,893 mailed on Oct. 25, 2000.
(Continued)

*Primary Examiner* — Katherine M Shi
(74) *Attorney, Agent, or Firm* — Workman Nydegger

(57) ABSTRACT

A device for closing an opening in a body lumen, the device having a first elongate member with a first lumen, a second elongate member distal the first elongate member, and a needle assembly slidably cooperating with the first elongate member to position a plurality of sutures within the lumen of the first elongate member. The needle assembly includes a needle base and a plurality of needle portions extending from the needle base. Slidable movement of the needle assembly in relation to the first elongate member locates the plurality of sutures selectively mounted to the needle assembly within the first lumen.

17 Claims, 28 Drawing Sheets

Related U.S. Application Data continuation of application No. 16/052,263, filed on Aug. 1, 2018, now Pat. No. 10,980,531, which is a continuation of application No. 15/005,880, filed on Jan. 25, 2016, now Pat. No. 10,111,653, which is a division of application No. 13/485,388, filed on May 31, 2012, now Pat. No. 9,241,707.

(52) U.S. Cl.
CPC .............. *A61B 2017/00663* (2013.01); *A61B 2017/00778* (2013.01); *A61B 2017/0472* (2013.01); *A61B 17/0485* (2013.01)

(58) Field of Classification Search
CPC ...... A61B 17/0482; A61B 2017/00637; A61B 2017/0496; A61B 2017/00672; A61B 17/0483
See application file for complete search history.

(56) References Cited

U.S. PATENT DOCUMENTS

| | | |
|---|---|---|
| 659,422 A | 10/1900 | Shilder |
| 989,231 A | 4/1911 | Chamberlain |
| 989,234 A | 4/1911 | Davis |
| 1,574,362 A | 2/1926 | Callahan |
| 1,625,602 A | 4/1927 | Gould et al. |
| 1,940,351 A | 12/1933 | Howard |
| 2,012,776 A | 8/1935 | Hans |
| 2,108,206 A | 2/1938 | Mecker |
| 2,127,903 A | 8/1938 | Bowen |
| 2,131,321 A | 9/1938 | Hart |
| 2,371,978 A | 3/1945 | Perham |
| 2,397,823 A | 4/1946 | Walter |
| RE22,857 E | 3/1947 | Ogbrurn |
| 2,588,589 A | 3/1952 | Tauber |
| 2,595,086 A | 4/1952 | Larzelere |
| 2,610,631 A | 9/1952 | Calicchio |
| 2,646,045 A | 7/1953 | Priestley |
| 2,692,599 A | 10/1954 | Creelman |
| 2,941,489 A | 6/1960 | Fischbein |
| 2,959,172 A | 11/1960 | Held |
| 3,033,156 A | 5/1962 | Verbish |
| 3,104,666 A | 9/1963 | Hale et al. |
| 3,197,102 A | 7/1965 | Bernice et al. |
| 3,359,983 A | 12/1967 | Elmore |
| 3,413,397 A | 11/1968 | Bierbaum et al. |
| 3,422,181 A | 1/1969 | Chirgwin, Jr. |
| 3,470,875 A | 10/1969 | Johnson |
| 3,485,234 A | 12/1969 | Stevens |
| 3,587,115 A | 6/1971 | Shiley |
| 3,630,205 A | 12/1971 | Listner |
| 3,653,388 A | 4/1972 | Tenckhoff |
| 3,665,926 A | 5/1972 | Flores |
| 3,776,237 A | 12/1973 | Hill et al. |
| 3,802,438 A | 4/1974 | Wolvek |
| 3,814,104 A | 6/1974 | Irnich et al. |
| 3,820,544 A | 6/1974 | Semm |
| 3,840,017 A | 10/1974 | Molante |
| 3,874,388 A | 4/1975 | King et al. |
| 3,878,848 A | 4/1975 | Hiebert |
| 3,908,662 A | 9/1975 | Razgulov et al. |
| 3,918,455 A | 11/1975 | Coplan |
| 3,926,194 A | 12/1975 | Greenberg et al. |
| 3,939,820 A | 2/1976 | Grayzel |
| 3,985,138 A | 10/1976 | Jarvik |
| 4,011,872 A | 3/1977 | Komiya |
| 4,018,228 A | 4/1977 | Goosen |
| 4,069,825 A | 1/1978 | Akiyama |
| 4,109,658 A | 8/1978 | Hughes |
| 4,128,100 A | 12/1978 | Wendorff |
| 4,135,623 A | 1/1979 | Thyen |
| 4,161,951 A | 7/1979 | Scanlan, Jr. |
| 4,168,073 A | 9/1979 | Larue |
| 4,182,339 A | 1/1980 | Hardy, Jr. |
| 4,185,636 A | 1/1980 | Frater et al. |
| 4,216,776 A | 8/1980 | Downie et al. |
| 4,217,665 A | 8/1980 | Bex et al. |
| 4,235,177 A | 11/1980 | Arbuckle |
| 4,235,238 A | 11/1980 | Ogiu et al. |
| 4,316,469 A | 2/1982 | Kapitanov |
| 4,317,445 A | 3/1982 | Robinson |
| 4,411,654 A | 10/1983 | Boarini et al. |
| 4,412,832 A | 11/1983 | Kling et al. |
| 4,437,465 A | 3/1984 | Nomoto et al. |
| 4,469,101 A | 9/1984 | Coleman et al. |
| 4,492,229 A | 1/1985 | Grunwald |
| 4,493,323 A | 1/1985 | Albright et al. |
| 4,501,276 A | 2/1985 | Lombardi |
| 4,553,543 A | 11/1985 | Amarasinghe |
| 4,554,543 A | 11/1985 | Wyatt et al. |
| 4,580,566 A | 4/1986 | Hsu |
| 4,586,614 A | 5/1986 | Ger |
| 4,587,969 A | 5/1986 | Gillis |
| 4,596,559 A | 6/1986 | Fleischhacker |
| 4,610,248 A | 9/1986 | Rosenberg |
| 4,629,450 A | 12/1986 | Suzuki et al. |
| 4,651,733 A | 3/1987 | Mobin-Uddin |
| 4,655,211 A | 4/1987 | Sakamoto et al. |
| 4,702,250 A | 10/1987 | Ovil et al. |
| 4,723,549 A | 2/1988 | Wholey et al. |
| 4,738,666 A | 4/1988 | Fuqua |
| 4,744,364 A | 5/1988 | Kensey |
| 4,748,982 A | 6/1988 | Horzewski et al. |
| 4,782,954 A | 11/1988 | Reynolds |
| 4,803,984 A | 2/1989 | Narayanan et al. |
| 4,823,794 A | 4/1989 | Pierce |
| 4,830,002 A | 5/1989 | Semm |
| 4,836,205 A | 6/1989 | Barrett |
| 4,845,851 A | 7/1989 | Warthen |
| 4,848,341 A | 7/1989 | Ahmad |
| 4,852,568 A | 8/1989 | Kensey |
| 4,890,612 A | 1/1990 | Kensey |
| 4,898,155 A | 2/1990 | Ovil et al. |
| 4,911,164 A | 3/1990 | Roth |
| 4,917,089 A | 4/1990 | Sideris |
| 4,926,860 A | 5/1990 | Stice et al. |
| 4,929,246 A | 5/1990 | Sinofsky |
| 4,935,027 A | 6/1990 | Yoon |
| 4,950,285 A | 8/1990 | Wilk |
| 4,957,498 A | 9/1990 | Caspari et al. |
| 4,966,600 A | 10/1990 | Songer et al. |
| 4,981,149 A | 1/1991 | Yoon et al. |
| 4,983,168 A | 1/1991 | Moorehead |
| 4,984,581 A | 1/1991 | Stice |
| 5,002,563 A | 3/1991 | Pyka et al. |
| 5,009,643 A | 4/1991 | Reich et al. |
| 5,021,059 A | 6/1991 | Kensey et al. |
| 5,037,433 A | 8/1991 | Wilk et al. |
| 5,041,129 A | 8/1991 | Hayhurst et al. |
| 5,047,039 A | 9/1991 | Avant et al. |
| 5,059,201 A | 10/1991 | Asnis |
| 5,061,274 A | 10/1991 | Kensey |
| 5,074,874 A | 12/1991 | Yoon et al. |
| 5,078,721 A | 1/1992 | McKeating |
| 5,080,664 A | 1/1992 | Jain |
| 5,089,010 A | 2/1992 | Korthoff |
| 5,100,419 A | 3/1992 | Ehlers |
| 5,100,422 A | 3/1992 | Berguer et al. |
| 5,100,432 A | 3/1992 | Matsutani |
| 5,108,421 A | 4/1992 | Fowler |
| 5,109,780 A | 5/1992 | Slouf et al. |
| 5,129,882 A | 7/1992 | Weldon et al. |
| 5,129,912 A | 7/1992 | Noda et al. |
| 5,129,913 A | 7/1992 | Ruppert |
| 5,144,961 A | 9/1992 | Chen et al. |
| 5,147,373 A | 9/1992 | Ferzli |
| 5,156,788 A | 10/1992 | Chesterfield et al. |
| 5,160,339 A | 11/1992 | Chen et al. |
| 5,163,946 A | 11/1992 | Li |
| 5,169,041 A | 12/1992 | Tan |
| 5,171,251 A | 12/1992 | Bregen et al. |
| 5,176,691 A | 1/1993 | Pierce |

(56) References Cited

U.S. PATENT DOCUMENTS

| | | |
|---|---|---|
| 5,178,629 A | 1/1993 | Kammerer |
| 5,192,287 A | 3/1993 | Fournier et al. |
| 5,192,294 A | 3/1993 | Blake, III |
| 5,192,301 A | 3/1993 | Kamiya et al. |
| 5,192,302 A | 3/1993 | Kensey et al. |
| 5,201,744 A | 4/1993 | Jones |
| 5,207,703 A | 5/1993 | Jain |
| 5,211,650 A | 5/1993 | Noda |
| 5,217,470 A | 6/1993 | Weston |
| 5,217,471 A | 6/1993 | Burkhart |
| 5,217,485 A | 6/1993 | Liu et al. |
| 5,219,358 A | 6/1993 | Bendel et al. |
| 5,222,974 A | 6/1993 | Kensey et al. |
| 5,234,443 A | 8/1993 | Phan et al. |
| 5,234,445 A | 8/1993 | Walker et al. |
| 5,237,985 A | 8/1993 | Hodgson et al. |
| 5,237,996 A | 8/1993 | Waldman et al. |
| 5,242,427 A | 9/1993 | Bilweis |
| 5,250,033 A | 10/1993 | Evans et al. |
| 5,250,053 A | 10/1993 | Snyder |
| 5,250,054 A | 10/1993 | Li |
| 5,254,105 A | 10/1993 | Haaga |
| 5,254,113 A | 10/1993 | Wilk |
| 5,254,126 A | 10/1993 | Filipi et al. |
| 5,258,003 A | 11/1993 | Ciaglia et al. |
| 5,259,846 A | 11/1993 | Granger et al. |
| 5,275,616 A | 1/1994 | Fowler |
| 5,279,311 A | 1/1994 | Snyder |
| 5,281,236 A | 1/1994 | Bagnato et al. |
| 5,281,237 A | 1/1994 | Gimpelson |
| 5,284,485 A | 2/1994 | Kammerer et al. |
| 5,285,945 A | 2/1994 | Brinkerhoff et al. |
| 5,289,963 A | 3/1994 | McGarry et al. |
| 5,290,284 A | 3/1994 | Adair |
| 5,290,297 A | 3/1994 | Phillips |
| 5,290,310 A | 3/1994 | Makower et al. |
| 5,292,309 A | 3/1994 | Van et al. |
| 5,292,327 A | 3/1994 | Dodd et al. |
| 5,292,332 A | 3/1994 | Lee |
| 5,293,881 A | 3/1994 | Green et al. |
| 5,295,993 A | 3/1994 | Green |
| 5,300,085 A | 4/1994 | Yock |
| 5,304,184 A | 4/1994 | Hathaway et al. |
| 5,304,185 A | 4/1994 | Taylor |
| 5,306,254 A | 4/1994 | Nash et al. |
| 5,312,024 A | 5/1994 | Grant et al. |
| 5,312,423 A | 5/1994 | Rosenbluth et al. |
| 5,318,578 A | 6/1994 | Hasson |
| 5,320,629 A | 6/1994 | Noda et al. |
| 5,320,632 A | 6/1994 | Heidmueller |
| 5,330,445 A | 7/1994 | Haaga |
| 5,330,491 A | 7/1994 | Walker et al. |
| 5,334,217 A | 8/1994 | Das |
| 5,336,229 A | 8/1994 | Noda |
| 5,336,230 A | 8/1994 | Leichtling et al. |
| 5,336,231 A | 8/1994 | Adair |
| 5,342,369 A | 8/1994 | Harryman, II |
| 5,353,974 A | 10/1994 | Maurizio |
| 5,354,279 A | 10/1994 | Berthold |
| 5,354,312 A | 10/1994 | Brinkerhoff et al. |
| 5,364,407 A | 11/1994 | Poll |
| 5,364,408 A | 11/1994 | Gordon |
| 5,368,595 A | 11/1994 | Lewis |
| 5,368,601 A | 11/1994 | Sauer et al. |
| 5,374,275 A | 12/1994 | Bradley et al. |
| 5,374,278 A | 12/1994 | Chesterfield et al. |
| 5,376,096 A | 12/1994 | Foster |
| 5,383,896 A | 1/1995 | Gershony et al. |
| 5,383,905 A | 1/1995 | Golds et al. |
| 5,385,569 A | 1/1995 | Swor |
| 5,387,221 A | 2/1995 | Bisgaard |
| 5,387,227 A | 2/1995 | Grice |
| 5,391,176 A | 2/1995 | De La Torre |
| 5,391,182 A | 2/1995 | Chin |
| 5,395,332 A | 3/1995 | Ressemann et al. |
| 5,395,349 A | 3/1995 | Quiachon et al. |
| 5,397,310 A | 3/1995 | Chu et al. |
| 5,397,325 A | 3/1995 | Della et al. |
| 5,397,326 A | 3/1995 | Mangum |
| 5,403,329 A | 4/1995 | Hinchcliffe |
| 5,403,330 A | 4/1995 | Tuason |
| 5,403,331 A | 4/1995 | Chesterfield et al. |
| 5,403,338 A | 4/1995 | Milo |
| 5,405,352 A | 4/1995 | Weston |
| 5,411,481 A | 5/1995 | Allen et al. |
| 5,413,571 A | 5/1995 | Katsaros et al. |
| 5,417,684 A | 5/1995 | Jackson et al. |
| 5,417,699 A | 5/1995 | Klein et al. |
| 5,419,765 A | 5/1995 | Weldon et al. |
| 5,425,705 A | 6/1995 | Evard et al. |
| 5,425,737 A | 6/1995 | Burbank et al. |
| 5,425,740 A | 6/1995 | Hutchinson, Jr. |
| 5,431,666 A | 7/1995 | Sauer et al. |
| 5,433,700 A | 7/1995 | Peters |
| 5,452,733 A | 9/1995 | Sterman et al. |
| 5,454,822 A | 10/1995 | Schoeb et al. |
| 5,454,834 A | 10/1995 | Boebel et al. |
| 5,458,574 A | 10/1995 | Machold et al. |
| 5,458,609 A | 10/1995 | Gordon et al. |
| 5,462,560 A | 10/1995 | Stevens |
| 5,462,561 A | 10/1995 | Voda |
| 5,464,426 A | 11/1995 | Bonutti |
| 5,466,241 A | 11/1995 | Leroy et al. |
| 5,470,338 A | 11/1995 | Whitfield et al. |
| 5,474,568 A | 12/1995 | Scott |
| 5,476,469 A | 12/1995 | Hathaway et al. |
| 5,476,470 A | 12/1995 | Fitzgibbons, Jr. |
| 5,478,309 A | 12/1995 | Sweezer et al. |
| 5,478,353 A | 12/1995 | Yoon |
| 5,478,354 A | 12/1995 | Tovey et al. |
| 5,480,407 A | 1/1996 | Wan et al. |
| 5,486,190 A | 1/1996 | Green |
| 5,489,295 A | 2/1996 | Piplani et al. |
| 5,492,119 A | 2/1996 | Abrams |
| 5,496,332 A | 3/1996 | Sierra et al. |
| 5,507,744 A | 4/1996 | Tay et al. |
| 5,507,755 A | 4/1996 | Gresl et al. |
| 5,507,757 A | 4/1996 | Sauer et al. |
| 5,507,758 A | 4/1996 | Thomason et al. |
| 5,509,902 A | 4/1996 | Raulerson |
| 5,520,655 A | 5/1996 | Davila et al. |
| 5,520,665 A | 5/1996 | Fleetwood |
| 5,520,691 A | 5/1996 | Branch |
| 5,520,702 A | 5/1996 | Sauer et al. |
| 5,527,321 A | 6/1996 | Hinchliffe |
| 5,527,322 A | 6/1996 | Klein et al. |
| D372,310 S | 7/1996 | Hartnett |
| 5,531,700 A | 7/1996 | Moore et al. |
| 5,536,267 A | 7/1996 | Edwards et al. |
| 5,536,273 A | 7/1996 | Lehrer |
| 5,540,701 A | 7/1996 | Sharkey et al. |
| 5,540,703 A | 7/1996 | Barker et al. |
| 5,540,704 A | 7/1996 | Gordon et al. |
| 5,545,171 A | 8/1996 | Sharkey et al. |
| 5,545,178 A | 8/1996 | Kensey et al. |
| 5,545,180 A | 8/1996 | Le et al. |
| 5,549,618 A | 8/1996 | Fleenor et al. |
| 5,549,631 A | 8/1996 | Bonutti |
| 5,554,162 A | 9/1996 | Delange |
| 5,562,684 A | 10/1996 | Kammerer |
| 5,562,686 A | 10/1996 | Sauer et al. |
| 5,562,688 A | 10/1996 | Riza |
| 5,562,728 A | 10/1996 | Lazarus et al. |
| 5,567,435 A | 10/1996 | Hubbell et al. |
| 5,569,269 A | 10/1996 | Hart et al. |
| 5,569,271 A | 10/1996 | Hoel |
| 5,571,120 A | 11/1996 | Yoon |
| 5,573,540 A | 11/1996 | Yoon |
| 5,578,044 A | 11/1996 | Gordon et al. |
| 5,584,842 A | 12/1996 | Fogarty et al. |
| 5,591,177 A | 1/1997 | Lehrer |
| 5,591,179 A | 1/1997 | Edelstein |
| 5,591,206 A | 1/1997 | Moufarrege |
| 5,593,421 A | 1/1997 | Bauer |

(56) References Cited

U.S. PATENT DOCUMENTS

| | | |
|---|---|---|
| 5,601,572 A | 2/1997 | Middleman et al. |
| 5,603,718 A | 2/1997 | Xu |
| 5,607,435 A | 3/1997 | Sachdeva et al. |
| 5,609,597 A | 3/1997 | Lehrer |
| 5,611,794 A | 3/1997 | Sauer et al. |
| 5,613,974 A | 3/1997 | Andreas et al. |
| 5,613,975 A | 3/1997 | Christy |
| 5,624,446 A | 4/1997 | Harryman, II |
| 5,626,588 A | 5/1997 | Sauer et al. |
| 5,632,752 A | 5/1997 | Buelna |
| 5,643,289 A | 7/1997 | Sauer et al. |
| 5,643,295 A | 7/1997 | Yoon |
| 5,643,318 A | 7/1997 | Tsukernik et al. |
| 5,647,372 A | 7/1997 | Tovey et al. |
| 5,649,959 A | 7/1997 | Hannam et al. |
| 5,653,717 A | 8/1997 | Ko et al. |
| 5,662,664 A | 9/1997 | Gordon et al. |
| 5,669,917 A | 9/1997 | Sauer et al. |
| 5,672,174 A | 9/1997 | Gough et al. |
| 5,674,231 A | 10/1997 | Green et al. |
| 5,676,689 A | 10/1997 | Kensey et al. |
| 5,693,061 A | 12/1997 | Pierce et al. |
| 5,700,273 A | 12/1997 | Buelna et al. |
| 5,707,379 A | 1/1998 | Fleenor et al. |
| 5,713,899 A | 2/1998 | Marnay et al. |
| 5,713,910 A | 2/1998 | Gordon et al. |
| 5,716,369 A | 2/1998 | Riza |
| 5,720,574 A | 2/1998 | Barella |
| 5,720,757 A | 2/1998 | Hathaway et al. |
| 5,722,981 A | 3/1998 | Stevens |
| 5,725,552 A | 3/1998 | Kotula et al. |
| 5,728,109 A | 3/1998 | Schulze et al. |
| 5,728,114 A | 3/1998 | Evans et al. |
| 5,728,133 A | 3/1998 | Kontos |
| 5,728,143 A | 3/1998 | Gough et al. |
| 5,728,151 A | 3/1998 | Garrison et al. |
| 5,741,276 A | 4/1998 | Poloyko et al. |
| 5,741,280 A | 4/1998 | Fleenor |
| 5,746,755 A | 5/1998 | Wood et al. |
| 5,749,890 A | 5/1998 | Shaknovich |
| 5,755,727 A | 5/1998 | Kontos |
| 5,759,188 A | 6/1998 | Yoon |
| 5,759,189 A | 6/1998 | Ferragamo et al. |
| 5,766,183 A | 6/1998 | Sauer |
| 5,766,186 A | 6/1998 | Faraz et al. |
| 5,766,217 A | 6/1998 | Christy |
| 5,769,862 A | 6/1998 | Kammerer et al. |
| 5,779,719 A | 7/1998 | Klein et al. |
| 5,782,860 A | 7/1998 | Epstein et al. |
| 5,782,861 A | 7/1998 | Cragg et al. |
| 5,792,151 A | 8/1998 | Heck et al. |
| 5,792,152 A | 8/1998 | Klein et al. |
| 5,797,928 A | 8/1998 | Kogasaka |
| 5,797,929 A | 8/1998 | Andreas et al. |
| 5,799,661 A | 9/1998 | Boyd et al. |
| 5,810,849 A | 9/1998 | Kontos |
| 5,810,850 A | 9/1998 | Hathaway et al. |
| 5,810,884 A | 9/1998 | Kim |
| 5,814,069 A | 9/1998 | Schulze et al. |
| 5,817,113 A | 10/1998 | Gifford et al. |
| 5,820,631 A | 10/1998 | Nobles |
| 5,824,010 A | 10/1998 | McDonald |
| 5,824,111 A | 10/1998 | Schall et al. |
| 5,830,125 A | 11/1998 | Scribner et al. |
| 5,836,315 A | 11/1998 | Benderev et al. |
| 5,836,955 A | 11/1998 | Buelna et al. |
| 5,836,956 A | 11/1998 | Buelna et al. |
| 5,846,253 A | 12/1998 | Buelna et al. |
| 5,848,714 A | 12/1998 | Robson et al. |
| 5,855,576 A | 1/1999 | Leveen et al. |
| 5,855,585 A | 1/1999 | Kontos |
| 5,860,963 A | 1/1999 | Azam et al. |
| 5,860,990 A | 1/1999 | Nobles et al. |
| 5,860,991 A | 1/1999 | Klein et al. |
| 5,861,005 A | 1/1999 | Kontos |
| 5,868,762 A | 2/1999 | Cragg et al. |
| 5,871,490 A | 2/1999 | Schulze et al. |
| 5,871,502 A | 2/1999 | Suryadevara |
| 5,873,876 A | 2/1999 | Christy |
| 5,876,411 A | 3/1999 | Kontos |
| 5,895,404 A | 4/1999 | Ruiz |
| 5,897,487 A | 4/1999 | Ouchi |
| 5,897,564 A | 4/1999 | Schulze et al. |
| 5,902,311 A | 5/1999 | Andreas et al. |
| 5,904,597 A | 5/1999 | Doi et al. |
| 5,904,690 A | 5/1999 | Middleman et al. |
| 5,904,697 A | 5/1999 | Gifford et al. |
| 5,906,631 A | 5/1999 | Imran |
| 5,919,207 A | 7/1999 | Taheri |
| 5,921,994 A | 7/1999 | Andreas et al. |
| 5,928,266 A | 7/1999 | Kontos |
| 5,951,547 A | 9/1999 | Gough et al. |
| 5,951,590 A | 9/1999 | Goldfarb |
| 5,954,732 A | 9/1999 | Hart et al. |
| 5,957,936 A | 9/1999 | Yoon et al. |
| 5,957,937 A | 9/1999 | Yoon |
| 5,957,938 A | 9/1999 | Zhu et al. |
| 5,964,773 A | 10/1999 | Greenstein |
| 5,964,782 A | 10/1999 | Lafontaine et al. |
| 5,972,030 A | 10/1999 | Garrison et al. |
| 5,976,161 A | 11/1999 | Kirsch et al. |
| 5,980,517 A | 11/1999 | Gough |
| 5,980,539 A | 11/1999 | Kontos |
| 5,993,466 A | 11/1999 | Yoon |
| 5,993,476 A | 11/1999 | Groiso |
| 5,997,555 A | 12/1999 | Kontos |
| 6,001,109 A | 12/1999 | Kontos |
| 6,009,877 A | 1/2000 | Edwards |
| 6,022,372 A | 2/2000 | Kontos |
| 6,024,747 A | 2/2000 | Kontos |
| 6,036,699 A | 3/2000 | Andreas et al. |
| 6,042,601 A | 3/2000 | Smith |
| 6,048,351 A | 4/2000 | Gordon et al. |
| 6,048,354 A | 4/2000 | Lawrence |
| 6,048,357 A | 4/2000 | Kontos |
| 6,056,744 A | 5/2000 | Edwards |
| 6,059,800 A | 5/2000 | Hart et al. |
| 6,068,603 A | 5/2000 | Suzuki |
| 6,077,276 A | 6/2000 | Kontos |
| 6,077,279 A | 6/2000 | Kontos |
| 6,083,242 A | 7/2000 | Cook |
| 6,102,920 A | 8/2000 | Sullivan et al. |
| 6,117,144 A | 9/2000 | Nobles et al. |
| 6,117,145 A | 9/2000 | Wood et al. |
| 6,126,675 A | 10/2000 | Shchervinsky et al. |
| 6,132,439 A | 10/2000 | Kontos |
| 6,132,440 A | 10/2000 | Hathaway et al. |
| 6,136,010 A | 10/2000 | Modesitt et al. |
| 6,139,556 A | 10/2000 | Kontos |
| 6,143,004 A | 11/2000 | Davis et al. |
| 6,152,936 A | 11/2000 | Christy et al. |
| 6,165,183 A | 12/2000 | Kuehn et al. |
| 6,165,204 A | 12/2000 | Levinson et al. |
| 6,190,396 B1 | 2/2001 | Whitin et al. |
| 6,197,042 B1 | 3/2001 | Ginn et al. |
| 6,206,893 B1 | 3/2001 | Klein et al. |
| 6,206,895 B1 | 3/2001 | Levinson |
| 6,221,084 B1 | 4/2001 | Fleenor |
| 6,245,079 B1 | 6/2001 | Nobles et al. |
| 6,248,124 B1 | 6/2001 | Pedros et al. |
| 6,296,657 B1 | 10/2001 | Brucker |
| 6,302,870 B1 | 10/2001 | Jacobsen et al. |
| 6,306,081 B1 | 10/2001 | Ishikawa et al. |
| 6,322,580 B1 | 11/2001 | Kanner |
| 6,346,111 B1 | 2/2002 | Gordon et al. |
| 6,348,059 B1 | 2/2002 | Hathaway et al. |
| 6,355,050 B1 | 3/2002 | Andreas et al. |
| 6,358,258 B1 | 3/2002 | Arcia et al. |
| 6,395,015 B1 | 5/2002 | Borst et al. |
| 6,397,110 B1 | 5/2002 | Kuzma |
| 6,428,472 B1 | 8/2002 | Haas |
| 6,428,549 B1 | 8/2002 | Kontos |
| 6,436,109 B1 | 8/2002 | Kontos |
| 6,443,963 B1 | 9/2002 | Baldwin et al. |

(56) References Cited

U.S. PATENT DOCUMENTS

| | | |
|---|---|---|
| 6,451,031 B1 | 9/2002 | Kontos |
| 6,461,366 B1 | 10/2002 | Seguin |
| 6,464,707 B1 | 10/2002 | Bjerken |
| 6,511,489 B2 | 1/2003 | Field et al. |
| 6,517,498 B1 | 2/2003 | Burbank et al. |
| 6,517,553 B2 | 2/2003 | Klein et al. |
| 6,533,812 B2 | 3/2003 | Swanson et al. |
| 6,551,329 B1 | 4/2003 | Sater |
| 6,551,330 B1 | 4/2003 | Bain et al. |
| 6,558,399 B1 | 5/2003 | Isbell et al. |
| 6,562,052 B2 | 5/2003 | Nobles et al. |
| 6,569,159 B1 | 5/2003 | Edwards et al. |
| 6,569,185 B2 | 5/2003 | Ungs |
| 6,572,629 B2 | 6/2003 | Kalloo et al. |
| 6,610,072 B1 | 8/2003 | Christy et al. |
| 6,623,509 B2 | 9/2003 | Ginn |
| 6,623,510 B2 | 9/2003 | Carley et al. |
| 6,626,930 B1 | 9/2003 | Allen et al. |
| 6,632,237 B2 | 10/2003 | Ben-David et al. |
| 6,641,592 B1 | 11/2003 | Sauer et al. |
| 6,663,655 B2 | 12/2003 | Ginn et al. |
| 6,676,685 B2 | 1/2004 | Pedros et al. |
| 6,689,051 B2 | 2/2004 | Nakada et al. |
| 6,695,867 B2 | 2/2004 | Ginn et al. |
| 6,716,228 B2 | 4/2004 | Tal |
| 6,743,195 B2 | 6/2004 | Zucker |
| 6,743,241 B2 | 6/2004 | Kerr |
| 6,743,259 B2 | 6/2004 | Ginn |
| 6,745,079 B2 | 6/2004 | King |
| 6,746,457 B2 | 6/2004 | Dana et al. |
| 6,749,621 B2 | 6/2004 | Pantages et al. |
| 6,749,622 B2 | 6/2004 | McGuckin et al. |
| 6,767,356 B2 | 7/2004 | Kanner et al. |
| 6,776,784 B2 | 8/2004 | Ginn |
| 6,776,785 B1 | 8/2004 | Yencho et al. |
| 6,837,906 B2 | 1/2005 | Ginn |
| 6,846,319 B2 | 1/2005 | Ginn et al. |
| 6,890,343 B2 | 5/2005 | Ginn et al. |
| 6,896,692 B2 | 5/2005 | Ginn et al. |
| 6,911,034 B2 * | 6/2005 | Nobles ............... A61B 17/0057 606/147 |
| 6,936,054 B2 | 8/2005 | Chu |
| 6,939,357 B2 | 9/2005 | Navarro et al. |
| 6,955,643 B2 | 10/2005 | Gellman et al. |
| 6,964,668 B2 | 11/2005 | Modesitt et al. |
| 6,969,371 B2 | 11/2005 | Palasis et al. |
| 6,969,397 B2 | 11/2005 | Ginn |
| 6,997,932 B2 | 2/2006 | Dreyfuss et al. |
| 7,001,400 B1 | 2/2006 | Modesitt et al. |
| 7,029,480 B2 | 4/2006 | Klein et al. |
| 7,029,481 B1 | 4/2006 | Burdulis et al. |
| 7,033,370 B2 | 4/2006 | Gordon et al. |
| 7,048,747 B2 | 5/2006 | Arcia et al. |
| 7,060,084 B1 | 6/2006 | Loshakove et al. |
| 7,063,661 B2 | 6/2006 | Okada |
| 7,063,710 B2 | 6/2006 | Takamoto et al. |
| 7,063,711 B1 | 6/2006 | Loshakove et al. |
| 7,066,077 B2 | 6/2006 | Schnapp et al. |
| 7,083,635 B2 | 8/2006 | Ginn |
| 7,108,710 B2 | 9/2006 | Anderson |
| 7,112,225 B2 | 9/2006 | Ginn |
| 7,122,002 B2 | 10/2006 | Okada |
| 7,131,980 B1 | 11/2006 | Field et al. |
| 7,147,646 B2 | 12/2006 | Dana et al. |
| 7,160,309 B2 | 1/2007 | Voss |
| 7,179,266 B2 | 2/2007 | Kontos |
| 7,229,458 B2 | 6/2007 | Boecker et al. |
| 7,235,087 B2 | 6/2007 | Modesitt et al. |
| 7,270,672 B1 | 9/2007 | Singer |
| 7,316,704 B2 | 1/2008 | Bagaoisan et al. |
| 7,326,230 B2 | 2/2008 | Ravikumar |
| 7,331,979 B2 | 2/2008 | Khosravi et al. |
| 7,335,220 B2 | 2/2008 | Khosravi et al. |
| 7,361,183 B2 | 4/2008 | Ginn |
| 7,361,185 B2 | 4/2008 | O'Malley et al. |
| 7,377,927 B2 | 5/2008 | Burdulis et al. |
| 7,390,328 B2 | 6/2008 | Modesitt |
| 7,393,363 B2 | 7/2008 | Ginn |
| 7,431,727 B2 | 10/2008 | Cole et al. |
| 7,442,198 B2 | 10/2008 | Gellman et al. |
| 7,445,626 B2 | 11/2008 | Songer et al. |
| 7,449,024 B2 | 11/2008 | Stafford |
| 7,462,188 B2 | 12/2008 | Mcintosh |
| 7,507,200 B2 | 3/2009 | Okada |
| 7,727,249 B2 | 6/2010 | Rahmani |
| 7,731,655 B2 | 6/2010 | Smith et al. |
| 7,749,249 B2 | 7/2010 | Gelbart et al. |
| 7,753,923 B2 | 7/2010 | St et al. |
| 7,833,235 B2 | 11/2010 | Chu |
| 7,837,696 B2 | 11/2010 | Modesitt et al. |
| 7,842,047 B2 | 11/2010 | Modesitt et al. |
| 7,842,048 B2 | 11/2010 | Ma |
| 7,842,049 B2 | 11/2010 | Voss |
| 7,846,170 B2 | 12/2010 | Modesitt et al. |
| 7,850,701 B2 | 12/2010 | Modesitt et al. |
| 7,883,517 B2 | 2/2011 | Pantages et al. |
| 7,935,128 B2 | 5/2011 | Rioux et al. |
| 7,967,832 B2 | 6/2011 | Chu |
| 8,038,688 B2 | 10/2011 | Modesitt et al. |
| 8,048,092 B2 | 11/2011 | Modesitt et al. |
| 8,057,491 B2 | 11/2011 | Modesitt et al. |
| 8,083,754 B2 | 12/2011 | Pantages et al. |
| 8,123,762 B2 | 2/2012 | Chu et al. |
| 8,137,364 B2 | 3/2012 | Zung et al. |
| 8,172,860 B2 | 5/2012 | Zung et al. |
| 8,202,281 B2 | 6/2012 | Voss |
| 8,211,122 B2 | 7/2012 | McIntosh |
| 8,252,008 B2 | 8/2012 | Ma |
| 8,257,368 B2 | 9/2012 | McIntosh |
| 8,267,947 B2 | 9/2012 | Pantages et al. |
| 8,313,498 B2 | 11/2012 | Pantages et al. |
| 8,323,298 B2 | 12/2012 | Modesitt et al. |
| 8,361,088 B2 | 1/2013 | McIntosh |
| 8,419,753 B2 | 4/2013 | Stafford |
| 8,430,893 B2 | 4/2013 | Ma |
| 8,512,375 B2 | 8/2013 | Torrie et al. |
| 8,574,244 B2 | 11/2013 | Reynolds |
| 8,597,309 B2 | 12/2013 | Stafford |
| 8,663,248 B2 | 3/2014 | Zung et al. |
| 8,663,252 B2 | 3/2014 | Fortson |
| 8,858,573 B2 | 10/2014 | Fortson et al. |
| 8,864,778 B2 | 10/2014 | Fortson et al. |
| 8,998,932 B2 | 4/2015 | Voss |
| 9,155,535 B2 | 10/2015 | McIntosh |
| 9,241,707 B2 | 1/2016 | Roorda et al. |
| 9,282,960 B2 | 3/2016 | Ma |
| 9,301,747 B2 | 4/2016 | Zung et al. |
| 9,370,353 B2 | 6/2016 | Fortson et al. |
| 9,375,211 B2 | 6/2016 | Stafford |
| 9,592,038 B2 | 3/2017 | Pantages et al. |
| 9,820,730 B2 | 11/2017 | Chu |
| 9,889,276 B2 | 2/2018 | Voss |
| 9,993,237 B2 | 6/2018 | Ma |
| 10,111,653 B2 | 10/2018 | Roorda et al. |
| 10,245,022 B2 | 4/2019 | Mcintosh |
| 10,413,288 B2 | 9/2019 | Stafford |
| 10,426,449 B2 | 10/2019 | Fortson |
| 10,426,499 B2 | 10/2019 | Owen et al. |
| 10,463,353 B2 | 11/2019 | Fortson et al. |
| 2001/0046518 A1 | 11/2001 | Sawhney |
| 2002/0045908 A1 * | 4/2002 | Nobles ............... A61B 17/0057 606/144 |
| 2002/0049453 A1 | 4/2002 | Nobles et al. |
| 2002/0095164 A1 | 7/2002 | Andreas et al. |
| 2002/0099389 A1 | 7/2002 | Michler et al. |
| 2002/0106409 A1 | 8/2002 | Sawhney et al. |
| 2002/0107531 A1 | 8/2002 | Schreck et al. |
| 2002/0177876 A1 | 11/2002 | Roby et al. |
| 2002/0188275 A1 | 12/2002 | McGuckin |
| 2003/0093093 A1 | 5/2003 | Modesitt et al. |
| 2003/0167063 A1 | 9/2003 | Kerr |
| 2003/0171764 A1 | 9/2003 | Debbas |
| 2003/0195529 A1 | 10/2003 | Takamoto et al. |
| 2003/0233095 A1 | 12/2003 | Urbanski et al. |

(56) References Cited

U.S. PATENT DOCUMENTS

| | | |
|---|---|---|
| 2004/0009205 A1 | 1/2004 | Sawhney |
| 2004/0021025 A1 | 2/2004 | Shiga et al. |
| 2004/0068273 A1* | 4/2004 | Fariss ............... A61B 17/0625 606/144 |
| 2004/0092964 A1 | 5/2004 | Modesitt et al. |
| 2004/0093027 A1 | 5/2004 | Fabisiak et al. |
| 2004/0097978 A1 | 5/2004 | Modesitt et al. |
| 2004/0122449 A1 | 6/2004 | Modesitt et al. |
| 2004/0127940 A1 | 7/2004 | Ginn et al. |
| 2004/0143290 A1 | 7/2004 | Brightbill |
| 2004/0158127 A1 | 8/2004 | Okada |
| 2004/0158287 A1 | 8/2004 | Cragg et al. |
| 2004/0167511 A1 | 8/2004 | Buehlmann et al. |
| 2004/0181238 A1 | 9/2004 | Zarbatany et al. |
| 2004/0186487 A1 | 9/2004 | Klein et al. |
| 2004/0191277 A1 | 9/2004 | Sawhney et al. |
| 2004/0210251 A1 | 10/2004 | Kontos |
| 2004/0215232 A1 | 10/2004 | Belhe et al. |
| 2004/0225301 A1 | 11/2004 | Roop et al. |
| 2004/0267193 A1 | 12/2004 | Bagaoisan et al. |
| 2004/0267308 A1 | 12/2004 | Bagaoisan et al. |
| 2005/0059982 A1* | 3/2005 | Zung ............... A61B 17/0467 606/144 |
| 2005/0070923 A1 | 3/2005 | McIntosh |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0121042 A1 | 6/2005 | Belhe et al. |
| 2005/0143761 A1 | 6/2005 | Modesitt et al. |
| 2005/0149065 A1 | 7/2005 | Modesitt |
| 2005/0149066 A1 | 7/2005 | Stafford |
| 2005/0149117 A1 | 7/2005 | Khosravi et al. |
| 2005/0171561 A1 | 8/2005 | Songer et al. |
| 2005/0177189 A1 | 8/2005 | Ginn et al. |
| 2005/0222614 A1 | 10/2005 | Ginn et al. |
| 2005/0245876 A1 | 11/2005 | Khosravi et al. |
| 2005/0267528 A1 | 12/2005 | Ginn et al. |
| 2005/0273137 A1 | 12/2005 | Ginn |
| 2006/0034930 A1 | 2/2006 | Khosravi et al. |
| 2006/0047313 A1 | 3/2006 | Khanna et al. |
| 2006/0069397 A1 | 3/2006 | Nobles et al. |
| 2006/0079914 A1 | 4/2006 | Modesitt et al. |
| 2006/0089635 A1 | 4/2006 | Young et al. |
| 2006/0095029 A1 | 5/2006 | Young et al. |
| 2006/0100664 A1 | 5/2006 | Pai et al. |
| 2006/0142785 A1 | 6/2006 | Modesitt et al. |
| 2006/0167476 A1 | 7/2006 | Burdulis et al. |
| 2006/0167477 A1 | 7/2006 | Arcia et al. |
| 2006/0173469 A1 | 8/2006 | Klein et al. |
| 2006/0253037 A1 | 11/2006 | Ginn et al. |
| 2006/0253072 A1 | 11/2006 | Pai et al. |
| 2006/0259049 A1 | 11/2006 | Harada et al. |
| 2007/0005079 A1 | 1/2007 | Zarbatany et al. |
| 2007/0032798 A1 | 2/2007 | Pantages et al. |
| 2007/0032799 A1 | 2/2007 | Pantages et al. |
| 2007/0032801 A1 | 2/2007 | Pantages et al. |
| 2007/0049967 A1 | 3/2007 | Sibbitt et al. |
| 2007/0049968 A1 | 3/2007 | Sibbitt et al. |
| 2007/0060895 A1 | 3/2007 | Sibbitt et al. |
| 2007/0060950 A1 | 3/2007 | Khosravi et al. |
| 2007/0112304 A1 | 5/2007 | Voss |
| 2007/0123817 A1 | 5/2007 | Khosravi et al. |
| 2007/0167959 A1 | 7/2007 | Modesitt et al. |
| 2007/0203506 A1 | 8/2007 | Sibbitt et al. |
| 2007/0276410 A1 | 11/2007 | McIntosh |
| 2007/0282354 A1 | 12/2007 | McIntosh |
| 2008/0009794 A1 | 1/2008 | Bagaoisan et al. |
| 2008/0045979 A1 | 2/2008 | Ma |
| 2008/0065151 A1 | 3/2008 | Ginn |
| 2008/0065152 A1 | 3/2008 | Carley |
| 2008/0287967 A1 | 11/2008 | Andreas et al. |
| 2008/0319458 A1 | 12/2008 | Reynolds |
| 2009/0005793 A1 | 1/2009 | Pantages et al. |
| 2009/0036906 A1 | 2/2009 | Stafford |
| 2009/0048615 A1 | 2/2009 | McIntosh |
| 2009/0088779 A1 | 4/2009 | Zung et al. |
| 2009/0157105 A1 | 6/2009 | Zung et al. |
| 2009/0254119 A1 | 10/2009 | Sibbitt et al. |
| 2010/0030242 A1 | 2/2010 | Nobles et al. |
| 2010/0130965 A1 | 5/2010 | Sibbitt et al. |
| 2010/0179572 A1 | 7/2010 | Voss et al. |
| 2011/0066184 A1 | 3/2011 | Modesitt et al. |
| 2011/0071472 A1 | 3/2011 | Voss |
| 2011/0071552 A1 | 3/2011 | Ma |
| 2011/0071567 A1 | 3/2011 | Modesitt et al. |
| 2011/0077670 A1 | 3/2011 | Modesitt et al. |
| 2011/0190793 A1 | 8/2011 | Nobles et al. |
| 2011/0196387 A1 | 8/2011 | Pantages et al. |
| 2011/0196393 A1 | 8/2011 | Eliachar et al. |
| 2011/0270282 A1 | 11/2011 | Lemke |
| 2011/0288563 A1 | 11/2011 | Gianotti et al. |
| 2012/0016383 A1 | 1/2012 | Sauer et al. |
| 2012/0053600 A1* | 3/2012 | Fortson ............... A61B 17/0057 606/145 |
| 2012/0150201 A1 | 6/2012 | Pantages et al. |
| 2012/0283749 A1 | 11/2012 | Sauer |
| 2012/0289903 A1 | 11/2012 | Voss |
| 2012/0316579 A1 | 12/2012 | Ma |
| 2013/0006277 A1 | 1/2013 | Stafford |
| 2013/0012962 A1* | 1/2013 | Stone ............... A61B 17/0469 606/144 |
| 2013/0066340 A1 | 3/2013 | Pantages et al. |
| 2013/0138122 A1 | 5/2013 | McIntosh |
| 2013/0190781 A1 | 7/2013 | Fortson et al. |
| 2013/0237999 A1 | 9/2013 | Ma |
| 2013/0267966 A1 | 10/2013 | Fortson et al. |
| 2013/0267967 A1 | 10/2013 | Fortson et al. |
| 2013/0325058 A1 | 12/2013 | Roorda et al. |
| 2014/0180312 A1 | 6/2014 | Zung et al. |
| 2014/0222032 A1 | 8/2014 | Stafford |
| 2014/0236189 A1 | 8/2014 | Melsheimer et al. |
| 2015/0025551 A1 | 1/2015 | Fortson et al. |
| 2015/0119906 A1 | 4/2015 | Bagaoisan et al. |
| 2015/0273186 A1 | 10/2015 | Voss |
| 2016/0135803 A1 | 5/2016 | Mcintosh |
| 2016/0135805 A1 | 5/2016 | Roorda et al. |
| 2016/0192914 A1 | 7/2016 | Ma |
| 2016/0287229 A1 | 10/2016 | Zung et al. |
| 2016/0367234 A1 | 12/2016 | Fortson et al. |
| 2016/0367241 A1 | 12/2016 | Stafford |
| 2018/0228478 A1 | 8/2018 | Fortson |
| 2018/0338759 A1 | 11/2018 | Roorda et al. |
| 2019/0175168 A1 | 6/2019 | McIntosh |
| 2019/0261964 A1 | 8/2019 | Zung et al. |
| 2019/0357900 A1 | 11/2019 | Stafford |
| 2020/0060664 A1 | 2/2020 | Fortson et al. |

FOREIGN PATENT DOCUMENTS

| | | |
|---|---|---|
| DE | 4210724 C1 | 7/1993 |
| DE | 4219724 A1 | 12/1993 |
| DE | 4220283 A1 | 12/1993 |
| DE | 10211360 A1 | 10/2003 |
| EP | 0140557 A2 | 5/1985 |
| EP | 0140757 A2 | 5/1985 |
| EP | 0207545 A1 | 1/1987 |
| EP | 0474887 A1 | 3/1992 |
| EP | 0478358 A1 | 4/1992 |
| EP | 0478887 A1 | 4/1992 |
| EP | 0542126 A2 | 5/1993 |
| EP | 0543499 A1 | 5/1993 |
| EP | 0568098 A2 | 11/1993 |
| EP | 0589409 A1 | 3/1994 |
| EP | 0624343 A2 | 11/1994 |
| EP | 0669101 A1 | 8/1995 |
| EP | 0669103 A1 | 8/1995 |
| EP | 0684012 A2 | 11/1995 |
| EP | 0812571 A1 | 12/1997 |
| EP | 0669102 B1 | 10/1998 |
| EP | 0941698 A1 | 9/1999 |
| EP | 0910288 B1 | 8/2002 |
| EP | 1407557 A1 | 4/2004 |
| FR | 1059544 A | 3/1954 |

(56) References Cited

FOREIGN PATENT DOCUMENTS

| | | | |
|---|---|---|---|
| FR | 2768324 A1 | 3/1999 |
| JP | 51-143386 U | 11/1976 |
| JP | 52-020794 A | 2/1977 |
| JP | 02-119866 | 5/1990 |
| JP | 05-042161 | 2/1993 |
| JP | 05-220794 A | 8/1993 |
| SU | 820810 A1 | 4/1981 |
| SU | 0993922 A1 | 2/1983 |
| SU | 1093329 A1 | 5/1984 |
| SU | 1174036 A1 | 8/1985 |
| SU | 1544383 A1 | 2/1990 |
| SU | 1648400 A1 | 5/1991 |
| WO | 85/03858 A1 | 9/1985 |
| WO | 94/05213 A1 | 3/1994 |
| WO | 94/13211 A1 | 6/1994 |
| WO | 94/27503 A1 | 12/1994 |
| WO | 94/28801 A1 | 12/1994 |
| WO | 95/05121 A1 | 2/1995 |
| WO | 95/13021 A1 | 5/1995 |
| WO | 95/25468 A1 | 9/1995 |
| WO | 95/35065 A1 | 12/1995 |
| WO | 96/09006 A2 | 3/1996 |
| WO | 97/00046 A1 | 1/1997 |
| WO | 97/01790 A1 | 1/1997 |
| WO | 97/03613 A1 | 2/1997 |
| WO | 97/07745 A1 | 3/1997 |
| WO | 97/10764 A1 | 3/1997 |
| WO | 97/13461 A1 | 4/1997 |
| WO | 97/17901 A1 | 5/1997 |
| WO | 97/20505 A1 | 6/1997 |
| WO | 97/27897 A1 | 8/1997 |
| WO | 98/04195 A1 | 2/1998 |
| WO | 98/42262 A1 | 10/1998 |
| WO | 99/47049 A1 | 9/1999 |
| WO | 00/12013 A1 | 3/2000 |
| WO | 00/51498 A1 | 9/2000 |
| WO | 00/69342 A2 | 11/2000 |
| WO | 01/19259 A1 | 3/2001 |
| WO | 01/35833 A1 | 5/2001 |
| WO | 02/36021 A2 | 5/2002 |
| WO | 02/62234 A2 | 8/2002 |
| WO | 03/03598 | 1/2003 |
| WO | 03/03925 | 1/2003 |
| WO | 03/94748 A1 | 11/2003 |
| WO | 03/99134 A2 | 12/2003 |
| WO | 2005/000126 A2 | 1/2005 |
| WO | 2005/023119 A1 | 3/2005 |
| WO | 2005/025430 A1 | 3/2005 |
| WO | 2005/030060 A1 | 4/2005 |
| WO | 2005/041782 A2 | 5/2005 |
| WO | 2005/063129 A2 | 7/2005 |
| WO | 2005/065549 A1 | 7/2005 |
| WO | 2005/092204 A2 | 10/2005 |
| WO | 2005/112782 A1 | 12/2005 |
| WO | 2006/026116 A1 | 3/2006 |
| WO | 2006/052611 A1 | 5/2006 |
| WO | 2006/052612 A1 | 5/2006 |
| WO | 2006/078578 A2 | 7/2006 |
| WO | 2006/115901 A1 | 11/2006 |
| WO | 2006/115904 A2 | 11/2006 |
| WO | 2006/118877 A2 | 11/2006 |
| WO | 2007/019016 A1 | 2/2007 |
| WO | 2007/025014 A2 | 3/2007 |
| WO | 2007/025017 A2 | 3/2007 |
| WO | 2007/025018 A2 | 3/2007 |
| WO | 2007/025019 A2 | 3/2007 |
| WO | 2007/081836 A1 | 7/2007 |
| WO | 2010/031050 A1 | 3/2010 |

OTHER PUBLICATIONS

Notice of Allowance received for U.S. Pat. No. 6,355,050 mailed on Sep. 11, 2001.
Notice of Allowance received for U.S. Pat. No. 6,358,258 mailed on Apr. 20, 2001.
Notice of Allowance received for U.S. Pat. No. 6,358,258 mailed on Sep. 10, 2001.
Notice of Allowance received for U.S. Pat. No. 6,517,553 mailed on Sep. 9, 2002.
Notice of Allowance received for U.S. Pat. No. 6,558,399 mailed on Dec. 24, 2002.
Notice of Allowance received for U.S. Pat. No. 7,029,480 mailed on Nov. 17, 2005.
Notice of Allowance received for U.S. Pat. No. 7,029,481 mailed on Nov. 15, 2005.
Notice of Allowance received for U.S. Pat. No. 7,048,747 mailed on Dec. 13, 2005.
Notice of Allowance received for U.S. Pat. No. 5,792,152 mailed on Oct. 17, 1997.
Notice of Allowance, Feb. 22, 2007, 7,235,087.
Notice of intent received for U.S. Appl. No. 90/006,469, mailed on Sep. 27, 2005.
Notice of Re-Issue received for U.S. Appl. No. 90/006,469, mailed on Sep. 27, 2005.
Office Action received for U.S. Pat. No. 6,036,699, mailed on Sep. 14, 1998.
Office Action received for U.S. Appl. No. 13/333,411, mailed on Apr. 1, 2015.
Office Action received for U.S. Appl. No. 13/333,411, mailed on Apr. 4, 2016.
Office Action received for U.S. Appl. No. 13/485,388, mailed on May 21, 2015.
Office Action received for U.S. Appl. No. 13/752,095, mailed on Feb. 20, 2015.
Office Action received for U.S. Appl. No. 13/791,858, mailed on Nov. 10, 2015.
Office Action received for U.S. Appl. No. 13/870,628, mailed on Jul. 13, 2015.
Office Action received for U.S. Appl. No. 07/989,611, filed Aug. 1, 1994.
Office Action received for U.S. Appl. No. 07/989,611, mailed on Aug. 1, 1994.
Office Action received for U.S. Appl. No. 07/989,611, mailed on May 12, 1993.
Office Action received for U.S. Appl. No. 08/148,809, mailed on May 30, 1995.
Office Action received for U.S. Appl. No. 08/148,809, mailed on Oct. 26, 1995.
Office Action received for U.S. Appl. No. 08/148,809, mailed on Sep. 16, 1994.
Office Action received for U.S. Appl. No. 08/252,124, mailed on Jan. 5, 1996.
Office Action received for U.S. Appl. No. 08/252,124, mailed on Jun. 5, 1995.
Office Action received for U.S. Appl. No. 08/259,410, mailed on Feb. 2, 1995.
Office Action received for U.S. Appl. No. 08/259,410, mailed on Jun. 1, 1995.
Office Action received for U.S. Appl. No. 08/638,076, mailed on Jan. 21, 1997.
Office Action received for U.S. Appl. No. 08/824,031, mailed on Apr. 13, 1999.
Office Action received for U.S. Appl. No. 08/824,031, mailed on Mar. 16, 1998.
Office Action received for U.S. Appl. No. 08/824,031, mailed on Sep. 14, 1998.
Office Action received for U.S. Appl. No. 08/883,246, mailed on Apr. 12, 1999.
Office Action received for U.S. Appl. No. 08/883,246, mailed on Jul. 11, 2001.
Office Action received for U.S. Appl. No. 08/883,246, mailed on Jul. 23, 1998.
Office Action received for U.S. Appl. No. 08/883,246, mailed on Oct. 13, 1999.
Office Action received for U.S. Appl. No. 08/883,246, mailed on Oct. 23, 2000.

(56) References Cited

OTHER PUBLICATIONS

Office Action received for U.S. Appl. No. 09/057,108, mailed on Jul. 10, 2000.
Office action received for U.S. Appl. No. 09/262,402, mailed on Mar. 29, 2000.
Office Action received for U.S. Appl. No. 09/395,901, mailed on Jun. 27, 2000.
Office Action received for U.S. Appl. No. 09/395,901, mailed on Nov. 6, 2000.
Office Action received for U.S. Appl. No. 09/610,099, mailed on Jul. 11, 2002.
Office action received for U.S. Appl. No. 09/651,344, mailed on Feb. 28, 2003.
Office action received for U.S. Appl. No. 09/651,344, mailed on Nov. 7, 2003.
Office Action received for U.S. Appl. No. 09/707,746, mailed on Feb. 16, 2005.
Office Action received for U.S. Appl. No. 14/094,352, mailed on Dec. 15, 2014.
Office Action received for U.S. Appl. No. 14/094,352, mailed on Jul. 8, 2015.
Office Action received for U.S. Appl. No. 14/195,308, mailed on Aug. 11, 2015.
Office Action received for U.S. Appl. No. 14/195,308, mailed on Dec. 18, 2014.
Office Action received for U.S. Appl. No. 14/511,730, mailed on Apr. 6, 2020.
Office Action received for U.S. Appl. No. 14/511,730, mailed on Jan. 20, 2017.
Office Action received for U.S. Appl. No. 14/511,730, mailed on Jan. 25, 2019.
Office Action received for U.S. Appl. No. 14/511,730, mailed on Jul. 8, 2019.
Office Action received for U.S. Appl. No. 14/511,730, mailed on Jun. 11, 2018.
Office Action received for U.S. Appl. No. 14/511,730, mailed on Oct. 13, 2017.
Office Action received for U.S. Appl. No. 14/674,756, mailed on Jul. 6, 2017.
Office Action received for U.S. Appl. No. 14/674,756, mailed on Mar. 17, 2017.
Office Action received for U.S. Appl. No. 14/880,894, filed Aug. 6, 2018.
Office Action received for U.S. Appl. No. 14/880,894, mailed on Apr. 2, 2018.
Office Action received for U.S. Appl. No. 14/880,894, mailed on Aug. 6, 2018.
Office Action received for U.S. Appl. No. 14/880,894, mailed on Oct. 31, 2017.
Office Action received for U.S. Appl. No. 15/005,880, mailed on Apr. 10, 2018.
Office Action received for U.S. Appl. No. 15/005,880, mailed on Nov. 13, 2017.
Office Action received for U.S. Appl. No. 15/090,150, filed Dec. 12, 2018.
Office Action received for U.S. Appl. No. 15/090,150, mailed on Dec. 12, 2018.
Office Action received for U.S. Appl. No. 15/090,150, mailed on Dec. 31, 2019.
Office Action received for U.S. Appl. No. 15/090,150, mailed on Jul. 5, 2019.
Office Action received for U.S. Appl. No. 15/186,730, filed Sep. 5, 2018.
Office Action received for U.S. Appl. No. 15/186,730, mailed on Mar. 21, 2019.
Office Action received for U.S. Appl. No. 15/186,730, mailed on Sep. 5, 2018.
Office Action received for U.S. Appl. No. 15/192,481, mailed on Jan. 11, 2019.
Office Action received for U.S. Appl. No. 15/192,481, mailed on Jul. 20, 2018.
Office Action received for U.S. Appl. No. 16/052,263, mailed on Jun. 2, 2020.
Office Action received for U.S. Patent Application No. 2002/0095164 mailed on Sep. 30, 2003.
Office Action received for U.S. Patent Application No. 2004/0186487 mailed on Jul. 16, 2007.
Office Action received for U.S. Patent Application No. 2004/0186487 mailed on Sep. 5, 2006.
Office Action received for U.S. Patent Application No. 2005/0149065 mailed on Mar. 23, 2007.
Office Action received for U.S. Patent Application No. 2005/0171561 mailed on Feb. 16, 2006.
Office Action received for U.S. Patent Application No. 2005/0171561 mailed on Jun. 7, 2007.
Office Action received for U.S. Patent Application No. 2005/0171561 mailed on Nov. 2, 2005.
Office Action received for U.S. Patent Application No. 2005/0171561 mailed on Oct. 19, 2006.
Office Action received for U.S. Patent Application No. 2006/0167477 mailed on Sep. 7, 2007.
Office Action received for U.S. Pat. No. 5,417,699 mailed on Aug. 1, 1994.
Office Action received for U.S. Pat. No. 5,527,322 mailed on May 30, 1995.
Office Action received for U.S. Pat. No. 5,527,322 mailed on Sep. 16, 1994.
Office Action received for U.S. Pat. No. 5,613,974 mailed on Jan. 5, 1996.
Office Action received for U.S. Pat. No. 5,613,974 mailed on Jun. 5, 1995.
Office Action received for U.S. Pat. No. 5,779,719 mailed on Jun. 1, 1995.
Office Action received for U.S. Pat. No. 5,792, 152 mailed on Jan. 21, 1997.
Office Action received for U.S. Pat. No. 5417699, mailed on May 12, 1993.
Office Action received for U.S. Pat. No. 5,527,322, mailed on Oct. 26, 1995.
Office Action received for U.S. Pat. No. 6,036,699 mailed on Apr. 13, 1999.
Office Action received for U.S. Pat. No. 6,206,893 mailed on Jul. 10, 2000.
Office Action received for U.S. Pat. No. 6,355,050 mailed on Jul. 11, 2001.
Office Action received for U.S. Pat. No. 6,355,050 mailed on Jul. 23, 1998.
Office action received for U.S. Appl. No. 10/877,974, mailed on Jul. 9, 2008.
Office action received for U.S. Appl. No. 10/909,531, mailed on Apr. 4, 2007.
Office action received for U.S. Appl. No. 10/909,531, mailed on Dec. 26, 2007.
Office action received for U.S. Appl. No. 10/909,531, mailed on Feb. 9, 2009.
Office action received for U.S. Appl. No. 10/909,531, mailed on Jun. 13, 2008.
Office action received for U.S. Appl. No. 10/909,531, mailed on Sep. 16, 2009.
Office action received for U.S. Appl. No. 10/948,445, mailed on Jul. 11, 2007.
Office action received for U.S. Appl. No. 11/199,338, mailed on Apr. 23, 2008.
Office action received for U.S. Appl. No. 11/199,338, mailed on Dec. 28, 2007.
Office action received for U.S. Appl. No. 11/199,338, mailed on Jan. 6, 2009.
Office action received for U.S. Appl. No. 11/199,338, mailed on Jan. 25, 2007.
Office action received for U.S. Appl. No. 11/199,338, mailed on Oct. 5, 2007.

(56) References Cited

OTHER PUBLICATIONS

Office action received for U.S. Appl. No. 11/199,496, mailed on Apr. 1, 2009.
Office action received for U.S. Appl. No. 11/199,496, mailed on Apr. 23, 2010.
Office Action received for U.S. Appl. No. 11/199,496, mailed on Apr. 28, 2011.
Office action received for U.S. Appl. No. 11/199,496, mailed on Aug. 21, 2009.
Office Action received for U.S. Appl. No. 11/199,515, mailed on Aug. 20, 2008.
Office action received for U.S. Appl. No. 11/199,515, mailed on Jun. 10, 2009.
Office action received for U.S. Appl. No. 11/199,515, mailed on Nov. 13, 2008.
Office action received for U.S. Appl. No. 11/273,107, mailed on Apr. 9, 2009.
Office action received for U.S. Appl. No. 11/273,107, mailed on Jan. 18, 2008.
Office action received for U.S. Appl. No. 11/273,107, mailed on Jun. 2, 2010.
Office action received for U.S. Appl. No. 11/273,107, mailed on Jun. 14, 2007.
Office Action received for U.S. Appl. No. 11/273,107, mailed on Oct. 27, 2010.
Office action received for U.S. Appl. No. 11/273,107, mailed on Oct. 28, 2009.
Office action received for U.S. Appl. No. 11/273,107, mailed on Sep. 5, 2008.
Office action received for U.S. Appl. No. 11/316,775, mailed on Apr. 16, 2008.
Office action received for U.S. Appl. No. 11/316,775, mailed on Aug. 6, 2008.
Office action received for U.S. Appl. No. 11/363,005, mailed on Apr. 17, 2008.
Office action received for U.S. Appl. No. 11/363,005, mailed on Dec. 14, 2007.
Office action received for U.S. Appl. No. 11/363,005, mailed on Dec. 23, 2008.
Office action received for U.S. Appl. No. 11/363,005, mailed on Jun. 22, 2007.
Office Action received for U.S. Appl. No. 11/390,937, mailed on Sep. 7, 2007.
Office Action received for U.S. Appl. No. 11/391,951, filed Aug. 26, 2009.
Office Action received for U.S. Appl. No. 11/391,951, mailed on Aug. 26, 2009.
Office Action received for U.S. Appl. No. 11/391,951, mailed on Jan. 30, 2009.
Office action received for U.S. Appl. No. 11/391,951, mailed on Jun. 23, 2010.
Office Action received for U.S. Appl. No. 11/391,951, mailed on Oct. 28, 2008.
Office action received for U.S. Appl. No. 11/465,527, mailed on Feb. 3, 2010.
Office action received for U.S. Appl. No. 11/508,656, mailed on Aug. 30, 2010.
Office Action received for U.S. Appl. No. 11/508,656, mailed on Dec. 9, 2009.
Office action received for U.S. Appl. No. 11/508,656, mailed on Mar. 25, 2010.
Office action received for U.S. Appl. No. 11/508,662, mailed on Apr. 14, 2010.
Office action received for U.S. Appl. No. 11/508,715, mailed on Apr. 26, 2010.
Office Action received for U.S. Appl. No. 11/508,715, mailed on Jan. 6, 2010.
Office action received for U.S. Appl. No. 11/552,593, mailed on Aug. 21, 2008.
Office action received for U.S. Appl. No. 11/552,593, mailed on Feb. 5, 2009.
Office Action received for U.S. Appl. No. 11/688,722, mailed on Mar. 10, 2010.
Office action received for U.S. Appl. No. 11/891,358, mailed on Apr. 26, 2010.
Office Action received for U.S. Appl. No. 11/891,358, mailed on Aug. 31, 2011.
Office Action received for U.S. Pat. No. 6,355,050 mailed on Oct. 13, 1999.
Office Action received for U.S. Pat. No. 6,355,050 mailed on Oct. 23, 2000.
Office Action received for U.S. Pat. No. 6,358,258 mailed on Nov. 6, 2000.
Office Action received for U.S. Pat. No. 6,517,553 mailed on Jun. 17, 2002.
Office Action received for U.S. Pat. No. 6,517,553 mailed on Oct. 23, 2001.
Office Action received for U.S. Pat. No. 6,558,399 mailed on Jul. 11, 2002.
Office Action received for U.S. Pat. No. 7,029,480 mailed on Jun. 10, 2005.
Office Action received for U.S. Pat. No. 7,029,480 mailed on Mar. 17, 2005.
Office Action received for U.S. Pat. No. 7,029,481 mailed on Feb. 16, 2005.
Office Action received for U.S. Pat. No. 7,029,481 mailed on Jul. 7, 2005.
Office Action received for U.S. Pat. No. 7,048,747 mailed on Aug. 24, 2005.
Office Action received for U.S. Pat. No. 7,048,747 mailed on Feb. 28, 2005.
Office Action received for U.S. Pat. No. 7,048,747 mailed on May 25, 2005.
Office Action received for U.S. Pat. No. 7,048,747, mailed on Mar. 17, 2004.
Office Action received for U.S. Pat. No. 7,048,747, mailed on Nov. 8, 2005.
Office Action received for U.S. Appl. No. 90/006,469, mailed on Sep. 10, 2004.
Office Action, Aug. 9, 2006, 7,235,087.
Product Brochure "The Proven Solution to Endoscopic Suturing", Laurus Medical Corp., Irvine, CA (Oct. 1994).
Product Brochure, "SuperStitch—Closure Made Simple(Trademark)", Sutura, Inc. (2003).
Product Brochure, Laurus Medical Corporation, Irvine, CA "The Laurus In-Line Endoscopic Suturing Device" (Oct. 1994) 1 page.
Re-Examination Certification received for U.S. Appl. No. 90/006,469, mailed on Jun. 27, 2006.
Rema-Medizintechnik GmbH, Product Brochure entitled "REMA", 7 pages, 1992.
Rema-Medizintechnik, Gmbh, "Innovation Through Progress," Jan. 1992, pp. 1-8.
Request for Re-Examination received for U.S. Appl. No. 90/006,469, mailed on Nov. 29, 2002.
Restriction requirement received for U.S. Appl. No. 08/259,410, mailed on Feb. 2, 1995.
Restriction Requirement received for U.S. Appl. No. 08/824,031, mailed on Mar. 16, 1998.
Restriction Requirement received for U.S. Appl. No. 09/395,901, mailed on Jun. 27, 2000.
Restriction Requirement received for U.S. Appl. No. 10/357,984, mailed on Jan. 9, 2006.
Restriction Requirement received for U.S. Appl. No. 10/746,210, mailed on Apr. 5, 2007.
Restriction Requirement received for U.S. Appl. No. 10/948,445, mailed on Jul. 11, 2007.
Restriction Requirement received for U.S. Appl. No. 11/199,515, mailed on Aug. 20, 2008.
Restriction Requirement received for U.S. Appl. No. 11/391,951, mailed on Oct. 28, 2008.
Restriction Requirement received for U.S. Appl. No. 11/960,593, mailed on Sep. 14, 2010.

(56) References Cited

OTHER PUBLICATIONS

Restriction Requirement received for U.S. Appl. No. 12/257,127, mailed on Aug. 30, 2010.
Restriction Requirement received for U.S. Appl. No. 12/873,728, Sep. 11, 2012.
Restriction Requirement received for U.S. Appl. No. 12/873,728, mailed on Sep. 11, 2012.
Serruys, PW et al., A Comparision of Balloon-Expandable-Stent Implantaion With Balloon Angioplast in Patients With Coronary Artery Disease, New England Journal of Medicine, 331:489-495, 1994.
Taber's Cyclopedic Medical Dictionary, 18.sup.th Ed. 1997, pp. 747 and 1420.
U.S. Appl. filed Apr. 10, 2012, Fortson et al., U.S. Appl. No. 13/443,659.
U.S. Appl. filed Apr. 24, 2012, Fortson et al., U.S. Appl. No. 13/445,053.
Notice of Allowance received for U.S. Appl. No. 14/094,352, mailed on Mar. 22, 2016.
Notice of Allowance received for U.S. Appl. No. 14/195,308, mailed on Dec. 4, 2015.
Notice of Allowance received for U.S. Appl. No. 07/989,611, mailed on Nov. 3, 1994.
Notice of Allowance received for U.S. Appl. No. 08/148,809, mailed on Dec. 15, 1995.
Notice of Allowance received for U.S. Appl. No. 08/252,124, mailed on May 22, 1996.
Notice of Allowance received for U.S. Appl. No. 08/259,410, mailed on Feb. 6, 1998.
Notice of Allowance received for U.S. Appl. No. 08/638,076, mailed on Oct. 17, 1997.
Notice of Allowance received for U.S. Appl. No. 08/824,031, mailed on Jul. 15, 1999.
Notice of Allowance received for U.S. Appl. No. 08/883,246, mailed on Sep. 11, 2001.
Notice of Allowance received for U.S. Appl. No. 09/057,108, mailed on Oct. 25, 2000.
Notice of allowance received for U.S. Appl. No. 09/262,402, mailed on May 30, 2000.
Notice of Allowance received for U.S. Appl. No. 09/395,901, mailed on Apr. 20, 2001.
Notice of Allowance received for U.S. Appl. No. 09/395,901, mailed on Sep. 10, 2001.
Notice of Allowance received for U.S. Appl. No. 09/610,099, mailed on Dec. 24, 2002.
Notice of allowance received for U.S. Appl. No. 09/651,344, mailed on Apr. 20, 2004.
Notice of Allowance received for U.S. Appl. No. 09/707,746, mailed on Nov. 15, 2005.
Notice of Allowance received for U.S. Appl. No. 09/769,109, mailed on Sep. 9, 2002.
Notice of Allowance received for U.S. Appl. No. 09/988,541, mailed on Dec. 13, 2005.
Notice of allowance received for U.S. Appl. No. 10/152,272, mailed on May 13, 2005.
Notice of Allowance received for U.S. Appl. No. 10/335,065, mailed on Nov. 17, 2005.
Notice of allowance received for U.S. Appl. No. 10/335,147, mailed on Oct. 4, 2006.
Notice of allowance received for U.S. Appl. No. 10/652,182, mailed on Feb. 22, 2007.
Notice of Allowance received for U.S. Appl. No. 10/660,288, mailed on Sep. 30, 2011.
Notice of allowance received for U.S. Appl. No. 10/729,541, mailed on Jul. 12, 2010.
Notice of allowance received for U.S. Appl. No. 10/729,541, mailed on Mar. 25, 2010.
Notice of allowance received for U.S. Appl. No. 10/729,541, mailed on Nov. 16, 2009.
Notice of Allowance received for U.S. Appl. No. 10/737,668, mailed on Jun. 26, 2008.
Notice of Allowance received for U.S. Appl. No. 10/742,406, filed Jan. 11, 2008.
Notice of Allowance received for U.S. Appl. No. 10/742,406, filed Sep. 10, 2007.
Notice of Allowance received for U.S. Appl. No. 10/742,406, mailed on Jan. 11, 2008.
Notice of Allowance received for U.S. Appl. No. 10/742,406, mailed on Sep. 10, 2007.
Notice of Allowance received for U.S. Appl. No. 10/746,210, filed Jul. 9, 2008.
Notice of Allowance received for U.S. Appl. No. 10/746,210, mailed on Jul. 9, 2008.
Notice of allowance received for U.S. Appl. No. 10/909,531, mailed on Apr. 29, 2010.
Notice of allowance received for U.S. Appl. No. 10/909,531, mailed on Aug. 20, 2010.
Notice of Allowance received for U.S. Appl. No. 11/199,515, filed Apr. 2, 2010.
Notice of Allowance received for U.S. Appl. No. 11/199,496, mailed on Aug. 18, 2011.
Notice of Allowance received for U.S. Appl. No. 11/199,515, mailed on Apr. 2, 2010.
Notice of allowance received for U.S. Appl. No. 11/199,515, mailed on Aug. 2, 2010.
Notice of allowance received for U.S. Appl. No. 11/199,515, mailed on Dec. 24, 2009.
Notice of Allowance received for U.S. Appl. No. 11/273,107, mailed on Jun. 2, 2011.
Notice of allowance received for U.S. Appl. No. 11/363,005, mailed on Jan. 14, 2010.
Notice of allowance received for U.S. Appl. No. 11/363,005, mailed on Jul. 10, 2009.
Notice of allowance received for U.S. Appl. No. 11/363,005, mailed on Jul. 23, 2010.
Notice of Allowance received for U.S. Appl. No. 11/389,762, mailed on Nov. 23, 2007.
Notice of Allowance received for U.S. Appl. No. 11/389,762, mailed on Sep. 20, 2007.
Notice of allowance received for U.S. Appl. No. 11/465,527, mailed on Jul. 23, 2010.
Notice of Allowance received for U.S. Appl. No. 11/552,593, mailed on Jul. 22, 2010.
Notice of allowance received for U.S. Appl. No. 11/552,593, mailed on Mar. 22, 2010.
U.S. Provisional Application filed on Jun. 25, 2007, by Reynolds, U.S. Appl. No. 60/946,063.
U.S. Pat. No. 5,820,544 A, Oct. 1998, Semm (withdrawn).
US. Appl. filed Dec. 12, 2008, Zung et al., U.S. Appl. No. 12/334,085.
Notice of allowance received for U.S. Appl. No. 11/552,593, mailed on Oct. 13, 2009.
Notice of allowance received for U.S. Appl. No. 11/688,722, mailed on Jul. 29, 2010.
Notice of Allowance received for U.S. Appl. No. 11/891,358, mailed on Apr. 10, 2012.
Notice of Allowance received for U.S. Appl. No. 11/891,358, mailed on Nov. 18, 2011.
Notice of Allowance received for U.S. Appl. No. 11/891,513, mailed on May 8, 2012.
Notice of Allowance received for U.S. Appl. No. 11/891,513, mailed on Nov. 1, 2011.
Notice of Allowance received for U.S. Appl. No. 11/960,593, mailed on Jul. 1, 2013.
Notice of Allowance received for U.S. Appl. No. 11/997,379, mailed on May 11, 2012.
Notice of Allowance received for U.S. Appl. No. 12/247,012, mailed on Aug. 13, 2012.
Notice of Allowance received for U.S. Appl. No. 12/257,127, filed Sep. 20, 2012.
Notice of Allowance received for U.S. Appl. No. 12/257,127, mailed on Sep. 20, 2012.

(56) References Cited

OTHER PUBLICATIONS

Notice of Allowance received for U.S. Appl. No. 12/334,077, mailed on Oct. 11, 2013.
Notice of Allowance received for U.S. Appl. No. 12/334,085, mailed on Jan. 9, 2012.
Notice of Allowance received for U.S. Appl. No. 12/873,728, mailed on Nov. 4, 2013.
Notice of Allowance received for U.S. Appl. No. 12/950,338, mailed on Aug. 8, 2012.
Notice of Allowance received for U.S. Appl. No. 12/950,338, mailed on Nov. 1, 2011.
Notice of Allowance received for U.S. Appl. No. 12/955,863, mailed on May 15, 2012.
Notice of Allowance received for U.S. Appl. No. 12/955,869, mailed on Mar. 22, 2012.
Notice of Allowance received for U.S. Appl. No. 12/961,239, mailed on Jul. 26, 2011.
Notice of Allowance received for U.S. Appl. No. 12/966,961, mailed on Aug. 18, 2011.
Notice of Allowance received for U.S. Appl. No. 13/022,050, mailed on Jul. 6, 2012.
Notice of Allowance received for U.S. Appl. No. 13/443,659, mailed on Jun. 11, 2014.
Notice of Allowance received for U.S. Appl. No. 13/455,053, mailed on Jun. 9, 2014.
Notice of Allowance received for U.S. Appl. No. 13/485,388, mailed on Oct. 7, 2015.
Notice of Allowance received for U.S. Appl. No. 13/525,875, mailed on Dec. 10, 2014.
Notice of Allowance received for U.S. Appl. No. 13/593,154, mailed on Jan. 8, 2013.
Notice of Allowance received for U.S. Appl. No. 13/615,523, mailed on Nov. 30, 2016.
Notice of Allowance received for U.S. Appl. No. 13/615,530, mailed on Jun. 12, 2013.
Notice of Allowance received for U.S. Appl. No. 13/752,095, mailed on Jun. 12, 2015.
Notice of Allowance received for U.S. Appl. No. 13/791,858, mailed on Mar. 15, 2016.
Notice of Allowance received for U.S. Appl. No. 13/870,628, mailed on Nov. 12, 2015.
Notice of Allowance received for U.S. Appl. No. 14/674,756, mailed on Sep. 18, 2017.
Notice of Allowance received for U.S. Appl. No. 14/880,894, filed Nov. 21, 2018.
Notice of Allowance received for U.S. Appl. No. 14/880,894, mailed on Nov. 21, 2018.
Notice of Allowance received for U.S. Appl. No. 15/005,880, mailed on Jul. 13, 2018.
Notice of Allowance received for U.S. Appl. No. 15/069,515, mailed on Mar. 20, 2018.
Notice of Allowance received for U.S. Appl. No. 15/186,730, mailed on Jul. 1, 2019.
Notice of Allowance received for U.S. Appl. No. 15/192,481, mailed on May 6, 2019.
Notice of Allowance received for U.S. Appl. No. 15/434,907, mailed on May 7, 2019.
Notice of Allowance received for U.S. Patent Application No. 2005/0149065 mailed on Sep. 10, 2007.
Notice of Allowance received for U.S. Patent Application No. 2006/0167476 mailed on Sep. 20, 2007.
Notice of Allowance received for U.S. Pat. No. 5,417,699 mailed on Nov. 3, 1994.
Notice of Allowance received for U.S. Pat. No. 5,527,322 mailed on Dec. 15, 1995.
Notice of Allowance received for U.S. Pat. No. 5,613,974 mailed on May 22, 1996.
Notice of Allowance received for U.S. Pat. No. 5,779,719 mailed on Feb. 6, 1998.
Notice of Allowance received for U.S. Pat. No. 6,036,699 mailed on Jul. 15, 1999.
Office Action received for U.S. Appl. No. 09/707,746, mailed on Jul. 7, 2005.
Office Action received for U.S. Appl. No. 09/769,109, mailed on Jun. 17, 2002.
Office Action received for U.S. Appl. No. 09/769,109, mailed on Oct. 23, 2001.
Office Action received for U.S. Appl. No. 09/988,541, mailed on Aug. 24, 2005.
Office Action received for U.S. Appl. No. 09/988,541, mailed on Feb. 28, 2005.
Office Action received for U.S. Appl. No. 09/988,541, mailed on Mar. 17, 2004.
Office Action received for U.S. Appl. No. 09/988,541, mailed on May 25, 2005.
Office Action received for U.S. Appl. No. 09/988,541, mailed on Nov. 8, 2005.
Office Action received for U.S. Appl. No. 10/033,689, mailed on Sep. 30, 2003.
Office action received for U.S. Appl. No. 10/152,272, mailed on Jan. 24, 2005.
Office Action received for U.S. Appl. No. 10/335,065, mailed on Jun. 10, 2005.
Office Action received for U.S. Appl. No. 10/335,065, mailed on Mar. 17, 2005.
Office action received for U.S. Appl. No. 10/335,147, mailed on Apr. 17, 2006.
Office action received for U.S. Appl. No. 10/335,147, mailed on Dec. 13, 2005.
Office Action received for U.S. Appl. No. 10/357,984, mailed on Jan. 9, 2006.
Office action received for U.S. Appl. No. 10/357,984, mailed on Mar. 16, 2006.
Office action received for U.S. Appl. No. 10/357,984, mailed on Mar. 23, 2007.
Office action received for U.S. Appl. No. 10/357,984, mailed on Nov. 14, 2007.
Office action received for U.S. Appl. No. 10/357,984, mailed on Sep. 28, 2006.
Office action received for U.S. Appl. No. 10/652,182, mailed on Aug. 9, 2006.
Office action received for U.S. Appl. No. 10/660,288, mailed on Apr. 29, 2009.
Office action received for U.S. Appl. No. 10/660,288, mailed on Aug. 3, 2009.
Office action received for U.S. Appl. No. 10/660,288, mailed on Aug. 24, 2006.
Office action received for U.S. Appl. No. 10/660,288, mailed on Feb. 1, 2007.
Office action received for U.S. Appl. No. 10/660,288, mailed on Jun. 28, 2007.
Office action received for U.S. Appl. No. 10/660,288, mailed on Mar. 9, 2006.
Office Action received for U.S. Appl. No. 10/660,288, mailed on Mar. 29, 2011.
Office action received for U.S. Appl. No. 10/660,288, mailed on Mar. 30, 2010.
Office action received for U.S. Appl. No. 10/660,288, mailed on Nov. 15, 2005.
Office action received for U.S. Appl. No. 10/729,541, mailed on Dec. 12, 2006.
Office action received for U.S. Appl. No. 10/729,541, mailed on Jan. 8, 2008.
Office Action received for U.S. Appl. No. 10/729,541, mailed on Jun. 18, 2007.
Office action received for U.S. Appl. No. 10/729,541, mailed on May 1, 2009.
Office action received for U.S. Appl. No. 10/729,541, mailed on Sep. 23, 2008.
Office Action received for U.S. Appl. No. 10/737,668, mailed on Feb. 16, 2006.

(56) References Cited

OTHER PUBLICATIONS

Office Action received for U.S. Appl. No. 10/737,668, mailed on Jun. 7, 2007.
Office Action received for U.S. Appl. No. 10/737,668, mailed on Nov. 2, 2005.
Office Action received for U.S. Appl. No. 10/737,668, mailed on Nov. 28, 2007.
Office Action received for U.S. Appl. No. 10/737,668, mailed on Oct. 19, 2006.
Office Action received for U.S. Appl. No. 10/742,406, mailed on Mar. 23, 2007.
Office Action received for U.S. Appl. No. 10/746,210, mailed on Apr. 5, 2007.
Office action received for U.S. Appl. No. 10/746,210, mailed on Aug. 21, 2007.
Office Action received for U.S. Appl. No. 10/813,449, mailed on Aug. 14, 2008.
Office Action received for U.S. Appl. No. 10/813,449, mailed on Aug. 28, 2009.
Office Action received for U.S. Appl. No. 10/813,449, mailed on Feb. 3, 2009.
Office Action received for U.S. Appl. No. 10/813,449, mailed on Jan. 25, 2008.
Office Action received for U.S. Appl. No. 10/813,449, mailed on Jul. 16, 2007.
Office Action received for U.S. Appl. No. 10/813,449, mailed on May 27, 2010.
Office Action received for U.S. Appl. No. 10/813,449, mailed on Sep. 5, 2006.
Office Action received for U.S. Appl. No. 10/813,449, mailed on Sep. 15, 2008.
"The Hemostatic Puncture Closure Device," Kensey Nash Corporation. (undated).
2004/00092964, Office Action, Jan. 9, 2006.
2004/00092964, Office Action, mail date Mar. 16, 2006.
2004/00092964, Office Action, mail date Mar. 23, 2007.
2004/00092964, Office Action, mail date Sep. 28, 2006.
2004/0122449, Office Action, Dec. 12, 2006.
2004/0122449, Office Action, Jun. 18, 2007.
2005/0059982, Office Action, Aug. 24, 2006.
2005/0059982, Office Action, Feb. 1, 2007.
2005/0059982, Office Action, Jun. 28, 2007.
2005/0059982, Office Action, mail date Mar. 9, 2006.
2005/0059982, Office Action, Mailed Nov. 15, 2005.
2005/0070923, Office Action, Jul. 11, 2007.
2005/0143761, Office Action, Apr. 4, 2007.
2006/0079914, Office Action, Jun. 14, 2007.
2006/0142785, Office Action, Jun. 22, 2007.
5,820,544, filed Jun. 1, 1974, Semm, withdrawn.
7,001,400, Notice of Allowance, Apr. 20, 2004.
7,001,400, Office Action, Feb. 28, 2003.
7,001,400, Office Action, Nov. 7, 2003.
U.S. Appl. No. 90/006,469, mail date Jun. 27, 2006, Re-Examination Certification.
AD: The Laurus In-Line Endoscopic Suturing Device (The Laurus ND-2600 Needle Driver), Laurus Medical Corp., Rev. Oct. 1994.
Advisory Action received for U.S. Appl. No. 14/511,730, mailed on May 22, 2019.
Cardio-Thoracic Systems Prospectus dated Mar. 20, 1996. pp. 1-4, 25-40.
Datascope Corporation, Montvale, N.J., (1991) 1 page, American Heart Assoc. meeting, Anaheim.
Definition of "pair", Dictionary.com, accessed on May 5, 2014.
Elgiloy Brochure, Jun. 23, 1959; Elgin National Watch Co., Elgin, IL.
Elgin National Watch Company, Product Borchure entitled "Elgiloy, A Cobalt Nickel Spring Alloy", 33 pages, 1959.
Ernst, J et al., "Immediate Sealing of Arterial Puncture Sites After Catheterization and PTCA Using a Vascular Hemostasis Device With Collagen: An International Registry."(undated).
Faulkner, Catherine B., Letter regarding "VasoSeal Vascular Hemostasis", Datascope, New Jersey, 1 page, (1991).
Grossman, W., Cardiac Catheterization and Angiography, 3rd Ed., Lea & Febiger, Philadelphia, pp. 1-49, 52-247. 1986.
Interview Summary received for U.S. Appl. No. 14/511,730, filed Oct. 31, 2018.
Interview Summary received for U.S. Appl. No. 14/511,730, mailed on Oct. 31, 2018.
Interview Summary received for U.S. Appl. No. 15/005,880, mailed on Jun. 20, 2018.
Interview Summary received for U.S. Appl. No. 15/192,481, filed Oct. 31, 2018.
Interview Summary received for U.S. Appl. No. 15/192,481, mailed on Oct. 31, 2018.
Issue Notification received for U.S. Appl. No. 15/069,515, mailed on May 23, 2018.
Issue Notification received for U.S. Appl. No. 15/434,907 mailed on Sep. 11, 2019.
Kensey Nash Corporation, Exton PA, "The Hemostatic Puncture Closure Device" 2 pages.
Laurus Medical Corporation, "Endoscopic Suturing Made Simple," The Laurus ND-2600 Needle Driver, Irvine, CA., Oct. 1994, p. 1.
Marshall, AC. & Lock, J.E.; "Structural and compliant anatomy of the patent foramen ovale in patients undergoing transcatheter closure", Am. Heart Journ., 140(2):303-307, Aug. 2000.
Marshall, AC. & Lock, J.E.; "Structural and compliant anatomy of the patent foramen ovale in patients undergoing transcatheter closure", Am. Heart Journ., 140(2):303-307, Aug. 2000.
Merino, A et al., "A Vascular Hemostasis Device for Percutaneous Interventional Procedures," Mount Sinai Medical Center, N.Y. (undated).
Nakamura, S et al., Techniques For Palmaz-Schatz Stent Deployment in Lesions With a Large Side Branch, Catheterization and Cardiovascular Diagnosis, 34: 353-361, 1995.
Office Action received for U.S. Appl. No. 11/891,358, mailed on Oct. 19, 2010.
Office Action received for U.S. Appl. No. 11/891,513, mailed on Apr. 9, 2010.
Office Action received for U.S. Appl. No. 11/891,513, mailed on Aug. 31, 2011.
Office Action received for U.S. Appl. No. 11/891,513, mailed on Sep. 28, 2010.
Office Action received for U.S. Appl. No. 11/960,593, mailed on Apr. 28, 2011.
Office Action received for U.S. Appl. No. 11/960,593, mailed on Nov. 3, 2010.
Office Action received for U.S. Appl. No. 11/960,593, mailed on Sep. 14, 2010.
Office Action received for U.S. Appl. No. 11/997,379, mailed on Feb. 28, 2012.
Office Action received for U.S. Appl. No. 11/997,379, mailed on Jul. 13, 2011.
Office Action received for U.S. Appl. No. 12/182,836, mailed on Jun. 23, 2011.
Office Action received for U.S. Appl. No. 12/182,836, mailed on May 17, 2013.
Office Action received for U.S. Appl. No. 12/182,836, mailed on Oct. 5, 2010.
Office Action received for U.S. Appl. No. 12/247,012, filed Mar. 16, 2012.
Office Action received for U.S. Appl. No. 12/247,012, mailed on Mar. 16, 2012.
Office Action received for U.S. Appl. No. 12/247,012, mailed on Oct. 13, 2011.
Office Action received for U.S. Appl. No. 12/257,127, mailed on Aug. 30, 2010.
Office Action received for U.S. Appl. No. 12/257,127, mailed on Dec. 22, 2010.
Office Action received for U.S. Appl. No. 12/257,127, mailed on Jan. 12, 2012.
Office Action received for U.S. Appl. No. 12/257,127, mailed on Jul. 6, 2011.

(56) References Cited

OTHER PUBLICATIONS

Office Action received for U.S. Appl. No. 12/334,077, mailed on Jan. 16, 2013.
Office Action received for U.S. Appl. No. 12/334,077, mailed on Jul. 21, 2011.
Office Action received for U.S. Appl. No. 12/334,077, mailed on Oct. 27, 2010.
Office Action received for U.S. Appl. No. 12/334,085, mailed on Aug. 4, 2011.
Office Action received for U.S. Appl. No. 12/334,085, mailed on Dec. 23, 2010.
Office Action received for U.S. Appl. No. 12/873,728, mailed on Aug. 23, 2013.
Office Action received for U.S. Appl. No. 12/873,728, mailed on May 3, 2013.
Office Action received for U.S. Appl. No. 12/950,338, mailed on Jun. 15, 2011.
Office Action received for U.S. Appl. No. 12/955,848, filed Jun. 30, 2011.
Office Action received for U.S. Appl. No. 12/955,848, mailed on Jun. 30, 2011.
Office Action received for U.S. Appl. No. 12/955,848, mailed on Nov. 15, 2011.
Office Action received for U.S. Appl. No. 12/955,863, mailed on Jan. 6, 2012.
Office Action received for U.S. Appl. No. 12/955,869, mailed on Oct. 18, 2011.
Office Action received for U.S. Appl. No. 13/022,050, mailed on Apr. 26, 2012.
Office Action received for U.S. Appl. No. 13/022,050, mailed on Jul. 11, 2011.
Office Action received for U.S. Appl. No. 13/333,411, mailed on Dec. 18, 2014.
Office Action received for U.S. Appl. No. 13/443,659, mailed on Nov. 13, 2013.
Office Action received for U.S. Appl. No. 13/455,053, mailed on Nov. 27, 2013.
Office Action received for U.S. Appl. No. 13/525,875, mailed on May 28, 2014.
Office Action received for U.S. Appl. No. 13/525,875, mailed on Sep. 30, 2014.
Office Action received for U.S. Appl. No. 13/615,523, mailed on Aug. 18, 2016.
Office Action received for U.S. Appl. No. 13/615,523, mailed on Feb. 26, 2016.
Office Action received for U.S. Appl. No. 13/615,530, mailed on Jan. 17, 2013.
Office Action received for U.S. Appl. No. 13/752,095, filed Oct. 17, 2014.
Office Action received for U.S. Appl. No. 13/752,095, mailed on Oct. 17, 2014.
U.S. Appl. filed Apr. 24, 2012, Fortson et al., U.S. Appl. No. 13/455,053.
U.S. Appl. filed Apr. 25, 2013, Ma., U.S. Appl. No. 13/870,628.
U.S. Appl. filed Apr. 4, 2016, Zung et al., 15/090, 150.
U.S. Appl. filed Aug. 18, 2006, Dawn Ma., U.S. Appl. No. 11/465,527.
U.S. Appl. filed Aug. 24, 2005, Sibbitt, JR et al., U.S. Appl. No. 60/711,279.
U.S. Appl. filed Dec. 13, 2010, Modesitt et al., U.S. Appl. No. 12/966,961.
U.S. Appl. filed Dec. 6, 2010, Modesitt et al., U.S. Appl. No. 12/961,239.
U.S. Appl. filed Feb. 16, 2017, Aaron M. Fortson., U.S. Appl. No. 15/434,907.
U.S. Appl. filed Feb. 7, 2011, Pantages et al., U.S. Appl. No. 13/022,050.
U.S. Appl. filed Jan. 28, 2013, McIntosh., U.S. Appl. No. 13/752,095.
U.S. Appl. filed Jun. 18, 2012, Voss., U.S. Appl. No. 13/525,875.
U.S. Appl. filed Jun. 24, 2016, Stafford., U.S. Appl. No. 15/192,481.
U.S. Appl. filed Jun. 25, 2007, Reynolds., U.S. Appl. No. 60/946,063.
U.S. Appl. filed Jun. 30, 2000, Burdulis., U.S. Appl. No. 09/608,832.
U.S. Appl. filed Jun. 30, 2000, Burdulis., U.S. Appl. No. 09/610,564.
U.S. Appl. filed Nov. 29, 2010, Modesitt et al., U.S. Appl. No. 12/955,848.
U.S. Appl. filed Oct. 14, 2005, Sibbitt, Jr. et al., U.S. Appl. No. 60/726,985.
U.S. Appl. filed Sep. 15, 2008, Sibbitt, Jr. et al., U.S. Appl. No. 61/097,072.
U.S. Appl. No. 09/395,901, filed Apr. 20, 2001, Notice of Allowance.
U.S. Appl. No. 10/652,182, filed Aug. 29, 2003.
U.S. Appl. No. 10/660,288, filed Sep. 11, 2003.
U.S. Appl. No. 10/948,445, filed Sep. 22, 2004, McIntosh.
U.S. Appl. No. 11/508,662, filed Dec. 28, 2009, Restriction Requirement.
U.S. Appl. No. 11/508,662, mail date Oct. 26, 2010, Office Action.
U.S. Appl. No. 11/508,715, mail date Oct. 18, 2010, Office Action.
U.S. Appl. No. 11/891,513, filed Apr. 9, 2010, Office Action.
U.S. Appl. No. 11/960,593, dated Jul. 1, 2013, Notice of Allowance.
U.S. Appl. No. 12,955,863, filed Nov. 29, 2010, Ma.
U.S. Appl. No. 12/365,397, filed Feb, 4, 2009, Sibbitt, Jr. et al.
U.S. Appl. No. 12/365,397, Mailed Sep. 13, 2010, Office Action.
U.S. Appl. No. 12/559,377, filed Sep. 14, 2009, Sibbitt, Jr. et al.
U.S. Appl. No. 12/950,338, filed Nov. 19, 2010, Modesitt, et al.
U.S. Appl. No. 12/955,869, filed Nov. 29, 2010, Voss.
U.S. Appl. No. 14/511,730, filed Oct. 10, 2014, Fortson et al.
U.S. Appl. No. 14/674,756, filed Apr. 2, 2015, Voss.
U.S. Appl. No. 14/880,894, filed Oct. 12, 2015, McIntosh.
U.S. Appl. No. 15/005,880, filed Apr. 10, 2018, Office Action.
U.S. Appl. No. 15/005,880, filed Jan. 25, 2016, Roorda et al.
U.S. Appl. No. 15/069,515, filed Mar. 14, 2016, Ma.
U.S. Appl. No. 15/186,730, filed Jun. 20, 2016, Fortson et al.
U.S. Appl. No. 16/052,263, filed Aug. 1, 2018, Roorda et al.
U.S. Appl. No. 90/006,469, filed Sep. 10, 2004, Re-Examination Office Action.
U.S. Application filed on Nov. 29, 2007, by Modesitt et al., U.S. Appl. No. 90/006,469.
U.S. Patent Application filed on Jan. 30, 2008 by Pantages et al., U.S. Appl. No. 11/997,379.
U.S. Patent No. 6, 136,010, Notice of Allowance, Mailed May 30, 2000.
U.S. Patent No. 6, 136,010, Office Action, Mailed Mar. 29, 2000.
U.S. Pat. No. 6,964,668, Notice of Allowance, Mailed May 13, 2005.
U.S. Pat. No. 6,964,668, Office Action, Mailed Jan. 24, 2005.
U.S. Provisional Application filed on Jan. 30, 2004, by McIntosh, U.S. Appl. No. 60/540,811.

* cited by examiner

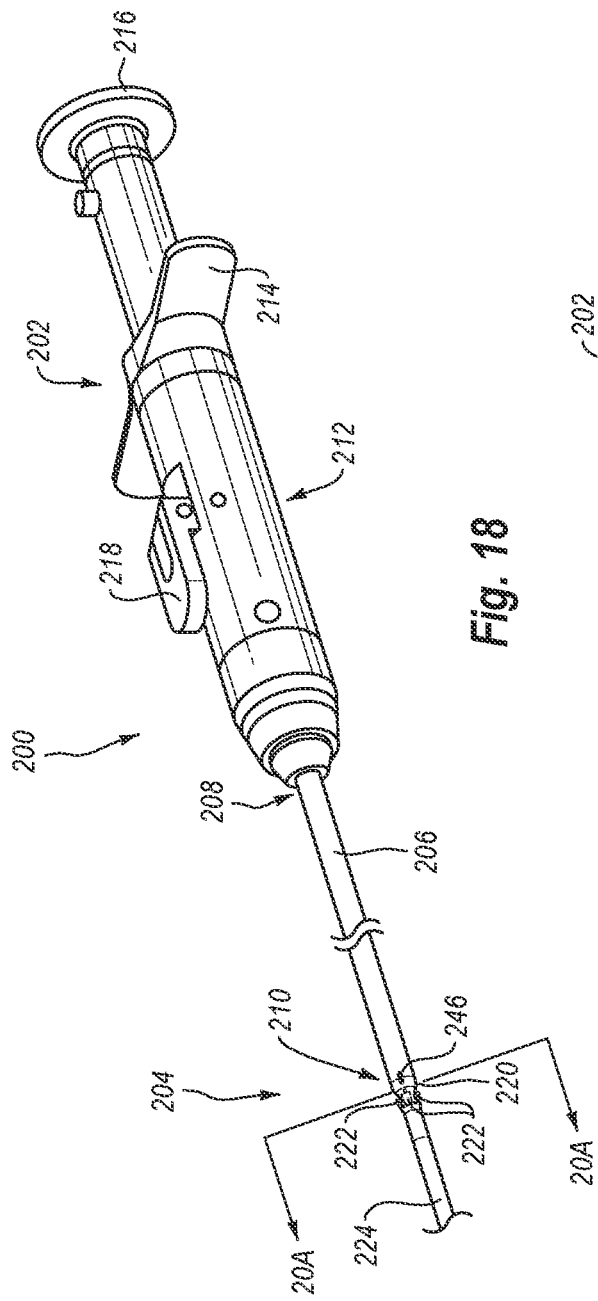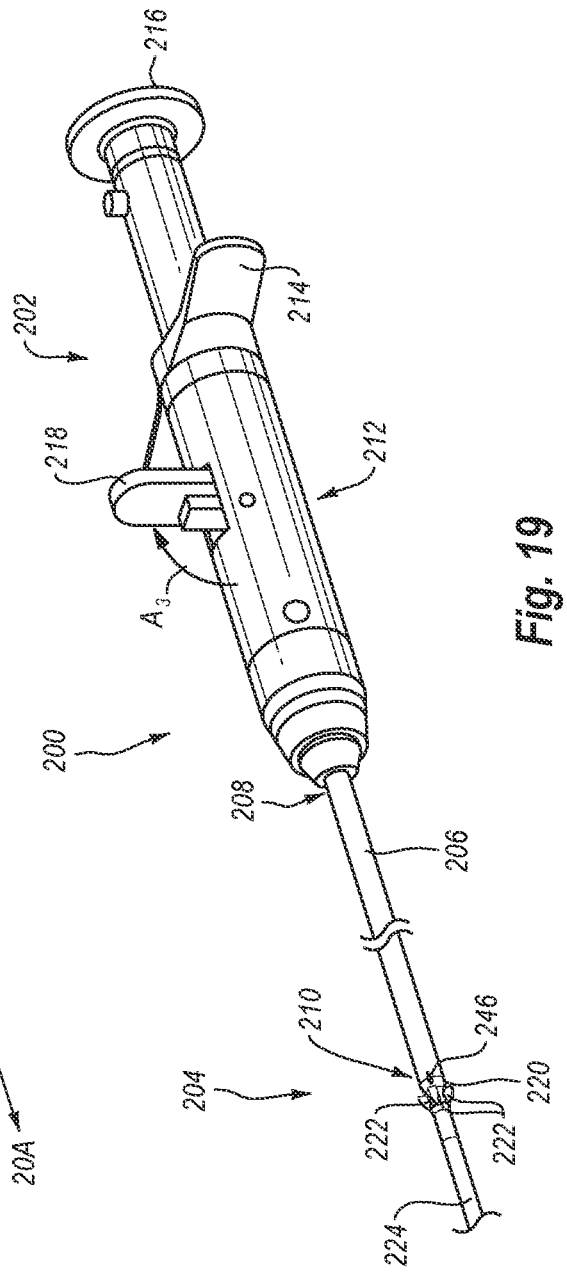

SYSTEMS, METHODS, AND DEVICES FOR CLOSING HOLES IN BODY LUMENS

CROSS-REFERENCE TO RELATED APPLICATIONS

This application is a continuation of U.S. patent application Ser. No. 17/130,764, filed Dec. 22, 2020, entitled "SYSTEMS, METHODS, AND DEVICES FOR CLOSING HOLES IN BODY LUMENS", now U.S. Pat. No. 11,839, 351, which is a continuation of U.S. patent application Ser. No. 16/052,263, filed Aug. 1, 2018, entitled "SYSTEMS, METHODS, AND DEVICES FOR CLOSING HOLES IN BODY LUMENS", now U.S. Pat. No. 10,980,531, which is a continuation of U.S. patent application Ser. No. 15/005, 880, filed Jan. 25, 2016, entitled "SYSTEMS, METHODS, AND DEVICES FOR CLOSING HOLES IN BODY LUMENS", now U.S. Pat. No. 10,111,653, which is a divisional application of U.S. patent application Ser. No. 13/485,388, filed May 31, 2012, now U.S. Pat. No. 9,241, 707 entitled "SYSTEMS, METHODS, AND DEVICES FOR CLOSING HOLES IN BODY LUMENS", the entire contents of which are incorporated by reference herein.

BACKGROUND

1. Technical Field

The present disclosure relates generally to techniques and devices for closing openings in body lumens. More particularly, the present disclosure relates to systems, devices, and methods for percutaneous closure of arterial and venous puncture sites, which are usually accessed through a tissue tract.

2. The Relevant Technology

A number of diagnostic and interventional vascular procedures are now performed translumenally. A catheter is introduced to the vascular system at a convenient access location and guided through the vascular system to a target location using established techniques. Such procedures require vascular access, which is usually established using the well-known Seldinger technique. Vascular access is generally provided through an introducer sheath, which is positioned to extend from outside the patient's body into the vascular lumen. When vascular access is no longer required, the introducer sheath is removed and bleeding at the puncture site stopped.

One common approach for providing hemostasis (the cessation of bleeding) is to apply external force near and upstream from the puncture site, typically by manual compression. This approach suffers from a number of disadvantages. For example, the manual compression procedure is time consuming, frequently requiring one-half hour or more of compression before hemostasis is achieved. Additionally, such compression techniques rely on clot formation, which can be delayed until anticoagulants used in vascular therapy procedures (such as for heart attacks, stent deployment, non-optical PTCA results, and the like) wear off. The anticoagulants may take two to four hours to wear off, thereby increasing the time required before completion of the manual compression procedure.

Further, the manual compression procedure is uncomfortable for the patient and frequently requires analgesics to be tolerable. Moreover, the application of excessive pressure can at times totally occlude the underlying blood vessel, resulting in ischemia and/or thrombosis. Following manual compression, the patient typically remains recumbent from four to as much as twelve hours or more under close observation to assure continued hemostasis. During this time, renewed bleeding may occur, resulting in blood loss through the tract, hematoma and/or pseudo-aneurysm formation, as well as arteriovenous fistula formation. These complications may require blood transfusions and/or surgical intervention.

The incidence of complications from the manual compression procedure increases when the size of the introducer sheath grows larger, and/or when the patient is anticoagulated. The compression technique for arterial closure can be risky, and is expensive and onerous to the patient. Although using highly trained individuals can reduce the risk of complications, dedicating such personnel to this task is both expensive and inefficient. Nonetheless, as the number and efficacy of translumenally performed diagnostic and interventional vascular procedures increases, the number of patients requiring effective hemostasis for a vascular puncture continues to increase.

To overcome the problems associated with manual compression, the use of bioabsorbable sealing bodies is one example approach that has been proposed. Generally, this example approach relies on the placement of a thrombogenic and bioabsorbable material, such as collagen, at the superficial arterial wall over the puncture site. While potentially effective, this approach suffers from a number of drawbacks. For example, bioabsorbable sealing bodies may lack a solid mechanical attachment of the sealing body to the tissue. Due to the lack of a solid mechanical attachment, the sealing body can wander within the tissue tract or move out of the puncture site, thus causing late bleeds. Conversely, if the sealing body wanders and intrudes too far into the arterial lumen, due to the lack of a solid mechanical attachment, intravascular clots and/or collagen pieces with thrombus attached can form and embolize downstream, causing vascular occlusion.

In addition to not having a solid mechanical attachment to the tissue, the sealing bodies may rely upon expandable materials to achieve hemostasis. Again, the expandable materials lack the security of a hard mechanical closure, thus potentially causing late bleeds and prolonging hemostasis.

For these reasons, it would be desirable to provide improved devices and methods to seal body lumen puncture sites. It would be particularly desirable to provide percutaneous devices and methods for suturing the puncture sites required for percutaneous vascular procedures.

BRIEF SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Embodiments of the present invention provide systems, methods, and devices for closing an opening in tissue. Embodiments of the invention can be configured to close an opening within a body lumen.

For instance, in one exemplary embodiment, a device for closing an opening in tissue includes an elongate member, a plurality of needles, a foot housing, and a foot. The elongate member has a plurality of needle lumens extending from the proximal end toward the distal end. The needles are disposed within and are advanceable from the plurality of needle lumens. The foot housing is disposed at the distal end of the elongate member and defines a first opening and a second opening therein. The foot is slidably mounted within the foot housing and through the first opening between a delivery position and a deployed position. The foot includes at least two cuffs removably mounted in a first end and at least two cuffs removably mounted in a second, opposing end. A length of suture is connected between each cuff in the first end of the foot and each cuff in the second end of the foot. The cuffs in the first end of the foot are positioned below and accessible through the second opening in the foot housing and the cuffs in the second end of the foot are positioned outside the foot housing when the foot is in the deployed position. In contrast, the cuffs in the first end of the foot are substantially inaccessible through the second opening in the foot housing when the foot is in the delivery position.

According to another implementation of the present invention, a device for closing an opening in a body lumen includes an elongate member and a plurality of needles as mentioned. In addition, the device includes a foot portion disposed at the distal end of the elongate member and a plurality of feet slidably mounted on the foot portion. Each foot of the plurality of feet is slidable between a delivery position and a deployed position. The plurality of feet moves both proximally along the length of the foot portion and radially away from the central axis of the foot portion when moving from the delivery position to the deployed position. Also, each foot of the plurality of feet has a cuff removably mounted therein. A length of suture is connected between each pair of cuffs. The device also includes a track and track guide system to facilitate movement of the feet between the delivery and deployed positions.

In still another exemplary embodiment, a needle includes a shaft having a proximal end, a distal end, and a longitudinal axis, and a plurality of needle tips extending from the distal end of the shaft. The plurality of needle tips can be generally aligned with and parallel to one another. Alternatively, the plurality of needle tips can be generally parallel to and offset from one another.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 18 is an elevation view of a closure device in accordance with another exemplary embodiment of the present invention;

FIG. 19 is another elevation view of the closure device of FIG. 14, showing foot lobes in deployed position;

DETAILED DESCRIPTION

As used herein, the term "distal" is generally defined as in the direction of the patient or away from a user of a device. In the context of a medical device intervention with or through a vessel wall, "distal" herein refers to the interior or the lumen side of the vessel wall. Conversely, "proximal" generally means away from the patient or toward the user. In the context of a medical device intervention with or through a vessel wall, "proximal" herein refers to the exterior or outer side of the vessel wall.

The term "suturing" is herein intended to include the process of joining two surfaces or edges together with a fastener or so as to close an aperture, opening, or wound, or join tissues. The fastener is usually a suture such as a thread of material (either polymeric or natural), gut, wire, or the like. The term fastener as used herein also includes clamps, studs, hasps, catches, hooks, rivets, staples, snaps, stitches, VELCROC, buttons, and other coupling members.

Referring to the Figures, suture applying devices that are suitable for suturing and sealing of percutaneous vascular puncture sites, such as those made to the femoral artery in a patient's groin, will be described. It will be appreciated, however, that the devices of the present invention can be readily adapted for use with punctures made to other hollow body organs and lumens, although it may be necessary to modify the dimensions and other particular aspects of the devices to accommodate the different usage environments.

Figure 1:
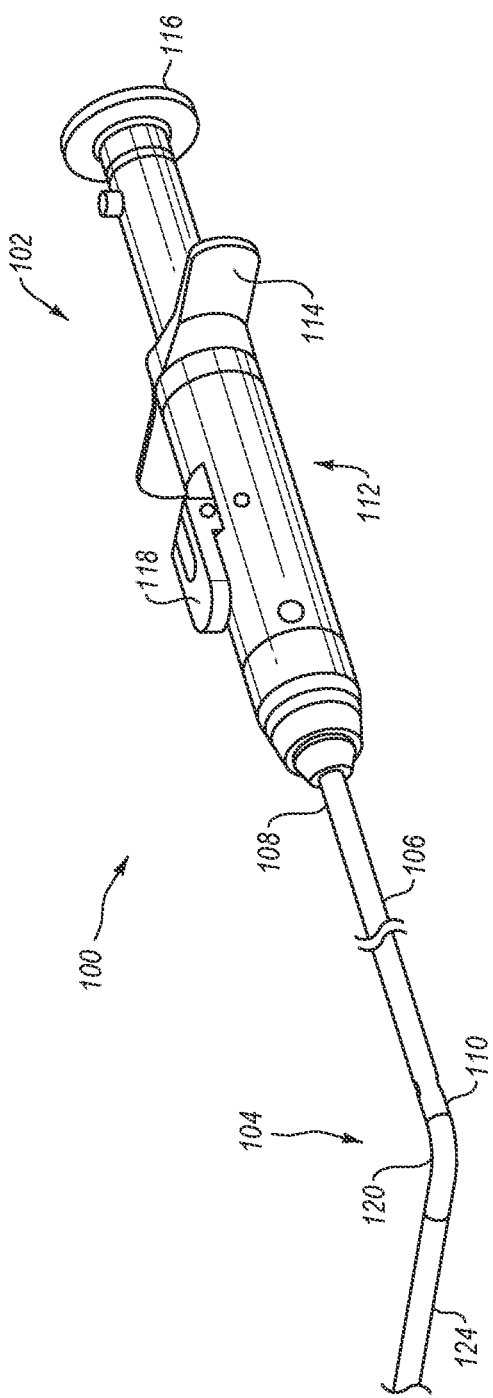
FIG. 1 is an elevation view of a closure device in accordance with one exemplary embodiment of the present invention.
Figure 2:
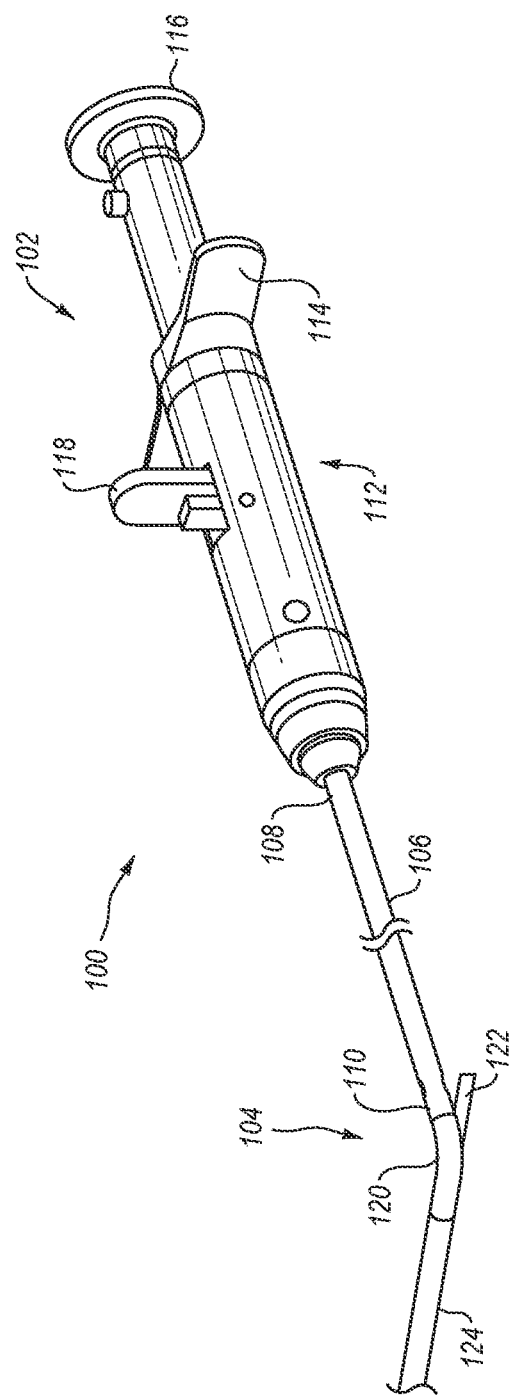
FIG. 2 is another elevation view of the closure device of FIG. 1, showing a foot in a deployed position.

FIGS. 1 and 2 illustrate one example embodiment of a closure device 100. Closure device 100 includes a proximal end 102 and a distal end 104. As shown in FIGS. 1 and 2, closure device 100 includes an elongate member 106 that has a proximal end 108 and a distal end 110. As discussed in greater detail below, elongate member 106 is generally tubular and includes one or more lumens that extend generally from proximal end 108 to distal end 110. The one or more lumens may be used to facilitate the delivery of device 100 over a guidewire or to deliver one or more needles into a patient. In one embodiment, elongate member 106 is formed of a rigid material such as a stainless steel or other biocompatible material that is rigid. Alternatively, elongate member 106 may be formed of a flexible material such as those materials utilized to form catheter shafts, introducer sheaths, or other medical devices. Suitable materials include polyvinyl chloride (PVC), peak, PTFE, nylon, or any other similar materials.

Connected to proximal end 108 of elongate member 106 is an actuator mechanism 112. Actuator mechanism 112 includes a handle 114 to facilitate manipulation of device 100. Actuator mechanism 112 also includes a plunger 116 used to deploy and retract needles from elongate member 106, and a lever 118 used to selectively deploy and retract a foot, as discussed in greater detail below.

As shown in FIGS. 1 and 2, distal end 104 of device 100 includes a foot portion 120 attached to or extending from distal end 110 of elongate member 106. In the illustrated embodiment, foot portion 120 is in the form of a foot housing. Elongate member 106 and foot portion 120 may be discrete pieces that are coupled together, or elongate member 106 and foot portion 120 may be integrally formed as a single piece.

A foot 122 is movably disposed within foot portion 120. Foot 122 moves between a delivery position, in which foot 122 is positioned substantially or entirely within foot portion 120 (as illustrated in FIG. 1), and a deployed position, in which foot 122 extends at least partially out of foot portion 120 (as illustrated in FIG. 2). When foot 122 is in the delivery configuration, distal end 104 can be inserted through a puncture site and into a body lumen of a patient. Once distal end 104 is positioned within the body lumen, foot 122 may be moved to the deployed position. When in the deployed position, foot 122 increases the profile of distal end 104, which prevents distal end 104 from being inadvertently pulled out of the body lumen through the puncture site. Additionally, foot 122 may also be used as a locator to assist a physician in properly positioning distal end 104 within the body lumen. As will be discussed in greater detail below, foot 122 is operatively connected to lever 118 such that foot 122 may be selectively moved between the delivery position and the deployed position by actuating lever 118.

FIGS. 1 and 2 further illustrate that device 100 optionally includes a flexible guidebody 124 extending distally from the distal end of foot portion 120. As explained in greater detail below, guidebody 124 can be advanced along a guidewire into a body lumen. Accordingly, at least the distal portion of guidebody 124 can be formed from a flexible or elastomeric material that is biocompatible, particularly with blood.

Figure 3:
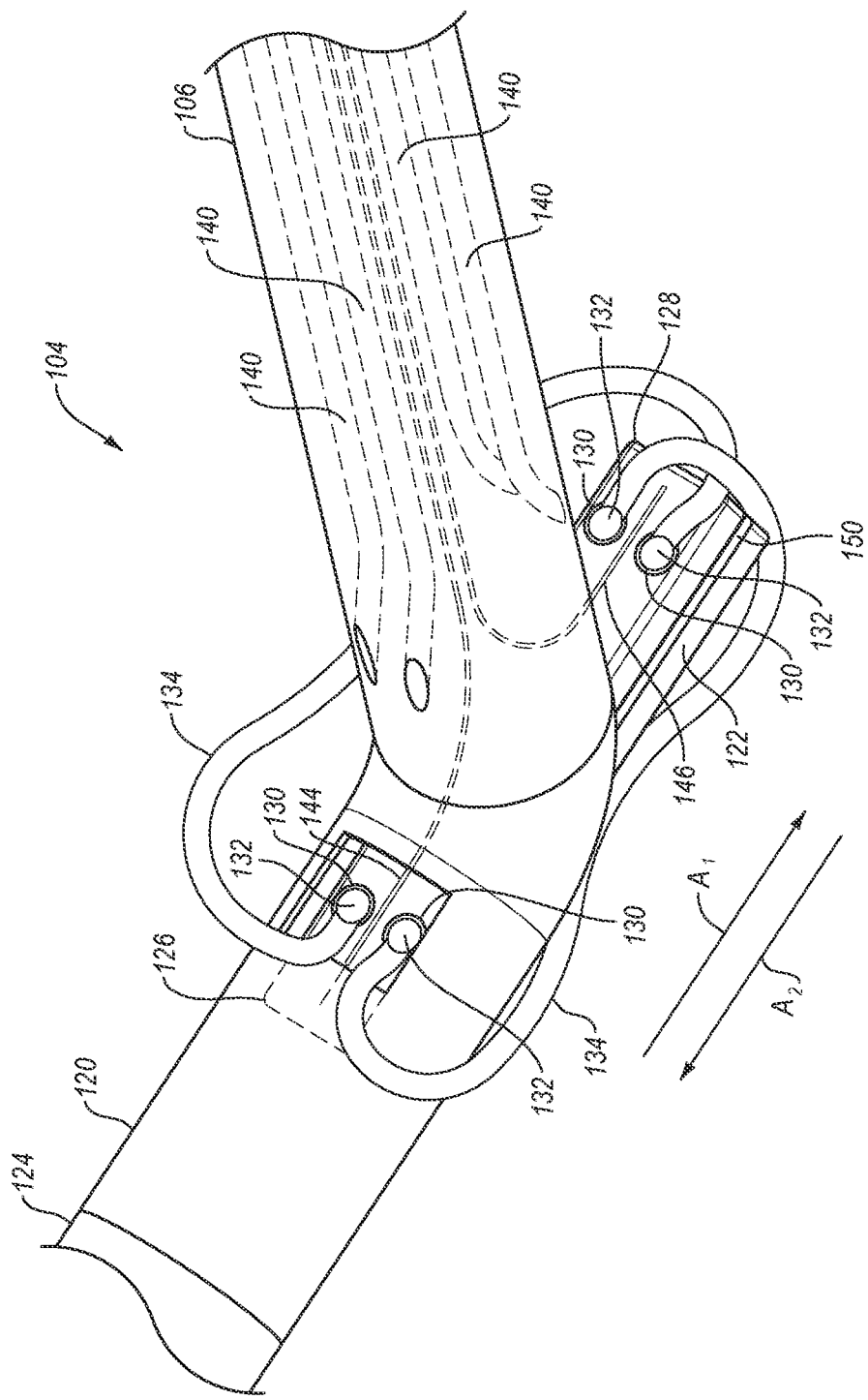
FIG. 3 is a close-up view of a distal end of the closure device of FIG. 1, showing the foot in the deployed position.

Turning attention to FIG. 3, a close-up perspective view of distal end 104 is illustrated. As can be seen in FIG. 3, foot 122 includes a first or distal end 126 and a second or proximal end 128. In the illustrated embodiment, each of first and second ends 126, 128 includes two cuff receptacles 130. A cuff 132 (with an associated end of a suture 134) is releasably disposed within each cuff receptacle 130. Each suture 134 is connected between cuffs 132 disposed in opposing ends of foot 122. A surface of each cuff receptacle 130 may taper or be funnel shaped so as to guide advancing needles into engagement with cuffs 132 when foot 122 is in the deployed position.

Figure 3A:
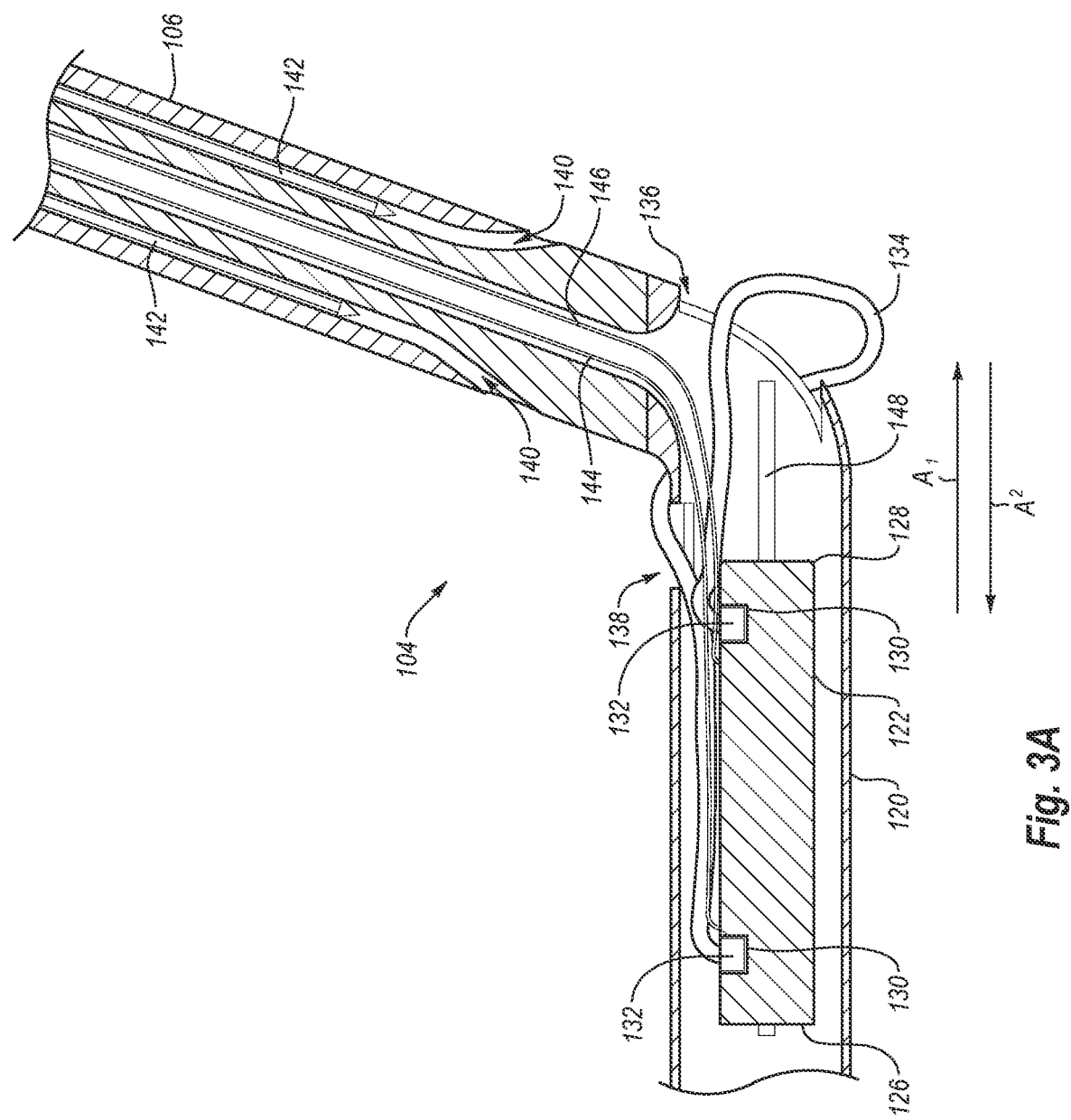
FIG. 3A is a cross-sectional view of the distal end of the closure device of FIG. 1, with the foot in the delivery position.
Figure 3B:
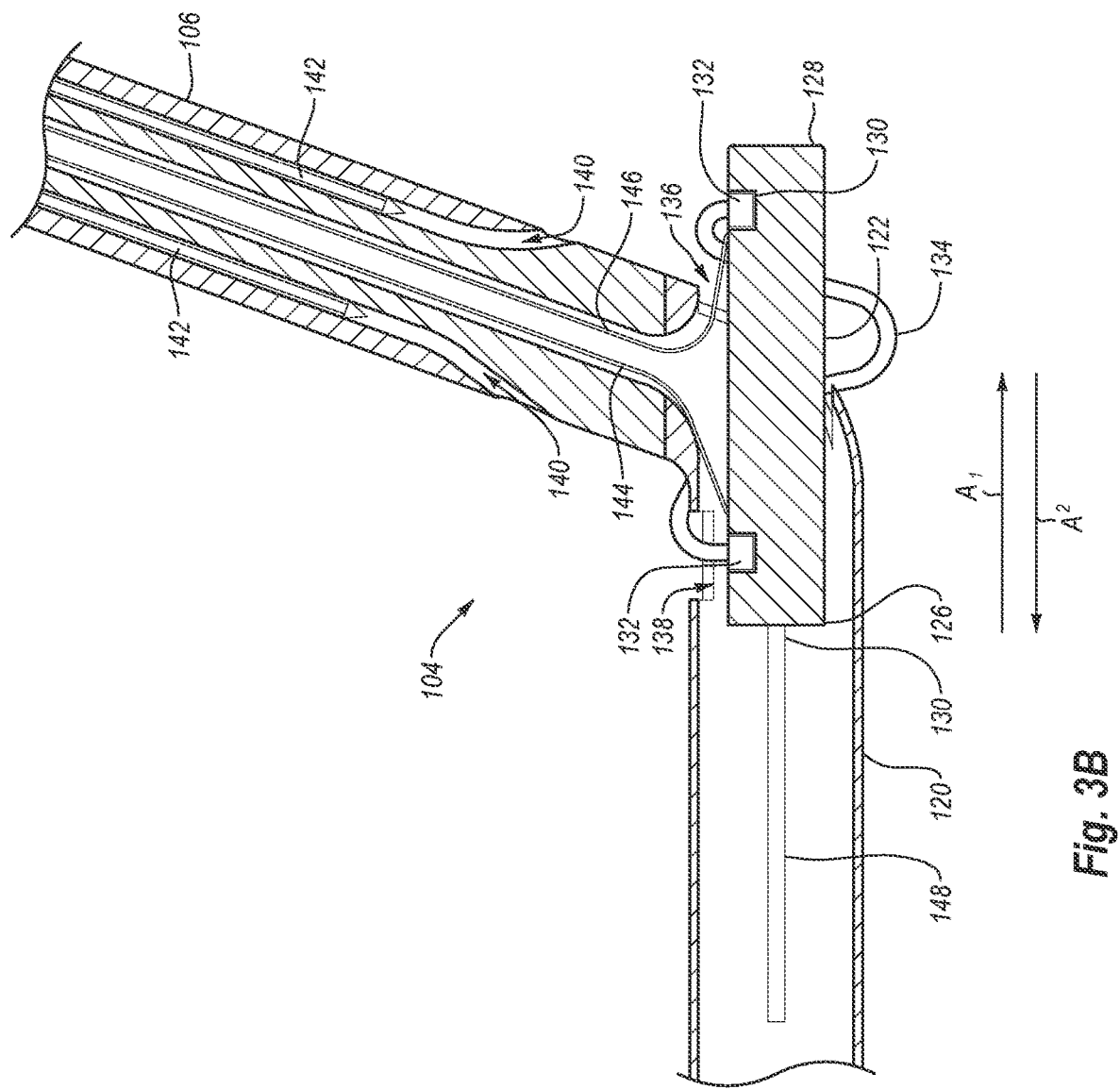
FIG. 3B is a cross-sectional view of the distal end of the closure device of FIG. 1, with the foot in the deployed position.

As shown in the cross-sectional view of FIG. 3A, foot 122 is in the delivery position such that foot 122 is positioned substantially entirely within foot portion 120. In contrast, FIGS. 3 and 3B illustrate foot 122 in the deployed position. That is, in the deployed position, second end 128 of foot 122 extends outside of foot portion 120 while first end 126 remains positioned within foot portion 120. Foot portion 120 includes an opening or window 136 to enable second end 128 to move in and out of foot portion 120 between the delivery and deployed positions.

As can be seen in FIGS. 3 and 3B, the cuff receptacles 130 and cuffs 132 in second end 128 are generally aligned with one or more needle lumens 140 in elongate member 106 when foot 122 is in the deployed position. As noted above, one or more needles 142 may be passed through or extended from needle lumens 140. Aligning cuff receptacles 130 and cuffs 132 with needle lumens 140 enables needles 142 to be extended from needle lumens 140 toward cuff receptacles 130 so that needles 142 may engage cuffs 132, as discussed in greater detail below.

Foot portion 120 also includes a second opening or window 138. Window 138 provides access to first end 126 of foot 122. More particularly, the cuff receptacles 130 and cuffs 132 in first end 126 are accessible through window 138 when foot 122 is in the deployed position. Additionally, the cuff receptacles 130 and cuffs 132 in first end 126 are generally aligned with one or more needle lumens 140 in elongate member 106 when foot 122 is in the deployed position. As a result of the cuffs 132 in first end 126 being accessible through window 138 and aligned with needle lumens 140 when foot 122 is deployed, needles 142 are extended from needle lumens 140, through window 138, and toward cuff receptacles 130 so that needles 142 may engage cuffs 132, as discussed in greater detail below.

As noted above, foot 122 is movable between a delivery position and a deployed position. In the embodiment illustrated in FIGS. 3-3B, movement of foot 122 to the deployed position is in the direction of arrow $A_1$, while movement of foot 122 to the delivery position is in the direction of arrow $A_2$. Foot 122 may be moved between the delivery and deployed configurations in a variety of ways. The Figures illustrate one exemplary manner in which movement of foot 122 may be accomplished.

In the illustrated embodiment, foot 122 is connected to lever 118 (FIGS. 1 and 2) via cables 144, 146. More specifically, first end 126 of foot 122 is connected to lever 118 via deployment cable 144 and second end 128 of foot 122 is connected to lever 118 via retraction cable 146. When lever 118 is moved from the position shown in FIG. 1 to the position shown in FIG. 2, for example, deployment cable 144 may be drawn proximally up through elongate member 106. As deployment cable 144 is drawn proximally, deployment cable 144 pulls on first end 126 of foot 122. Due to the angle between elongate member 106 and foot portion 120, the pulling of first end 126 by deployment cable 144 causes foot 122 to move in the direction of arrow $A_1$ and toward the deployed position.

Retraction cable 146 works in a similar manner as deployment cable 144 to move foot 122 to the delivery position. More specifically, when lever 118 is moved from the position shown in FIG. 2 to the position shown in FIG. 1, retraction cable 146 is drawn proximally up through elongate member 106. As retraction cable 146 is drawn proximally, retraction cable 146 pulls on second end 128 of foot 122. As best seen in FIG. 3B, when foot 122 is in the deployed position, retraction cable 146 extends through elongate member 106, into foot portion 120, and out window 136 to second end 128. Retraction cable 146 bends to extend from elongate member 106 and out of window 136 toward second end 128. Due to this bend in retraction cable 146, the pulling of second end 128 by retraction cable 146 causes foot 122 to move in the direction of arrow $A_2$ and toward the delivery position.

Foot portion 120 and foot 122 may include additional features that facilitate smooth movement of foot 122 between the delivery and deployed positions. By way of example, foot portion 120 and foot 120 may include a track and track guide system to assist foot 122 in moving smoothly between the delivery and deployed positions. In the illustrated embodiment, foot portion 120 includes track guides 148 on opposing interior surfaces thereof, and foot 120 includes tracks 150 on opposing sides thereof. Tracks 150 are able to slide in track guides 148 as foot 122 moves. Track guides 148 and tracks 150 assist in keeping foot 122 aligned and moving smoothly as cables 144, 146 are moved.

Before leaving FIGS. 3-3B, it is worth noting that sutures 134 extend between cuffs 132 around the outside of foot portion 120. More specifically, each suture 134 extends from a cuff 132 in first end 126 of foot 122, out through window 138, and to a cuff 132 in second end 128 of foot 122. By extending sutures 134 between cuffs 132 outside of foot portion 120, sutures 134 can be readily removed from distal end 104 without being caught in foot portion 120. That is, if a suture 134 extended from a cuff 132 in first end 126, through foot portion 120, and out of window 136 to a cuff 132 in second end 128, when the ends of suture 134 were pulled away from foot 122, suture 134 would be caught in foot portion 120. Accordingly, sutures 134 extend between cuffs 132 in opposing ends of foot 120 and through window 138.

Figure 4A:
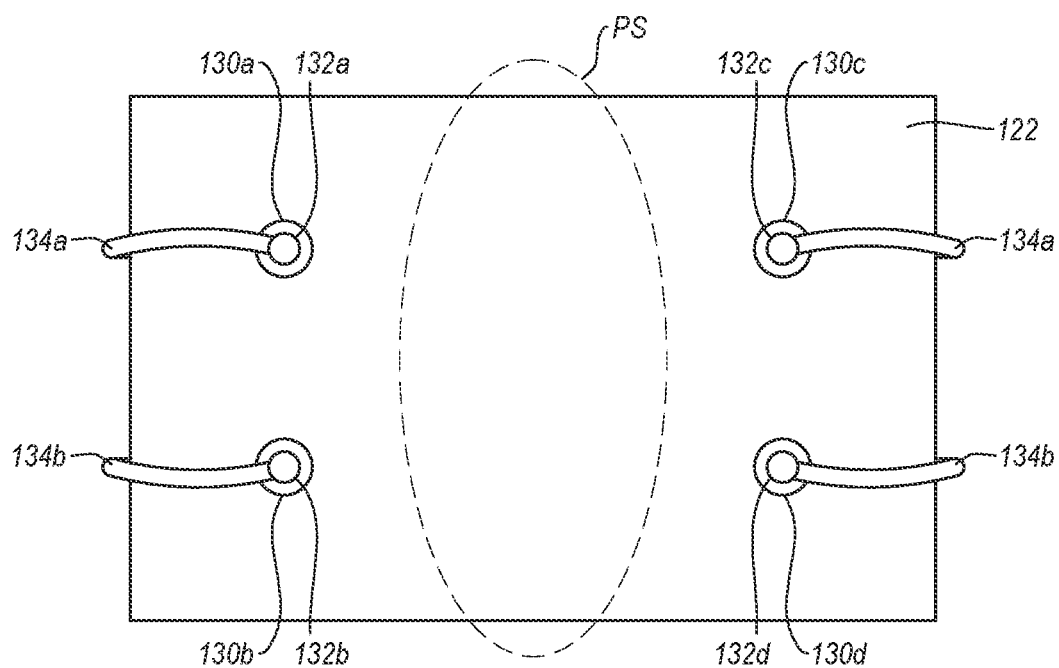
FIG. 4A is a top view of one exemplary foot for use in connection with the closure device of FIG. 1.
Figure 17:
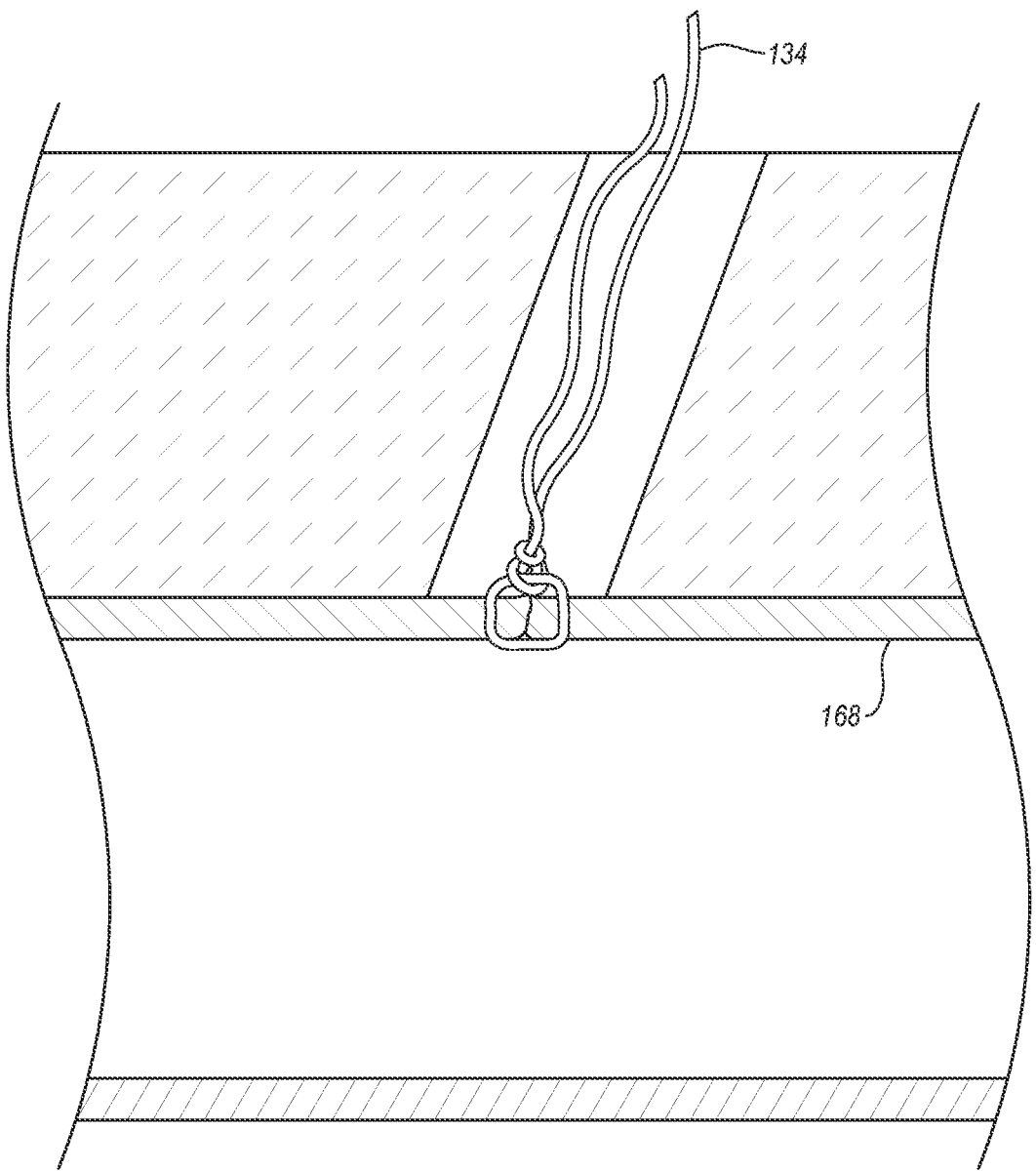
FIG. 17 illustrates a cross-sectional view of the vessel wall showing the suture tied to close the opening in the vessel wall.
Figure 17A:
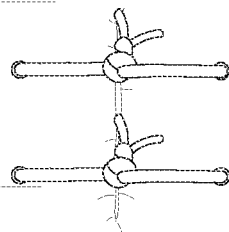
FIGS. 17A-17C illustrate various suture patterns used to close an opening in a vessel wall.

Attention is now directed to FIG. 4A, which illustrates a top view of foot 122 and a puncture site PS (shown in phantom lines). In the illustrated embodiment, foot 122 includes four cuff receptacles 130a, 130b, 130c, 130d, four corresponding cuffs 132a, 132b, 132c, 132d, and two sutures 134a, 134b. Suture 134a is connected between cuffs 132a and 132c and suture 134b is connected between cuffs 132b and 132d. When sutures 134a, 134b are used to close a puncture site PS, sutures 134a, 134b form two generally parallel suture loops around puncture site PS, as shown in FIG. 17A. It will be understood that sutures 134a, 134b may be arranged to form other suture loop patterns. For instance, suture 134a could be connected between cuff 132a and 132d and suture 134b could be connected between cuff 132b and 132c. In such a case, sutures 134a and 134b would create a generally X-shaped suture loop pattern when closing puncture site PS.

While foot 122 has been illustrated and described as including four cuff receptacles and supporting four cuffs and two sutures, it will be appreciated that the present invention may include or utilize greater or fewer cuff receptacles, cuffs, or sutures. Additionally, the cuff receptacles, cuffs, and sutures may be arranged in various patterns. FIGS. 4B-4E illustrate a few additional embodiments of feet, with different numbers of cuff receptacles, cuffs, and sutures, and arranged in a variety of ways. Nevertheless, it will be understood that the illustrated embodiments are provided by way of example only, and that the present invention may include still other arrangements and numbers of cuff receptacles, cuffs, and sutures.

Figure 4B:
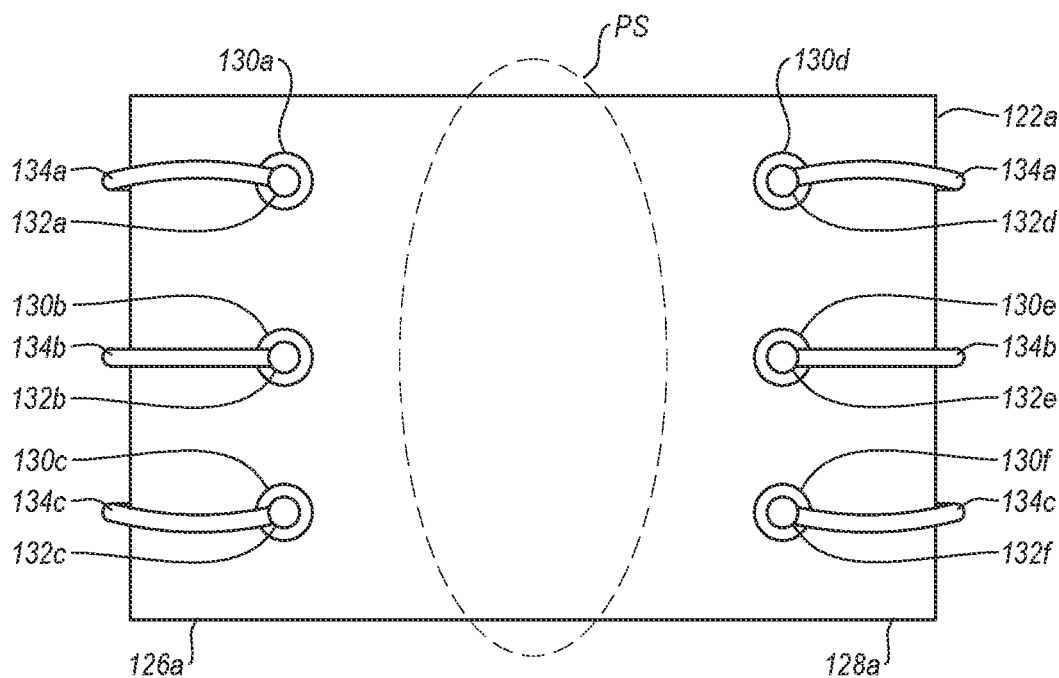
FIG. 4B is a top view of another exemplary foot for use in connection with the closure device of FIG. 1.
Figure 17B:
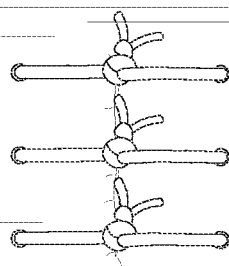

With attention to FIG. 4B, there is illustrated a foot 122a that is similar to foot 122 in many respects. Foot 122a has a first end 126a and a second end 128a. In first end 126a are three generally aligned cuff receptacles 130a, 130b, 130c that receive and support cuffs 132a, 132b, 132c, respectively. Similarly, second end 128a includes three generally aligned cuff receptacles 130d, 130e, 130f that receive and support cuffs 132d, 132e, 132f, respectively. Sutures 134a, 134b, 134c are connected respectively between cuffs 132a and 132d, cuffs 132b and 132e, and cuffs 132c and 132f. When sutures 134a, 134b, 134c are used to close a puncture site PS, sutures 134a, 134b, 134c form three generally parallel suture loops around puncture site PS, as shown in FIG. 17B.

Sutures 134a, 134b, 134c may also be connected to cuffs 132a-f so as to form non-parallel suture loop arrangements. By way of example, suture 134a may be connected between cuffs 132a and 132f, suture 134c may be connected between cuffs 132c and 132d, and suture 134b may be connected between cuffs 132b and 132e. In such a case, sutures 134a, 134b, 134c would form a suture loop pattern around puncture site PS like the pattern shown in FIG. 17C. Other patterns could also be achieved by connecting sutures 134a, 134b, 134c to cuffs 132a-f in other combinations.

Figure 4C:
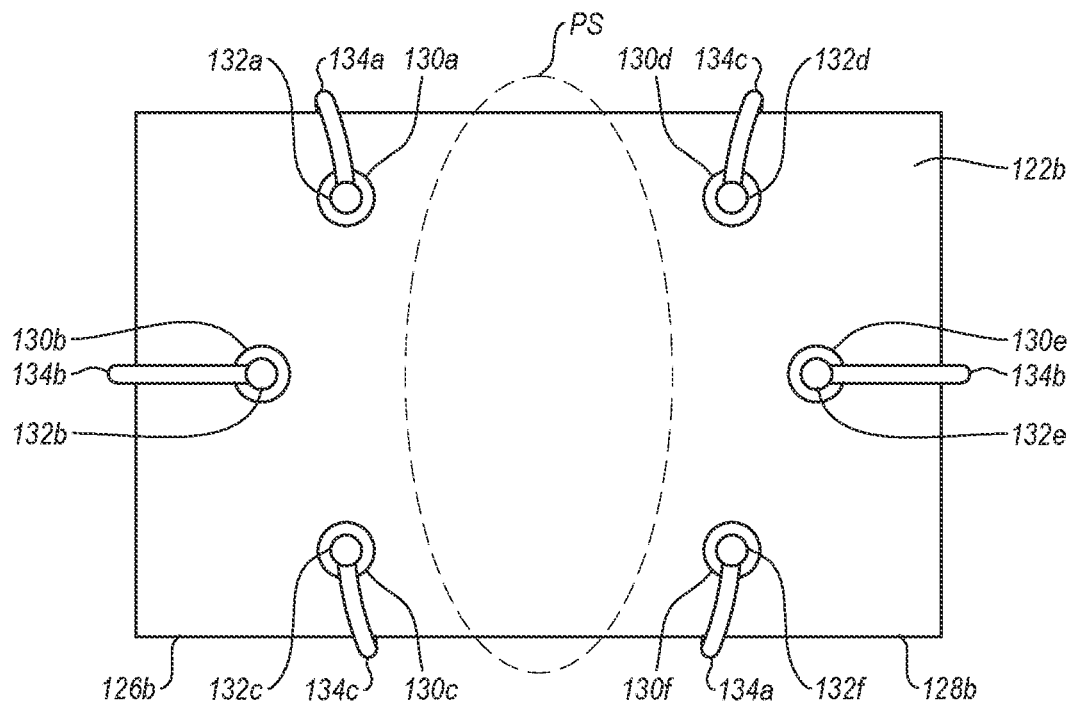
FIG. 4C is a top view of another exemplary foot for use in connection with the closure device of FIG. 1.

Turning attention to FIG. 4C, there is illustrated a foot 122b that is similar to foot 122a in many respects. Foot 122b has a first end 126b and a second end 128b. In first end 126b are three cuff receptacles 130a, 130b, 130c that receive and support cuffs 132a, 132b, 132c, respectively. Similarly, second end 128a includes three cuff receptacles 130d, 130e, 130f that receive and support cuffs 132d, 132e, 132f, respectively. Unlike the cuff receptacles in feet 122, 122a, cuff receptacles 130a-f in foot 122b are not all generally aligned. Rather, cuff receptacles 130a, 130c, 130d, 130f are arranged in a generally rectangular pattern, while cuff receptacles 130b, 130e are offset from the other cuff receptacles. More specifically, cuff receptacles 130a, 130c are generally aligned with one another while cuff receptacle 130b is offset therefrom closer to first end 126b. Similarly, cuff receptacles 130d, 130f are generally aligned with one another while cuff receptacle 130e is offset therefrom closer to second end 128b.

Figure 17C:
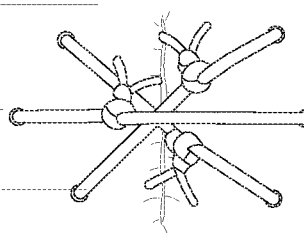

Sutures 134a, 134b, 134c are connected respectively between cuffs 132a and 132f, cuffs 132b and 132e, and cuffs 132c and 132d. When sutures 134a, 134b, 134c are used to close a puncture site PS, sutures 134a, 134b, 134c form a generally star shaped suture pattern around puncture site PS, as shown in FIG. 17C. Sutures 134a, 134b, 134c may also be arranged to form other suture patterns, including three generally parallel suture loops as shown in FIG. 17B.

Figure 4D:
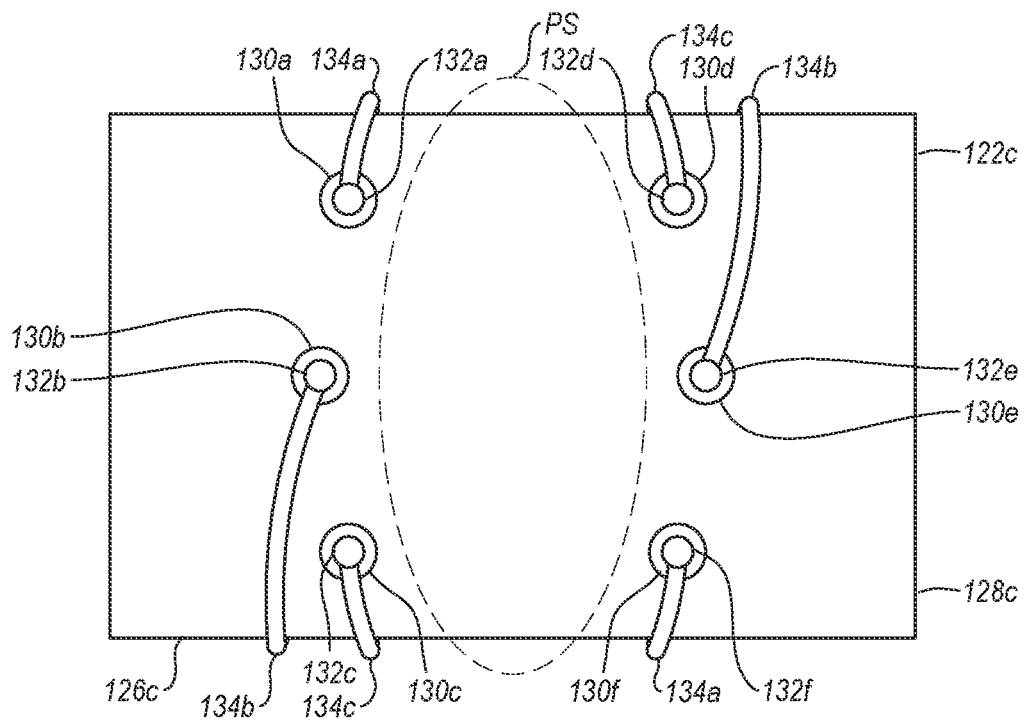
FIG. 4D is a top view of another exemplary foot for use in connection with the closure device of FIG. 1.

FIG. 4D illustrates a foot 122c that is similar to foot 122b in many respects. The main difference between foot 122b and foot 122c is that cuff receptacles 130a-f in foot 122c are arranged in a generally circular pattern. Arranging cuff receptacles 130a-f in a generally circular pattern enables sutures 134a-c to extend across puncture site PS in a number of directions and in a more evenly spaced manner. As with the previous embodiments, sutures 134a-c may be connected between cuffs 132a-f in various combinations or patterns to provide a desired suture pattern for closing puncture site PS.

Figure 4E:
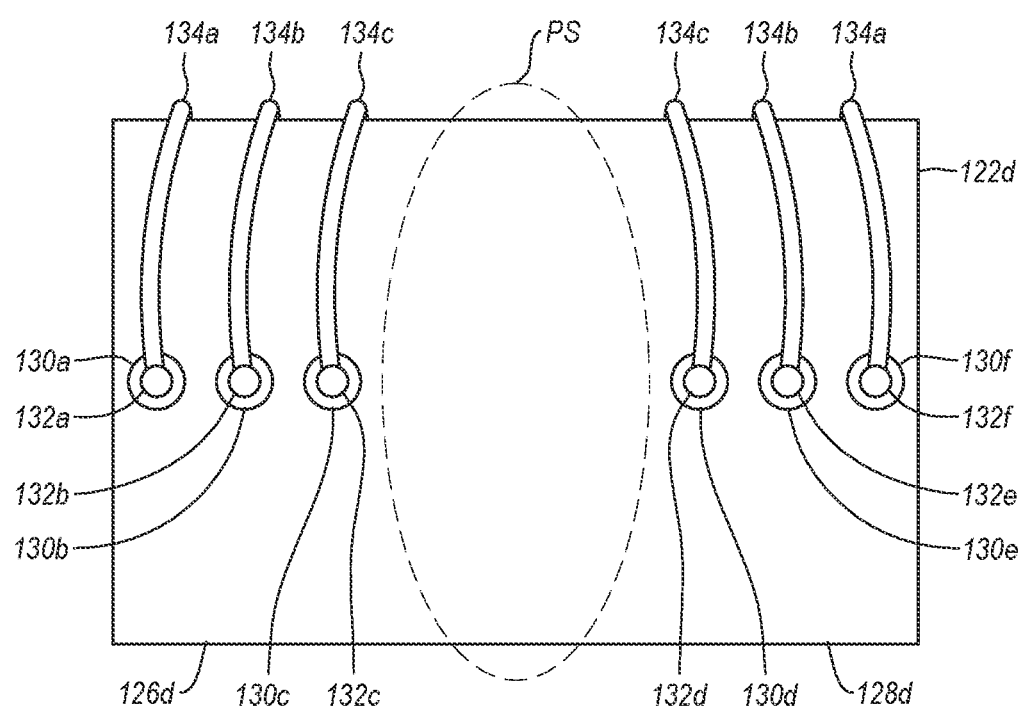
FIG. 4E is a top view of another exemplary foot for use in connection with the closure device of FIG. 1.

FIG. 4E illustrates a foot 122d according to yet another exemplary embodiment of the present invention. As can be seen, foot 122d includes six cuff receptacles 130a-f, and supports six cuffs 132a-f and three sutures 134a-c. In this embodiment, cuff receptacles 130a-f and cuffs 132a-f are all substantially aligned with one another, with sutures 134a-c connected between cuffs 132a-f.

As mentioned above, closure device 100 also includes one or more needles 142 that can be deployed from one or more lumens (such as needle lumens 140) in elongate body 106 and into a patient. The one or more needles 142 can be advanced through needle lumens 140 and into the patient using plunger 116. More specifically, plunger 116 may be linked to or operably associated with the one or more needles 142 such that the one or more needles 142 advance out of needle lumens 140 and into the patient as plunger 116 is moved distally (i.e., towards distal end 104). Likewise, plunger 116 may be adapted to withdraw the one or more needles 142 out of the patient and back into needle lumens 140 when plunger 116 is moved proximally (i.e., away from distal end 104).

Figure 5A:
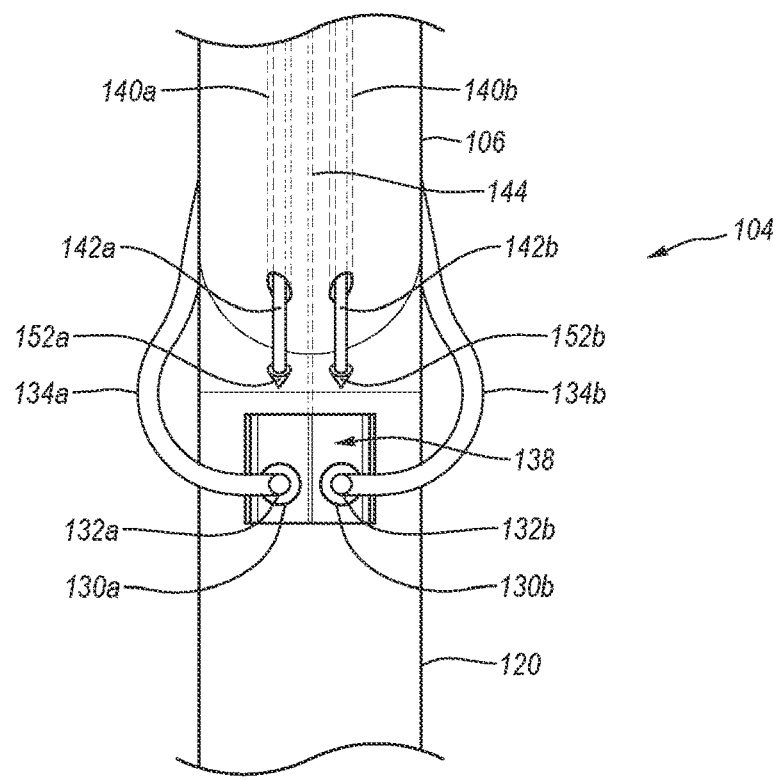
FIG. 5A is a top view of the front side of the distal end of the closure device of FIG. 1, showing needles being deployed toward a first end of the foot.
Figure 5B:
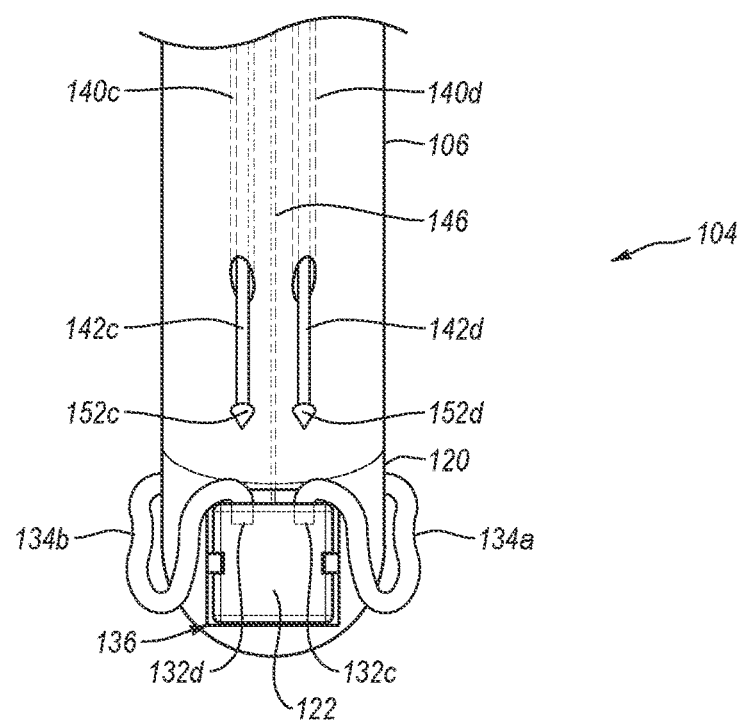
FIG. 5B is an elevation view of the back side of the distal end of the closure device of FIG. 1, showing needles being deployed toward a second end of the foot.

Attention is now directed to FIGS. 5A and 5B, in which FIG. 5A is a top view of the front of distal end 104, and FIG. 5B is an elevation view of the back side of distal end 104. When foot 122 is in the deployed position within a vessel, needles 142 are deployed from elongate member 106 into the patient. As needles 142 penetrate a lumen wall, each needle 142 engages and connects to a cuff 132. Once needles 142 are connected to cuffs 132, the needles and connected cuffs are withdrawn out of the patient. Drawing cuffs 132 out of the patient pulls sutures 134 through the lumen wall so that sutures 134 may be tied to close a puncture in the lumen wall.

FIGS. 5A and 5B depict four needles 142 being deployed or extended out of elongate member 106 toward cuffs 132. In particular, on the front side of distal end 104 needles 142a, 142b extend from needle lumens 140a, 140b, respectively, toward cuffs 132a, 132b, respectively. Similarly, on the back side of distal end 104 needles 142c, 142d extend from needle lumens 140c, 140d, respectively, toward cuffs 132c, 132d, respectively. As needles 142a-d advance, needle tips 152a-d engage and connect to cuffs 132a-d, respectively. Needle tips 152a-d and cuffs 132a-d may include complementary features that allow for a secure connection therebetween. Alternatively, needle tips 152a-d and cuffs 132a-d may connect to one another via a friction-fit, or other means.

Similar to and in connection with the discussion of FIGS. 4A-4E, it will be appreciated that device 100 may include different numbers of needle lumens 140 and needles 142. For instance, if foot 122 supports four cuffs, like in FIG. 4A, then device 100 may be designed with four needle lumens and four needles, as shown in FIGS. 5A and 5B. Alternatively, if foot 122 supports six cuffs as shown in FIGS. 4B-4E, device 100 may include six needle lumens and six needles. Thus, device 100 may have a corresponding number of cuffs, needles, and needle lumens.

Although device 100 may have a corresponding number of cuffs, needles, and needle lumens as discussed above, device 100 may also include non-corresponding numbers of cuffs, needles, and needle lumens. For instance, device 100 may include one or more needles that are configured to retrieve or withdraw through a lumen wall more than one cuff as described herein.

Figure 6:
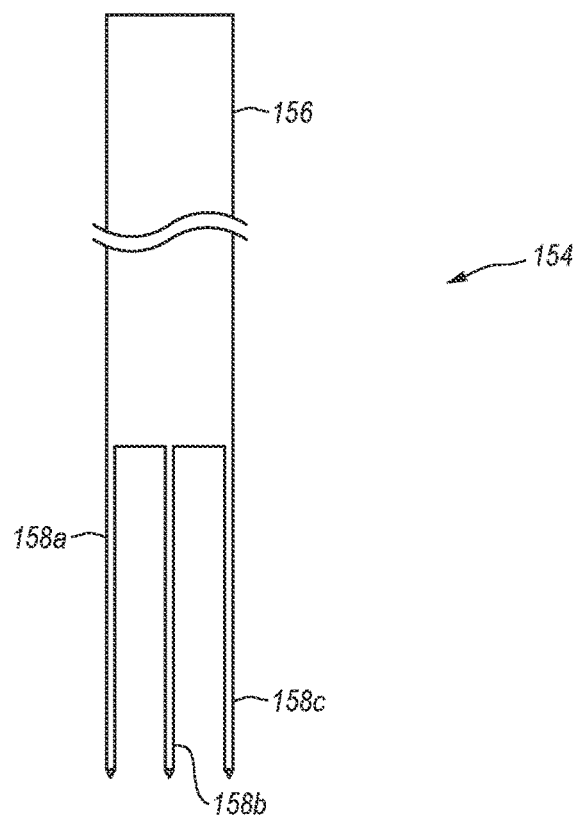
FIG. 6 is an elevation view of an exemplary needle for use in connection with a closure device similar to the closure device of FIG. 1.
Figure 6A:
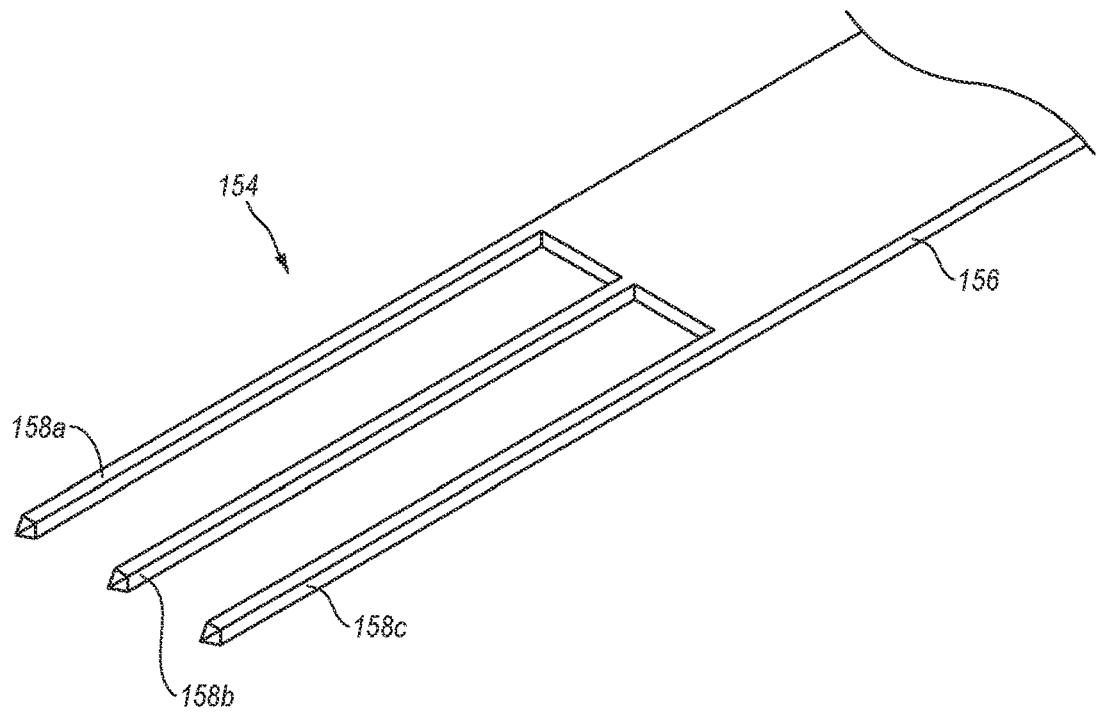
FIG. 6A is a close-up view of a distal end of the needle of FIG. 6.

For instance, FIGS. 6 and 6A illustrate a needle 154 that may be used to simultaneously retrieve multiple cuffs 132. FIG. 6 illustrates an elevation view of needle 154 while FIG. 6A illustrates a close-up perspective view of the distal end of needle 154. As depicted in the Figures, needle 154 includes a shaft 156 and three needle tips 158a, 158b, 158c extending from the distal end of shaft 156. Shaft 156 has a generally rectangular cross-sectional shape and needle tips 158a, 158b, 158c are generally aligned with one another.

Each needle tip 158a, 158b, 158c is configured to engage and connect to a cuff 132 supported by foot 122. Needle tips 158a, 158b, 158c and cuffs 132 may include complementary features that allow for a secure connection therebetween. As depicted in FIG. 6A, each needle tip 158a, 158b, 158c has a generally square cross-sectional shape that can create a friction-based connection with a cuff 132 when needle tips 158a, 158b, 158c are received within cuffs 132. Needle tips 158a, 158b, 158c may have other cross-sectional shapes, including circular, oval, or other regular or irregular shapes.

Although needle 154 is depicted as being generally flat with three needle tips, it will be appreciated that a multi-tip needle according to the present invention may have other configurations. Accordingly, a multi-tip needle may include a plurality of needle tips, including two needle tips or more than three needle tips. Additionally, a multi-tip needle may have a cross-sectional shape that is different from the generally rectangular shape illustrated. For instance, shaft 156 may have a circularly, square, oval, or other cross-sectional shape.

In one embodiment, for example, shaft 156 has a generally V-shaped cross-sectional shape. That is, the opposing sides of shaft 156 are generally aligned with one another while the center portion of shaft 156 is offset from the opposing sides. As a result of this cross-sectional shape of shaft 156, needle tip 158b may be offset from needle tips 158a and 158c. Needle tips 158a, 158b, 158c may also be offset from one another when shaft 156 has other cross-sectional shapes.

Using multi-tip needles, such as needle 154, can reduce the number of needle lumens required in elongate member 106. For instance, two needles 154 (each having three needle tips 158a, 158b, 158c) can be advanced from two needle lumens to retrieve six cuffs rather than advancing six individual needles through six different needle lumens. Forming elongate member 106 with fewer needle lumens can simplify the manufacturing of elongate member 106.

Figure 7A:
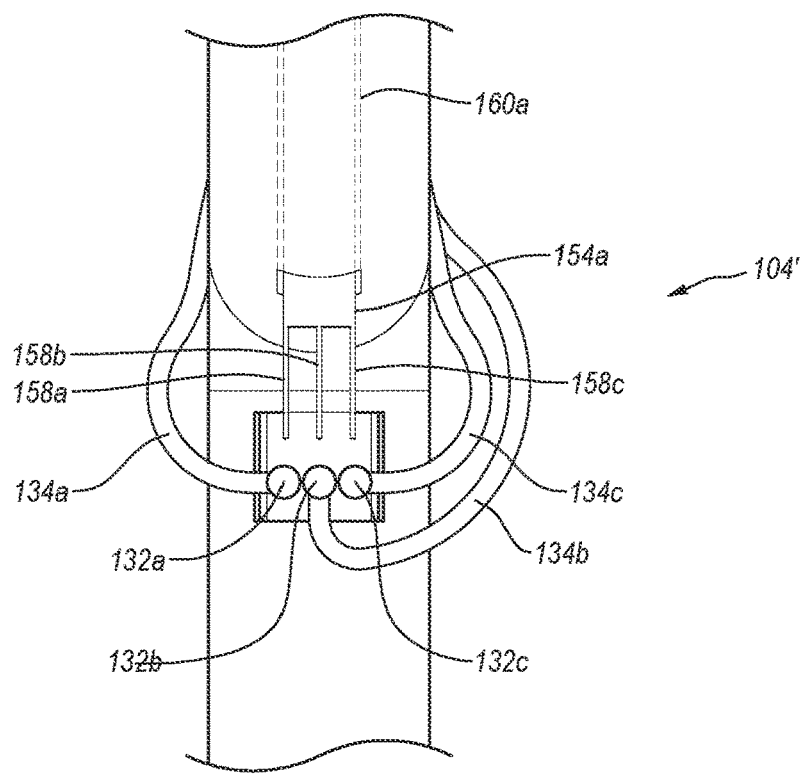
FIG. 7A is a top view of the front side of the distal end of a closure device similar to the closure device of FIG. 1, showing a needle from FIG. 6A being deployed toward a first end of the foot.
Figure 7B:
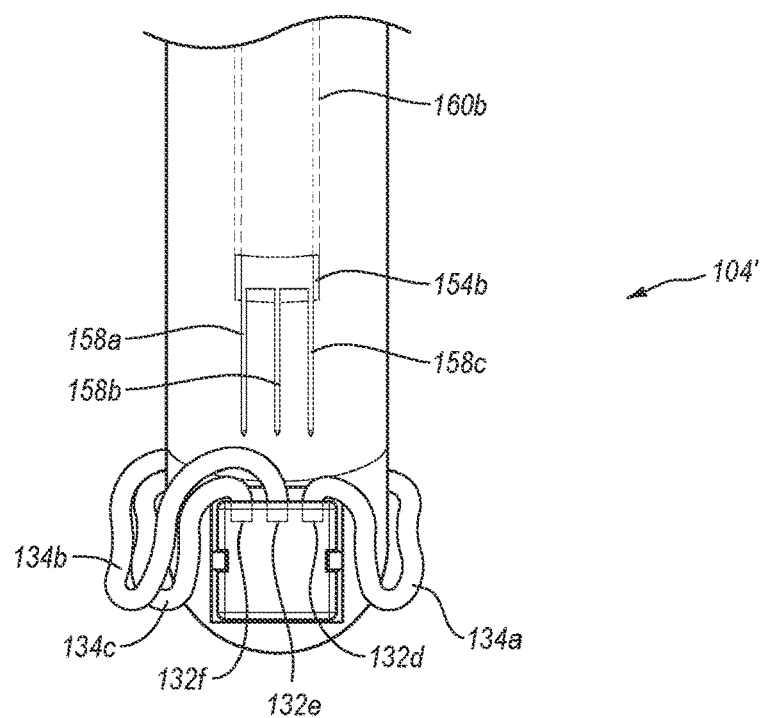
FIG. 7B is an elevation view of the back side of the distal end of a closure device similar to the closure device of FIG. 1, showing a needle from FIG. 6A being deployed toward a second end of the foot.

FIGS. 7A and 7B illustrate views similar to those of FIGS. 5A and 5B. More specifically, FIGS. 7A and 7B illustrate front and back views of a distal end 104' that is similar in many respects to distal end 104. In contrast to FIGS. 5A and 5B, which illustrate four separate needles being advanced from four separate needle lumens, FIGS. 7A and 7B illustrate two multi-tip needles 154 being advanced from two needle lumens 160a, 160b.

In particular, on the front side of distal end 104', needle 154a extends from needle lumen 160a so that needle tips 158a, 158b, 158c from needle 154a extend toward cuffs 132a, 132b, 132c, respectively, as shown in FIG. 7A. Similarly, as shown in FIG. 7B, on the back side of distal end 104', needle 154b extends from needle lumen 160b so that needle tips 158a, 158b, 158c from needle 154b extend toward cuffs 132d, 132e, 132f, respectively. As needles 154a, 154b advance, needle tips 158a-c from needle 154a engage and connect to cuffs 132a-c, respectively, and needle tips 158a-c from needle 154b engage and connect to cuffs 132d-f, respectively. Once the needle tips are connected to cuffs 132a-f, needles 154a, 154b can be withdrawn proximally to draw cuffs 132a-f through the lumen wall, thereby pulling the ends of sutures 134a-c through the lumen wall. With the ends of sutures 134a-c pulled through the lumen wall, distal end 104' can be removed from the body lumen and sutures 134a-c can be tied to close a puncture site in the lumen wall.

With reference now to FIGS. 8-12, one exemplary method of using device 100 will be discussed. In light of the foregoing discussion, it will be understood that device 100, as used in the following method, may include a plurality of individual needles (e.g., needles 142) delivered through individual needle lumens (e.g., 140), or may include one or more multi-tip needles (e.g., needles 154) delivered through one or more needle lumens (e.g., 160). For simplicity, the following exemplary method will be described with reference to needles 162a, 162b and needle lumens 164a, 164b. Nevertheless, it will be appreciated that needles 162a, 162b may be representative of two or more individual-tip or multi-tip needles. Likewise, needle lumens 164a, 164b may also be representative of two or more needle lumens through which individual-tip or multi-tip needles can be advanced.

Figure 8:
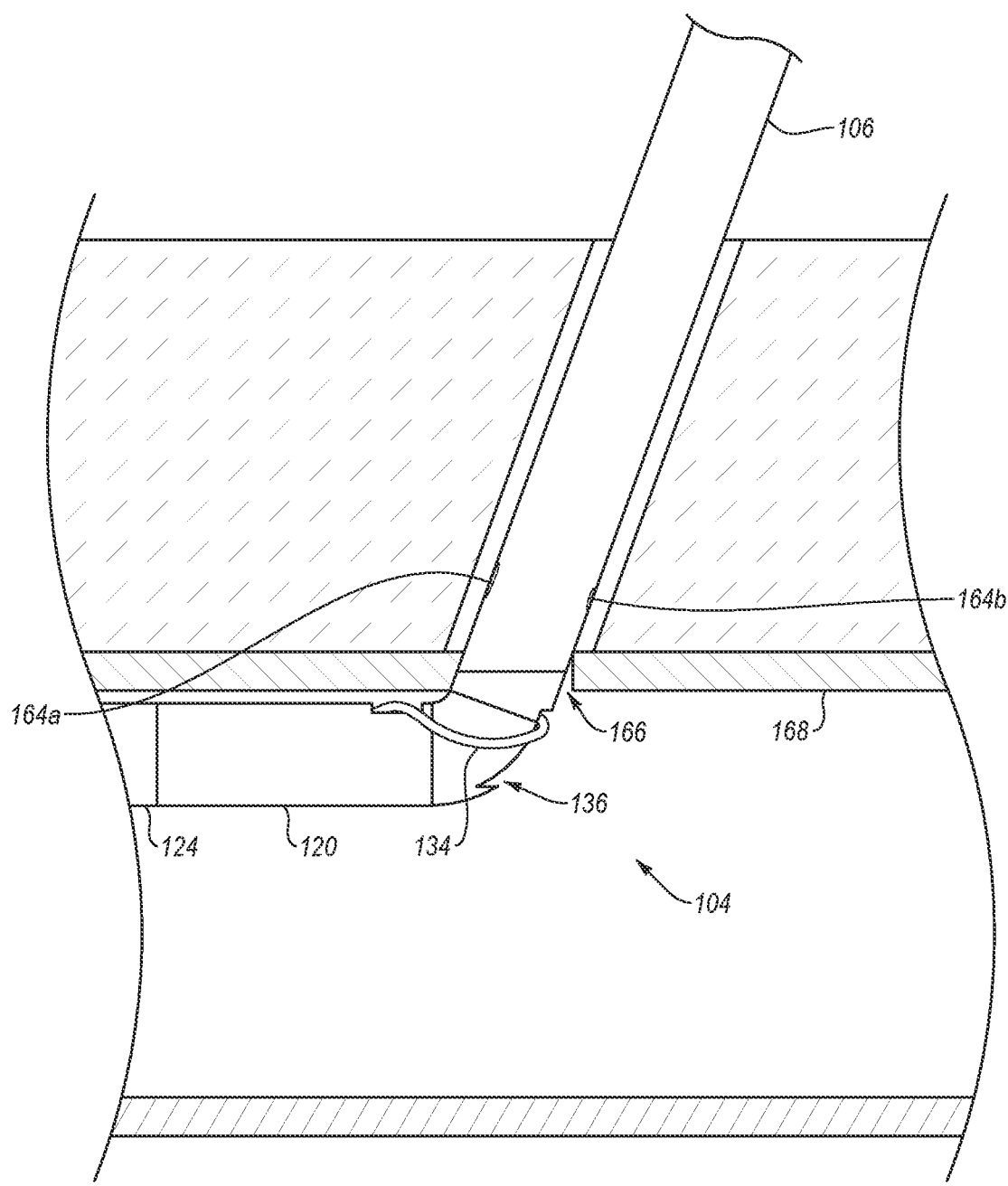
FIG. 8 is a close-up, side view of the distal end of the closure device of FIG. 1 inserted into a vessel through a puncture site.
Figure 9:
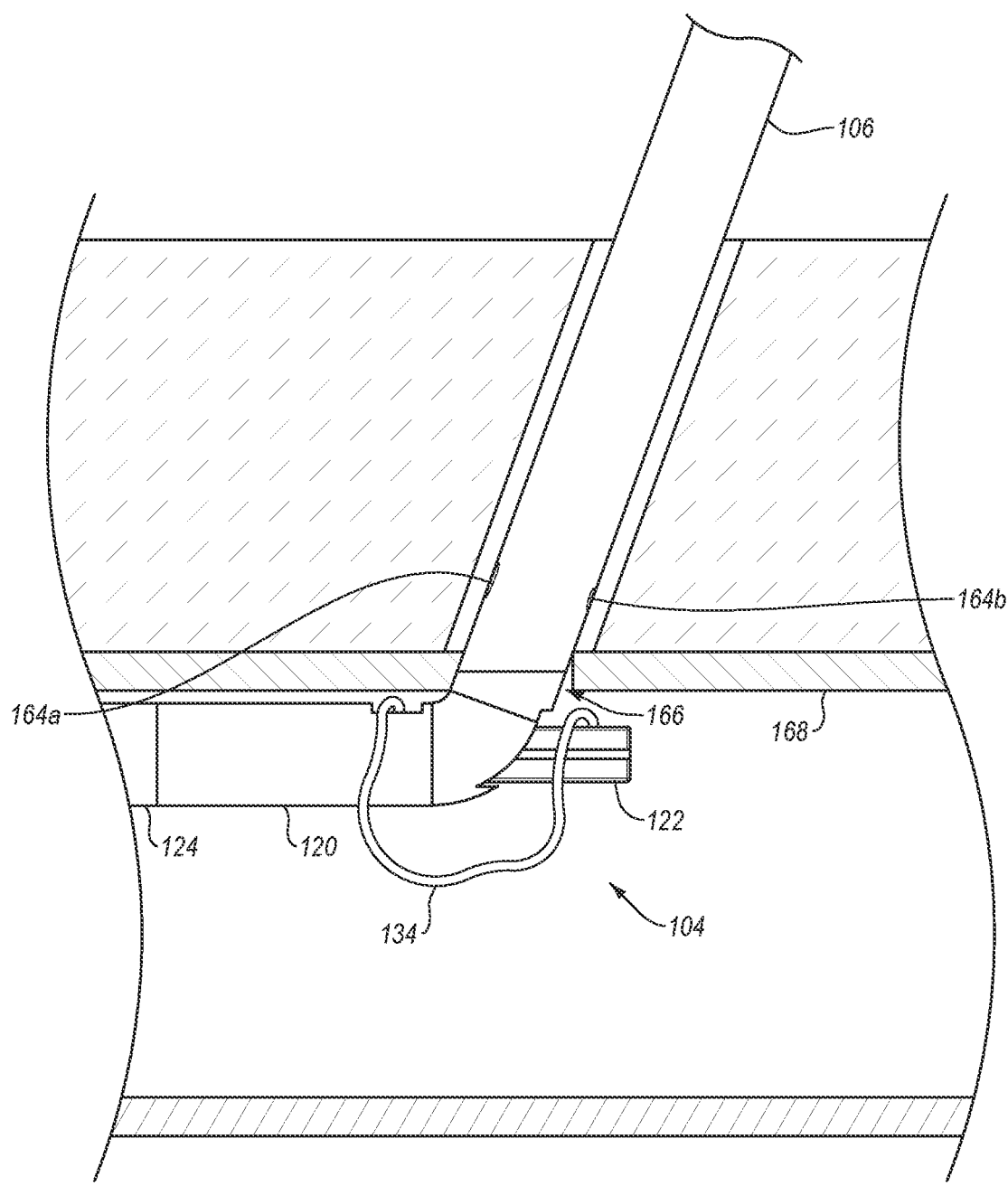
FIG. 9 is a view similar to FIG. 8, except that the foot of the distal end has been deployed or expanded within the vessel.

As shown in FIG. 8, distal end 104 of device 100 is at least partially inserted into a patient such that foot portion 120 passes through a puncture site 166 in a lumen wall 168. As with many transluminal procedures, device 100 may be introduced into the body lumen using a guidewire. Once foot portion 120 is positioned within the body lumen, foot 122 is moved to the deployed position as shown in FIG. 9. As discussed above, foot 122 may be moved to the deployed position by actuating lever 118. Once foot 122 is in the deployed position, device 100 may be moved proximally so that foot portion 120 and foot 122 engage the interior surface of lumen wall 168. In this manner foot portion 120 and foot 122 may be used as locators to ensure proper placement of distal end 104 within the body lumen.

Figure 10:
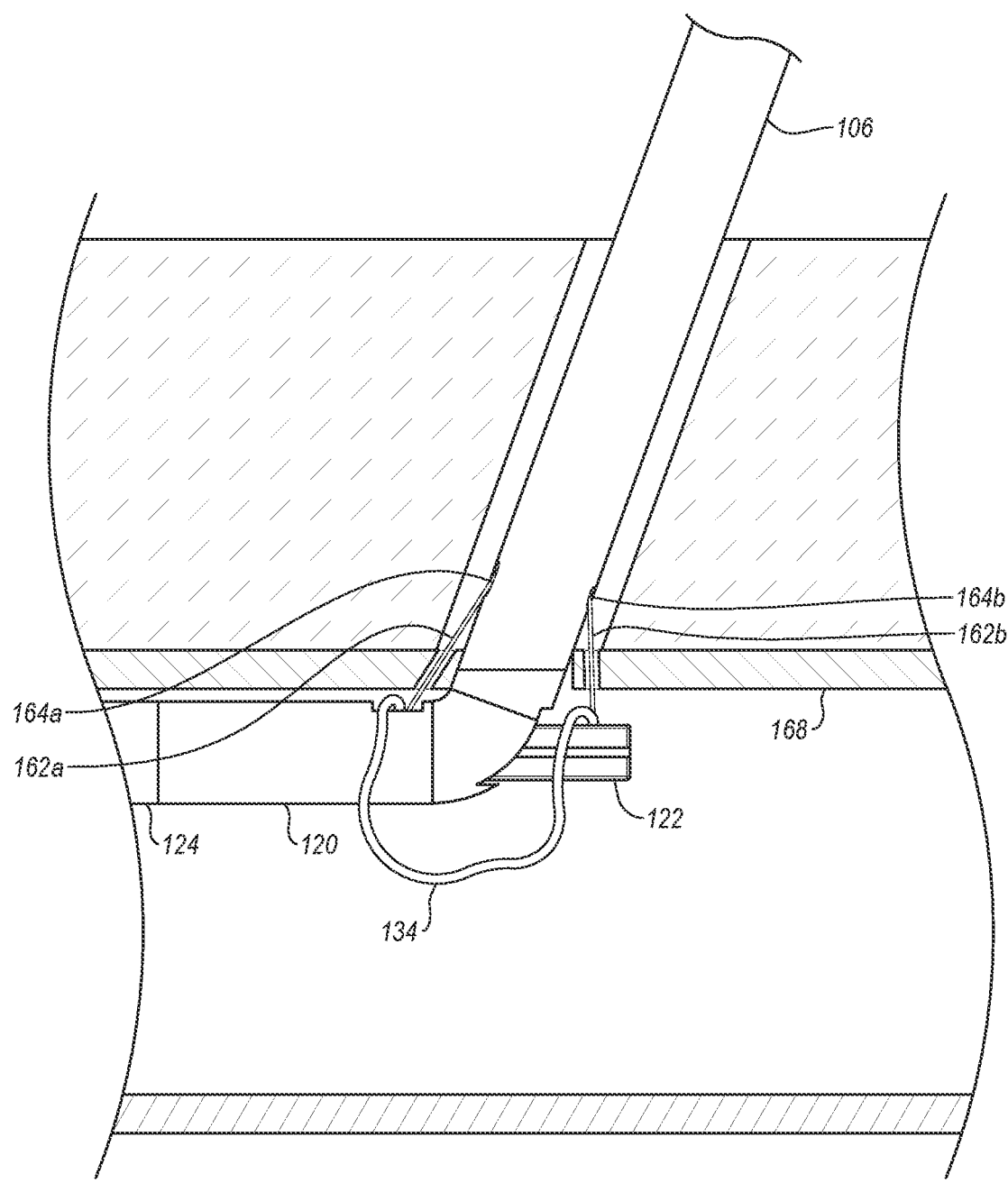
FIG. 10 is a view similar to FIG. 9, except that needles have been deployed through the vessel wall and into cuffs mounted on the foot.

Once foot 122 has been deployed and positioned within the body lumen as desired, needles 162a, 162b are advanced from needle lumens 164a, 164b as shown in FIG. 10. As discussed above, needles 162a, 162b may be advanced out of needle lumens 164a, 164b by moving plunger 116 (FIG. 1) distally. The advancement of needles 162a, 162b out of needle lumens 164a, 164b causes needles 162a, 162b to extend distally and at least partially radially away from elongate member 106. More specifically, as shown in FIG. 10, needles 162a, 162b extend out of needle lumens 164a, 164b at an angle relative to elongate member 106 so that needles 162a, 162b will pass through lumen wall 168 and to cuffs 132 in foot 122 upon advancement of needles 162a, 162b out of needle lumens 164a, 164b.

Figure 11:
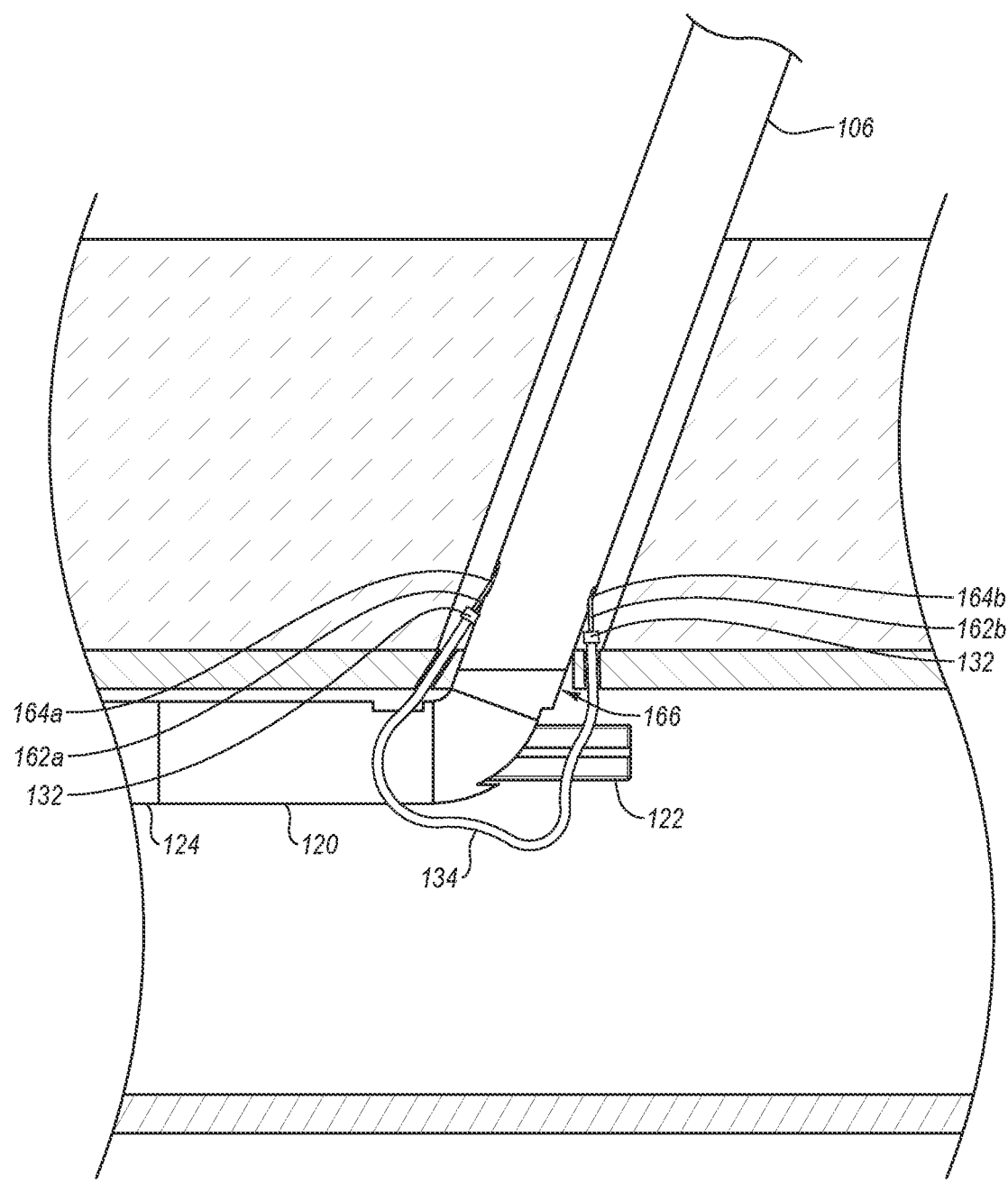
FIG. 11 is a view similar to FIG. 10, except that the needles have been drawn proximally, thereby drawing the cuffs and attached sutures through the vessel wall.

As needles 162a, 162b engage cuffs 132 in foot 122, the needle tips of needles 162a, 162b (whether single tip or multi-tip needles) securely engage cuffs 132 to connect cuffs 132 to needles 162a, 162b. With the needle tips securely connected to cuffs 132, needles 162a, 162b are withdrawn out of the patient by moving plunger 116 (FIG. 1) proximally. As needles 162a, 162b are withdrawn, cuffs 132 are also withdrawn out of the patient. More specifically, since cuffs 132 are securely connected to needles 162a, 162b, withdrawal of needles 162a, 162b also causes cuffs 132 to be withdrawn. Even more specifically, as shown in FIG. 11, as needles 162a, 162b are drawn back through lumen wall 168, cuffs 132 are likewise drawn therethrough. As can also be seen in FIG. 11, since suture 134 is connected between cuffs 132, the ends of suture 134 are also drawn through lumen wall 168. As a result, the opposing ends of suture 134 extend through lumen wall 168 on opposing sides of puncture site 166 so that suture 134 spans puncture site 166.

Figure 12:
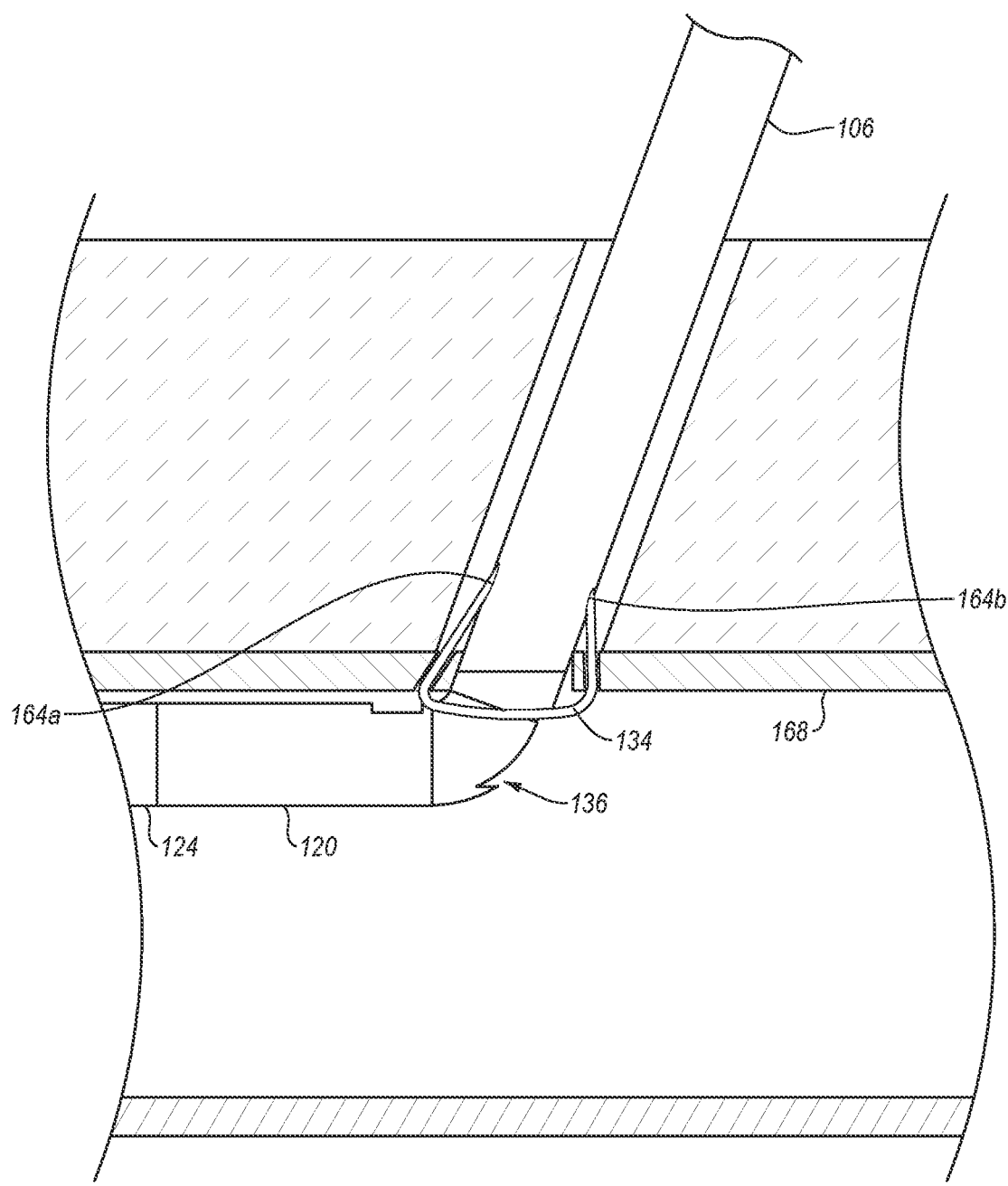
FIG. 12 illustrates the needles completely withdrawn into the elongate member and the foot withdrawn back into the delivery position prior to removal of the distal end from the vessel.

Needles 162a, 162b may be withdrawn completely back into needle lumens 164a, 164b along with cuffs 132 as shown in FIG. 12. Foot 122 is then moved back to the delivery position as also shown in FIG. 12. As discussed above, foot 122 is moved from the deployed position to the delivery position by moving lever 118 from the position shown in FIG. 2 to the position shown in FIG. 1. Once foot 122 is in the delivery position, distal end 104 is removed from the patient, leaving sutures 134 spanning puncture site 166 and extending out of lumen wall 168. Sutures 134 may then be secured together to close puncture site 166.

Figure 14:
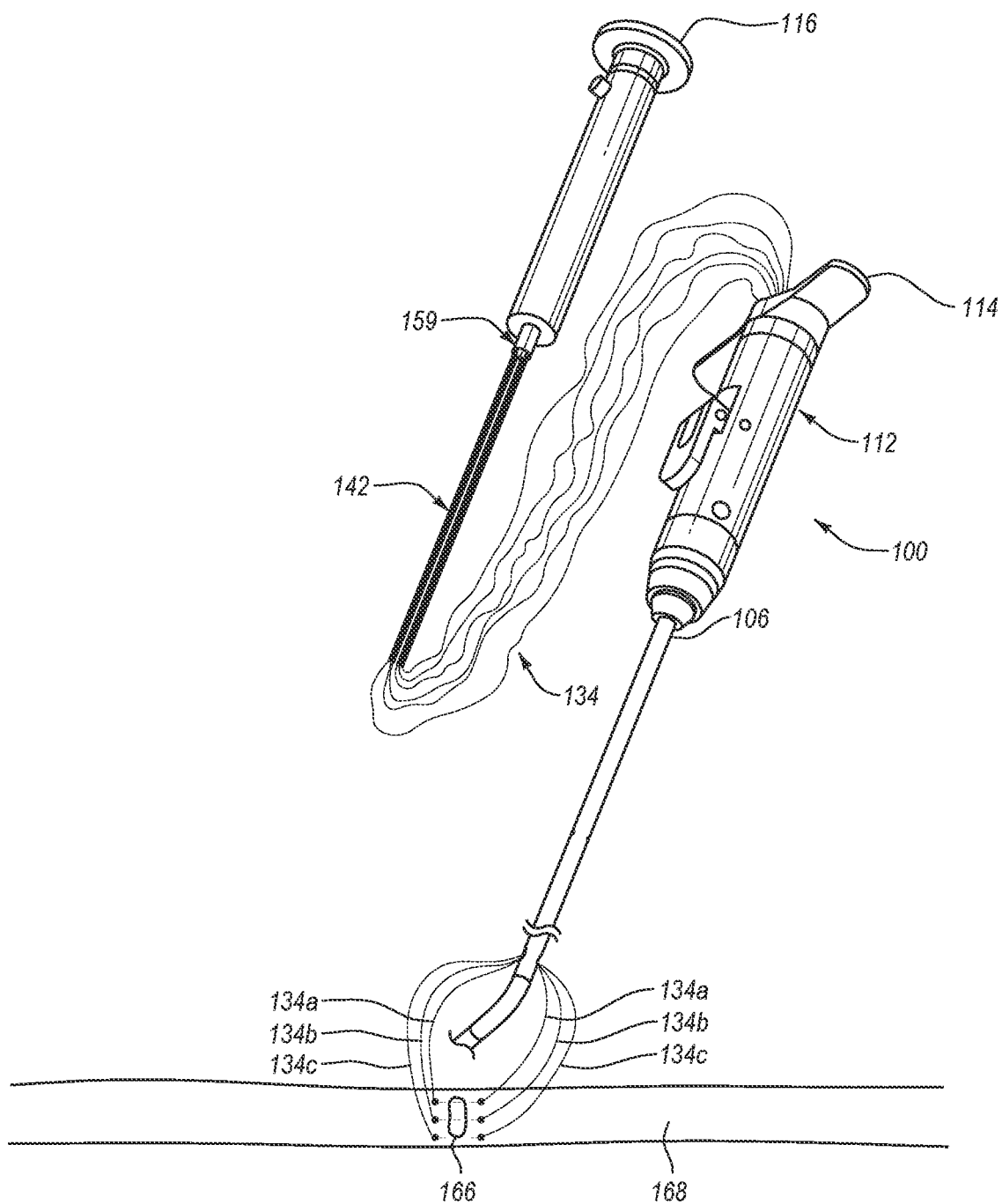
FIG. 14 illustrates a plunger and the needles withdrawn from the device.
Figure 15:
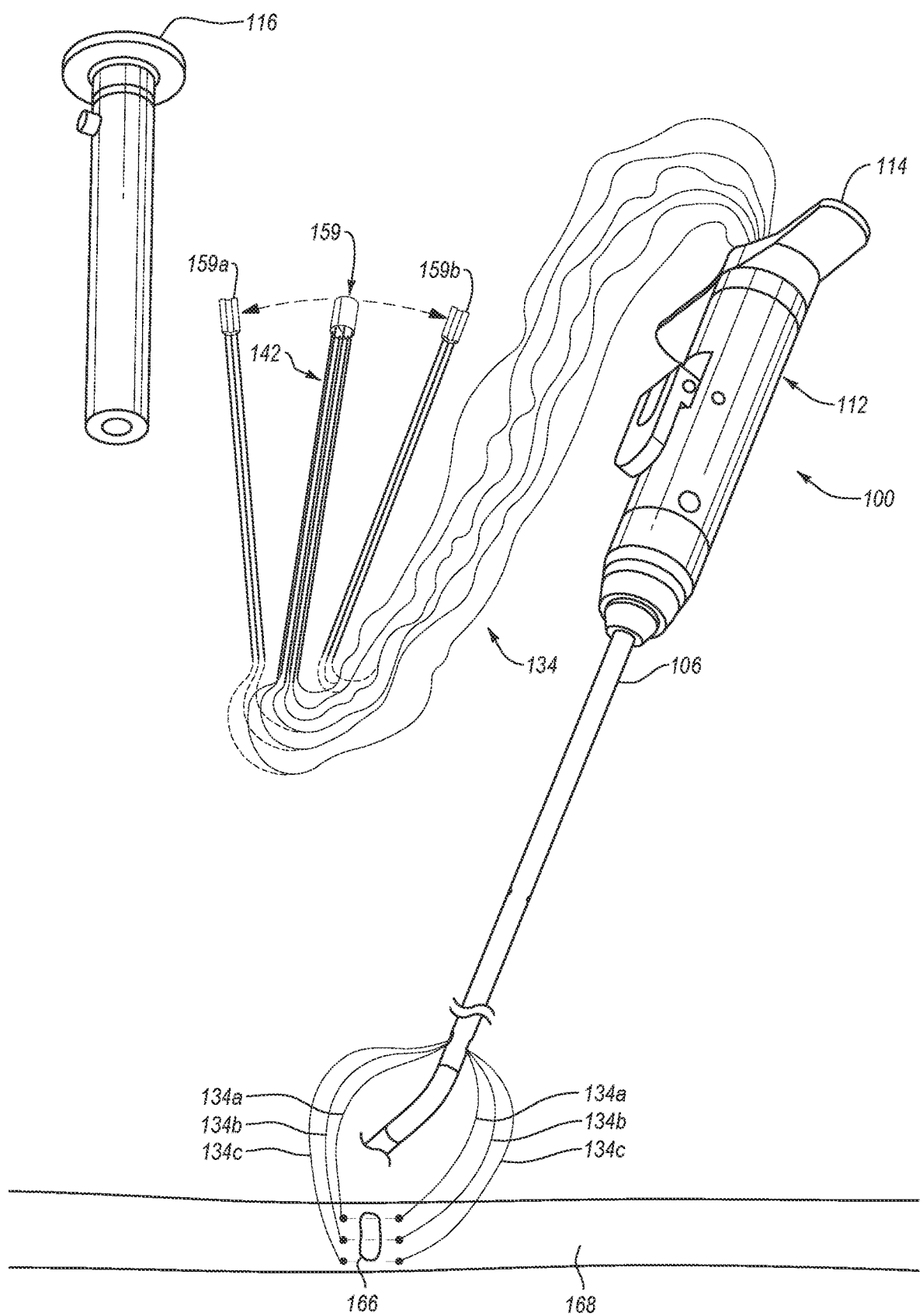
FIG. 15 illustrates a needle housing detached from the plunger and, in phantom, separated into two halves.
Figure 16:
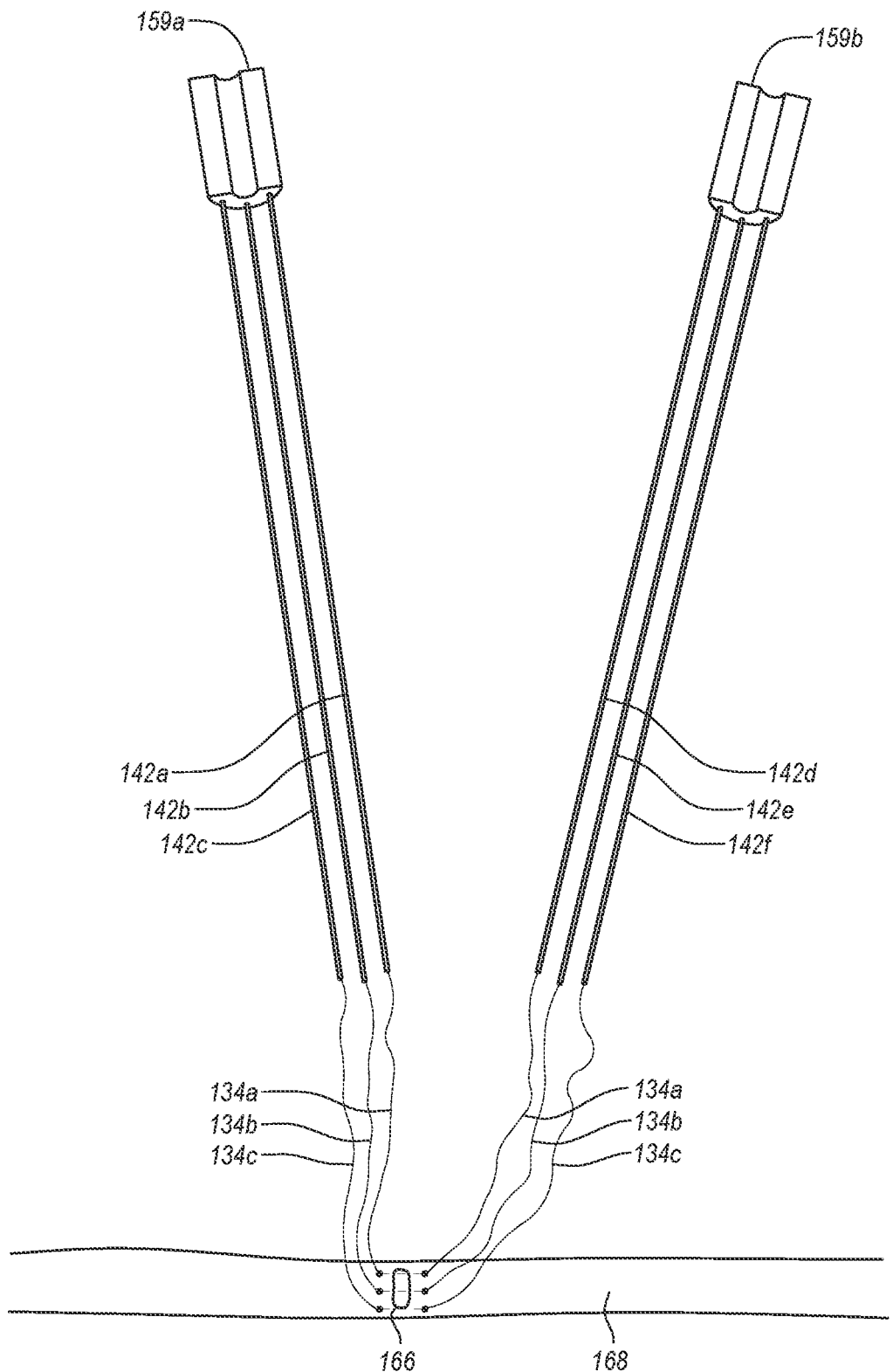
FIG. 16 illustrates the sutures, needles, and needle housing halves freed from the closure device.

FIGS. 13-16 illustrate an exemplary manner of removing distal end 104 and closing puncture site 166. The illustrated embodiment uses two or more sutures 134 to close puncture site 166. As discussed above, each suture 134 may be connected between two separate needles 142 or individual needle tips (e.g., 158) on separate multi-tip needles (e.g., 154). In the illustrated embodiment, for instance, three sutures 134a-134c are connected between six needles 142a-142f. Specifically, as best seen in FIG. 16, suture 134a is connected between needles 142a and 142d, suture 134b is connected between needles 142b and 142e, and suture 134c is connected between needles 142c and 142f.

Figure 13:
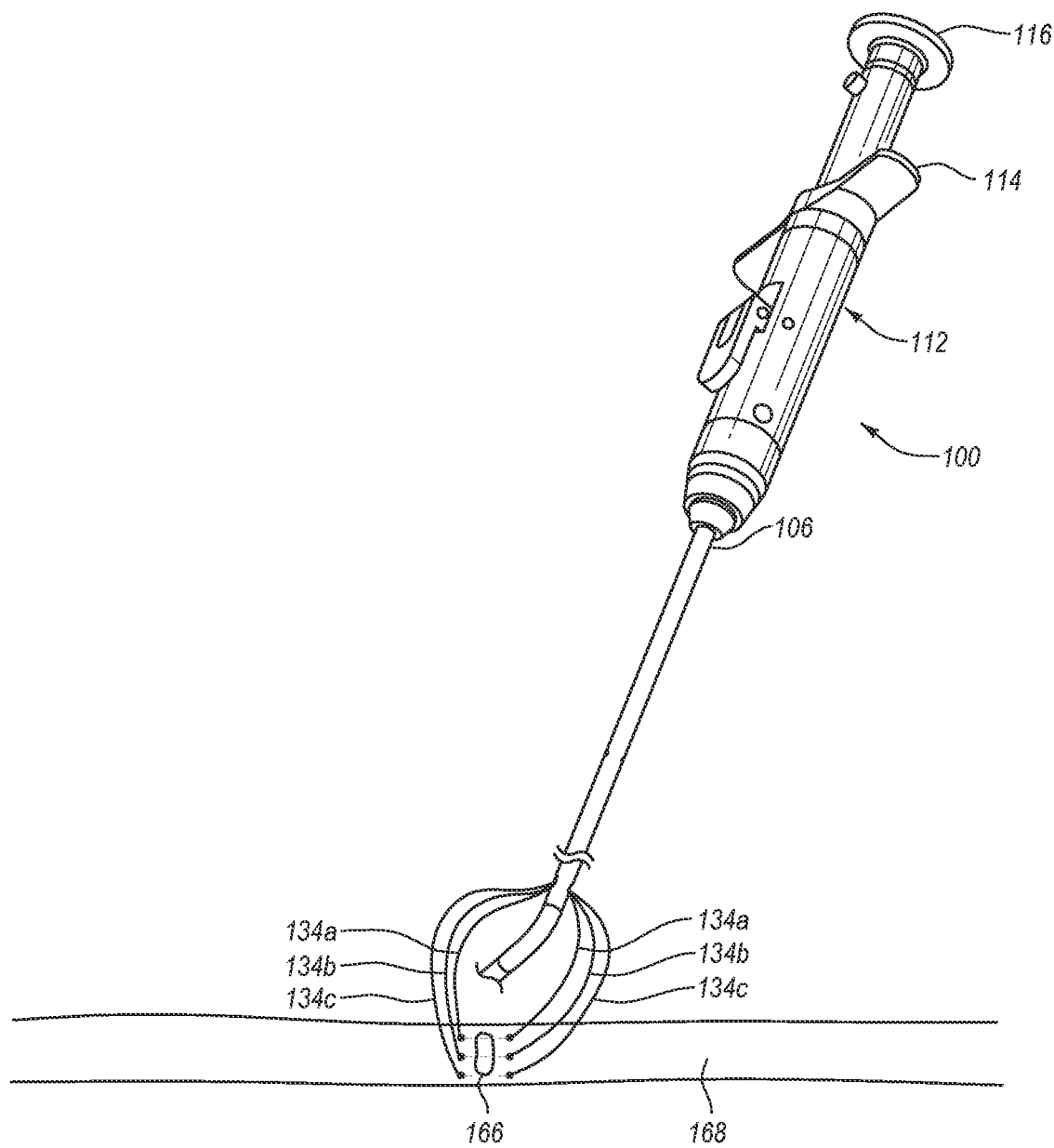
FIG. 13 illustrates the distal end of the device removed from the vessel after the sutures have been drawn through the vessel wall.

Once needles 142a-142f have been deployed and withdrawn to draw the ends of sutures 134a-134c through lumen wall 168 as discussed above in connection with FIGS. 8-12, distal end 104 may be removed from the patient as shown in FIG. 13. Plunger 116 may then be removed from actuator mechanism 112 as shown in FIG. 14. More specifically, plunger 116 may be drawn proximally relative to actuator 112 until plunger 116 is removed from the proximal end of actuator mechanism 112.

As can be seen in FIG. 14, a detachable needle housing 159 is disposed on the distal end of plunger 116. Housing 159 may hold the proximal ends of needles 142 such that movement of plunger 116 causes a corresponding movement of needles 142. Accordingly, removal of plunger 116 from actuator mechanism 112 may likewise cause needles 142 to be at least partially withdrawn proximally from actuator mechanism 112. FIG. 14 illustrates needles 142 completely withdrawn from actuator mechanism 112.

As shown in FIG. 15, needle housing 159 may be detached from plunger 116 to facilitate the removal of closure device 100 from off of sutures 134. After detaching needle housing 159 from plunger 116, needle housing 159 may be separated into two halves 159a, 159b, as shown in phantom lines in FIG. 15. In the illustrated embodiment, half 159a holds the proximal ends of needles 142a-142c and half 159b holds the proximal ends of needles 142d-142f.

With needle housing 159 detached from plunger 116 and separated into halves 159a, 159b, halves 159a, 159b, with their associated needles 142 and attached sutures 134, may be passed through actuator mechanism 112 and elongate member 106 so as to free sutures 134, needles 142, and halves 159a, 159b from closure device 100. More specifically, half 159a and its associated needles 142 may be passed distally back through actuator mechanism 112 and the needle lumen 140 associated with the needles 142 of half 159a so that half 159a and its needles 142 exit the distal end of needle lumen 140, thereby freeing half 159a and its needles 142 from device 100. Half 159b and its associated needles 142 may similarly be passed back through actuator mechanism 112 and the needle lumen 140 associated with the needles 142 of half 159b so that half 159b and its needles 142 exit the distal end of needle lumen 140 associated therewith, thereby freeing half 159b and its needles 142 from device 100.

Alternatively, closure device 100 may have one or more slots extending the length thereof through which sutures 134 and/or needles 142 may be passed to remove closure device 100 from off of sutures 134. For instance, the slots may open the needle lumens 140 to the external surface of device 100 such that sutures 134 and/or needles 142 may be passed therethrough to remove device 100. In other embodiments, the slots may open the needle lumens 140 to a central internal channel within device 100, such that sutures 134 and needles 142 may be passed from needle lumens 140 into the central channel so that sutures 134, needles 142, and halves 159a, 159b may be passed through the central channel and out the distal end of device 100.

In any case, once closure device 100 has been removed from sutures 134, halves 159a, 159b enable sutures 134a-134c to be arranged in an orderly manner, as shown in FIG. 16, thereby enabling a doctor (or other user) to quickly identify opposing ends of each suture 134. The doctor (or other user) may then cut the opposing ends of each suture from the needles and tie them off individually to close puncture site 166, as shown in FIG. 17. Being able to quickly identify opposing ends of each suture 134 allows the user to better manage the sutures and ensure that puncture site 166 is properly closed. After the sutures have been cut from the needles, the detachable housing may be re-attached to the plunger, or may be disposed.

Depending on the number and arrangement of sutures 134, various closure patterns and knots may be used to close puncture site 166. FIGS. 17A-17C illustrate various example manners of closing puncture site 166. For instance, FIG. 17A illustrates two sutures tied in a parallel arrangement. FIG. 17B illustrates a similar parallel arrangement with three sutures. FIG. 17C illustrates three sutures tied in a star shaped arrangement. Sutures 134 can be secured in any suitable manner, including by tying or with clamps, clips, or other closure devices.

Attention is now directed to FIGS. 18-25 which illustrate a closure device 200 according another exemplary embodiment of the present invention, and a method for using closure device 200. Closure device 200 is similar to closure device 100 in many respects. As a result, the following discussion of closure device 200 will focus primarily on those aspects of closure device 200 that are different from closure device 100.

Closure device 200 includes a proximal end 202 and a distal end 204. As shown in FIGS. 18 and 19, closure device 200 includes an elongate member 206 that has a proximal end 208 and a distal end 210. Elongate member 206 is generally tubular and includes one or more lumens that extend generally from proximal end 208 to distal end 210. The one or more lumens may be used to facilitate the delivery of device 200 over a guidewire or to deliver one or more needles into a patient. As can be seen in FIGS. 18 and 19, elongate member 206 has a generally uniform diameter along its length.

Connected to proximal end 208 of elongate member 206 is an actuator mechanism 212. Actuator mechanism 212 includes a handle 214 to facilitate manipulation of device 200. Actuator mechanism 212 also includes a plunger 216 used to deploy and retract needles from elongate member 206, and a lever 218 used to selectively deploy and retract a plurality of feet.

As shown in FIGS. 18 and 19, distal end 204 of device 200 includes a foot portion 220 attached to or extending from distal end 210 of elongate member 206. Elongate member 206 and foot portion 220 may be discrete pieces that are coupled together, or elongate member 206 and foot portion 220 may be integrally formed as a single piece.

A plurality of feet 222 are movably mounted on foot portion 220. Feet 222 are movable between a delivery position and a deployed position. In the delivery position, which is illustrated in FIG. 18, feet 222 are positioned at a first location along the length of device 200 and are substantially or entirely within a diameter that is about equal to an outer diameter of elongate member 206. In contrast, when feet 222 are in the deployed position as illustrated in FIG. 19, feet 222 are positioned at a second, more proximal location along the length of device 200 and extend radially beyond the outer diameter of elongate member 206.

When feet 222 are in the delivery configuration, distal end 204 can be inserted through a puncture site and into a body lumen of a patient. Once distal end 204 is positioned within the body lumen, feet 222 may be moved to the deployed position. When in the deployed position, feet 222 increase the profile of distal end 204, which prevents distal end 204 from being inadvertently pulled out of the body lumen through the puncture site. Additionally, feet 222 may also be used as a locator to assist a physician in properly positioning distal end 204 within the body lumen. As will be discussed in greater detail below, feet 222 are operatively connected to lever 218 such that feet 222 may be selectively moved between the delivery position and the deployed position by actuating lever 218.

FIGS. 18 and 19 further illustrate that device 200 optionally includes a flexible guidebody 224 extending distally from the distal end of foot portion 220. As with guidebody 124, guide body 224 can be advanced along a guidewire into a body lumen. Accordingly, at least the distal portion of guidebody 224 can be formed from a flexible or elastomeric material that is biocompatible, particularly with blood.

Figure 20A:
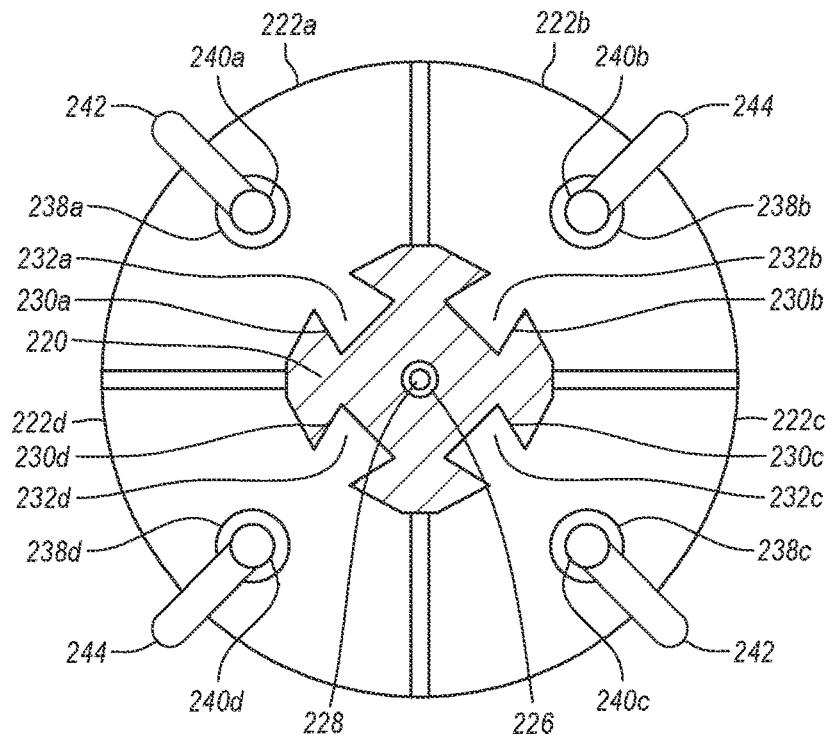
FIG. 20A is a cross-sectional view of the distal end of the closure device of FIG. 18 taken along cutting plane 20A-20A of FIG. 18, showing cuffs mounted within the foot lobes.
Figure 20B:
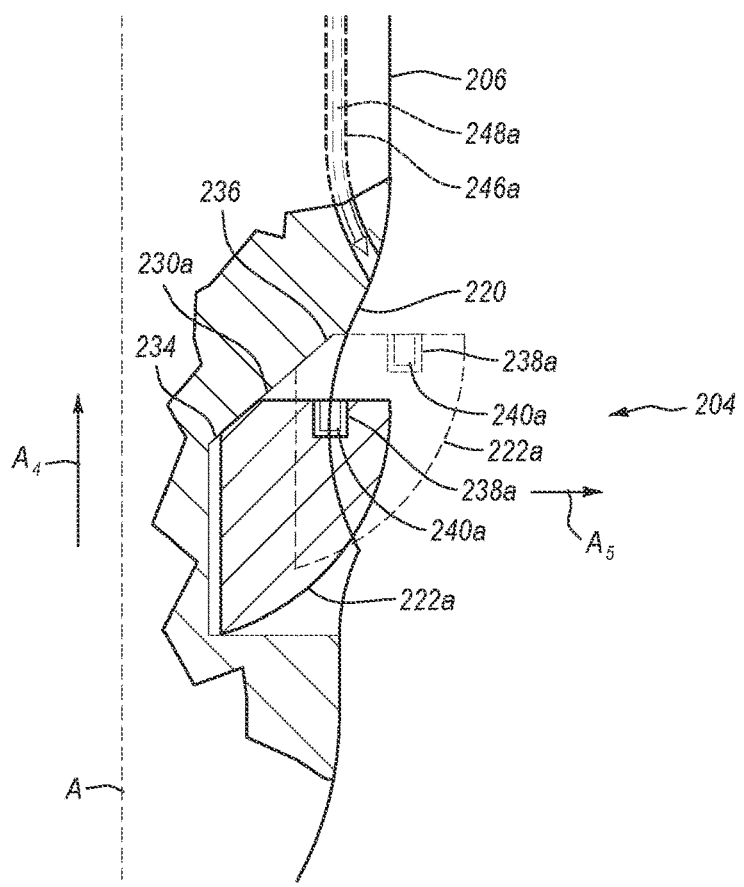
FIG. 20B is a partial cutaway view of the distal end of the closure device of FIG. 18, showing a foot lobe in a delivery position and, in phantom view, in a deployed position.

Turning attention to FIGS. 20A and 20B, a horizontal cross-sectional view (taken along cross-sectional lines 20A-20A in FIG. 18) and a partial cutaway view of distal end 204, including foot portion 220 and plurality of feet 222, are illustrated. In the present embodiment, plurality of feet 222 includes four feet, identified as feet 222a, 222b, 222c, 222d, respectively, but may include more or fewer feet. As can be seen in FIG. 20A, feet 222a-d are disposed radially about foot portion 220. Extending through the center of foot portion 220 is an actuator lumen 226, which also extends at least partially through elongate body 206. A rod or cable 228 extends through actuator lumen 226 to connect feet 222a-d to lever 218.

As lever 218 is moved in the direction of arrow $A_3$, as shown in FIG. 19, rod 228 is drawn proximally through actuator lumen 226. The proximal movement of rod 228 causes feet 222a-d to move from the delivery position shown in FIG. 18 to the deployed position shown in FIG. 19. In contrast, as lever 218 is moved in the direction opposite to arrow $A_3$, rod 228 is moved distally through actuator lumen 226, thereby moving feet 222a-d from the deployed position to the delivery position.

FIG. 20B illustrates a cutaway view of distal end 204, showing foot 222a in the delivery and deployed positions. Specifically, FIG. 20B shows foot 222a in solid lines in the delivery position and in phantom lines in the deployed position. As can be seen in FIG. 20B, when in the delivery position, foot 222a is located more distally along the length of distal end 204 than when foot 222a is in the deployed position. In other words, as foot 222a moves from the delivery position to the deployed position (e.g., generally in the direction of arrow $A_4$), foot 222a moves proximally along the length of distal end 204. Correspondingly, as foot 222a moves from the deployed position to the delivery position (e.g., generally in the direction opposite to arrow $A_4$), foot 222a moves distally along the length of distal end 204.

Likewise, when in the delivery position, foot 222a is located radially closer to the center of foot portion 220 (e.g., actuator lumen 226) than when foot 222a is in the deployed position. In other words, as foot 222a moves from the delivery position to the deployed position, foot 222a moves radially away from the center of foot portion 220. Correspondingly, as foot 222a moves from the deployed position to the delivery position, foot 222a moves radially closer to the center of distal end 204.

To facilitate movement of feet 222a-d between the delivery and deployed positions, foot portion 220 and feet 222a-d include a track system. The track system enables feet 222a-d to move along the length of device 200 while also moving radially relative to foot portion 220. In the illustrated embodiment, foot portion 220 includes track guides 230a-d disposed within the outer surface thereof, and feet 222a-d include tracks 232a-d, respectively. Tracks 232a-d are slidably positioned within track guides 230a-d, respectively, so that tracks 232a-d are able to slide within track guides 230a-d as feet 222a-d move between the delivery and deployed positions.

As noted above, FIG. 20B illustrates a partial cutaway view of distal end 204. More specifically, FIG. 20B illustrates a partial cutaway view of distal end 204 showing foot 222a in solid lines in the delivery position and in phantom lines in the deployed position. FIG. 20B also shows that track guide 230a is angled relative to the length of device 200 and/or a central or longitudinal axis A of distal end 204. That is, track guide 230a has a first or distal end 234 that is positioned radially closer to central axis A than a second or proximal end 236.

The angled nature of track guide 230a causes foot 222a to move radially closer to and further away from axis A as foot 222a moves along the length of device 200. For instance, as rod 228 pulls foot 222a in the direction of arrow $A_4$, the angled nature of track guide 230a causes foot 222a to also move in the direction of arrow $A_5$. Similarly, as rod 228 pushes foot 222a in the direction opposite of arrow $A_4$, the angled nature of track guide 230a causes foot 222a to also move in the direction opposite of arrow $A_5$. As a result, foot 222a is able to move both longitudinally along a portion of the length of device 200 as well as radially relative to foot portion 220.

Although FIG. 20B only illustrates track guide 230a and foot 222a, it will be understood that track guides 230b-d and feet 222b-d can have similar or identical configurations. Additionally, track guides 230a-d and tracks 232a-d may also have other configurations than those illustrated. For instance, track guides may be formed on feet 222 while tracks are formed on foot portion 220. Furthermore, while track guides 230 are illustrated as being generally straight, track guides may also be curved so long as they cause feet 222 to move radially as feet 222 move longitudinally.

As can be seen in FIG. 20B, foot 222a does not extend substantially beyond the outer diameter of elongate member 206 when foot 222a is in the delivery position. As a result, foot 222a is in a relatively compact position and is able to be readily inserted through a puncture site and into a body lumen. In contrast, foot 222a extends radially beyond the outer diameter of elongate member 206 when foot 222a is in the deployed position (as shown in phantom lines in FIG. 20B). Device 200 can be configured so that feet 222a-d, when in the deployed position, extend out radially far enough that feet 222a-d can engage or be positioned adjacent to an interior or distal surface of a body lumen wall.

Returning again to FIG. 20A, feet 222a-d include cuff receptacles 238a-d. Cuffs 240a-d are releasably disposed within cuff receptacles 238a-d, respectively. Sutures 242, 244 are connected between pairs of cuffs 240a-d. In the illustrated embodiment, suture 242 is connected between cuffs 240a, 240c, while suture 244 is connected between cuffs 240b, 240d. When sutures 242, 244 are used to close a puncture site, sutures 242, 244 will form a generally X-shaped suture loop pattern. Nevertheless, sutures 242, 244 may be connected between cuffs 240a-d in such an arrangement so as to form other suture loop patterns. For instance, suture 242 could be connected between cuff 240a and cuff 240d and suture 244 could be connected between cuff 240b and cuff 240c. In such a case, sutures 242, 244 would create two generally parallel suture loops around a puncture site, similar to those shown in FIG. 17A.

Figure 21:
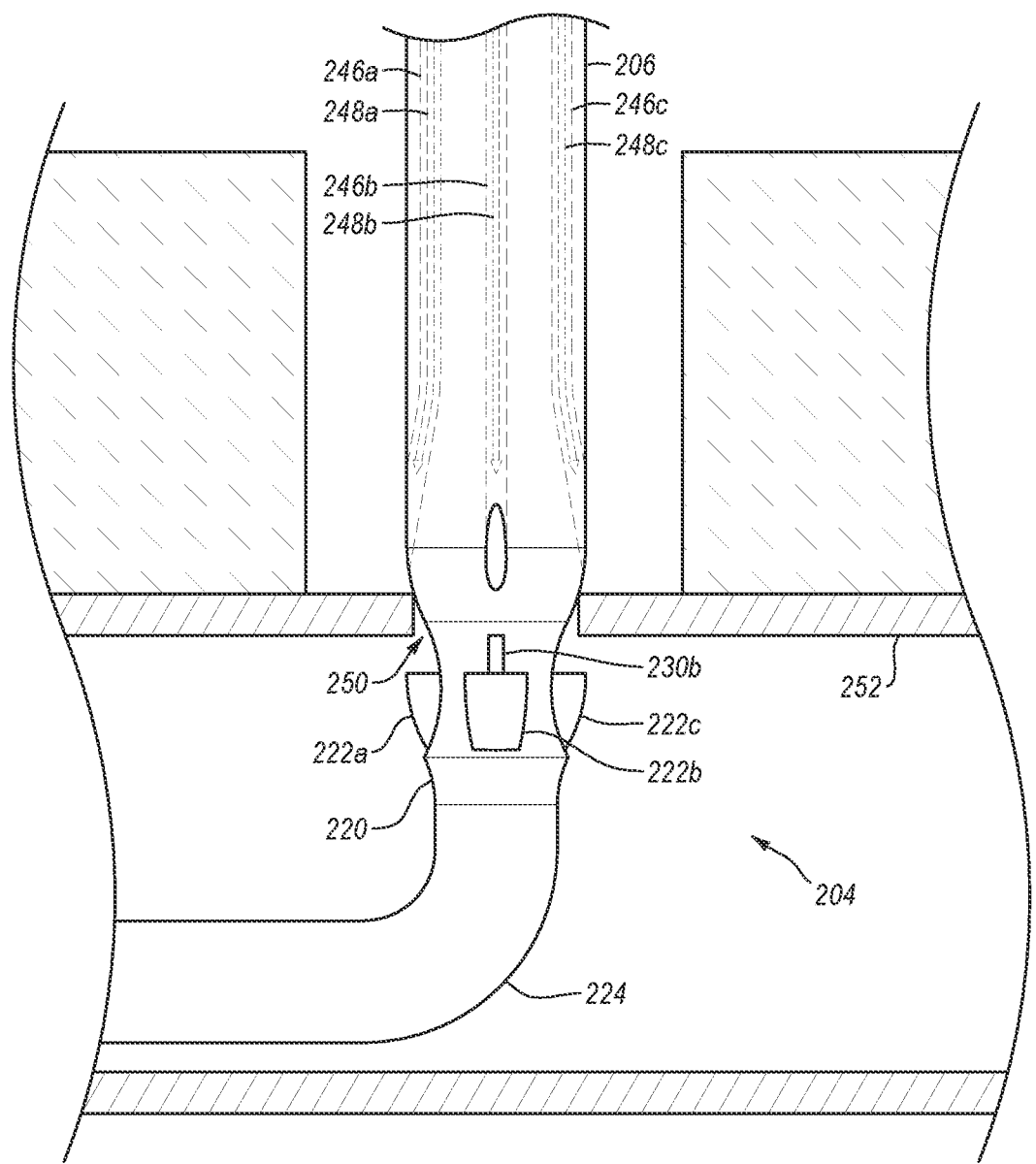
FIG. 21 is a close-up view of the distal end of the closure device of FIG. 18 inserted into a vessel through a puncture site.
Figure 22:
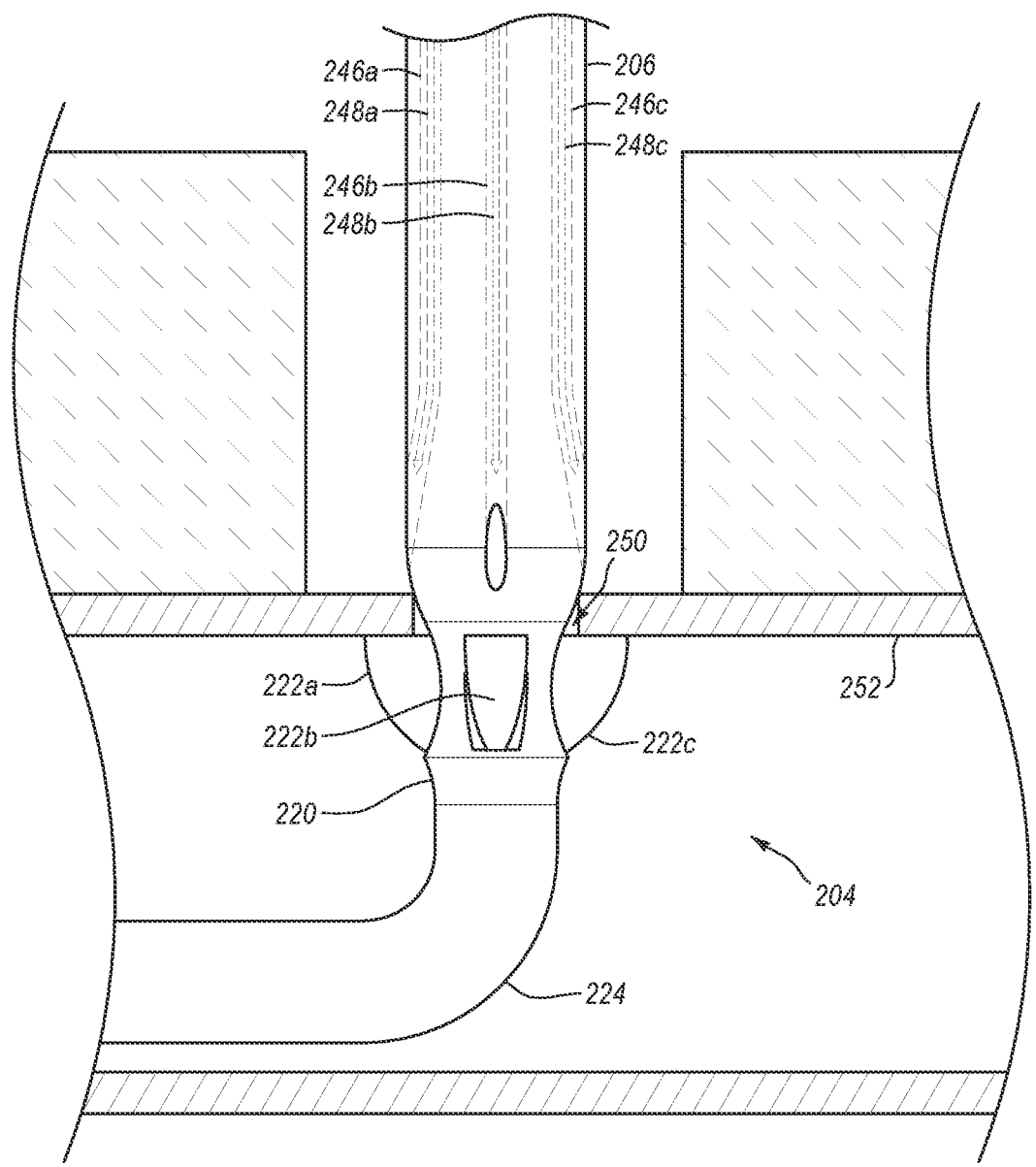
FIG. 22 is a view similar to FIG. 21, except that the foot lobes of the distal end have been deployed within the vessel.

As can be seen in FIGS. 19 and 21, feet 222a-d are generally aligned with needle lumens 246a-d in elongate member 206 when feet 222a-d are in the deployed position. As noted above, needles 248a-d may be passed through or extended from needle lumens 246a-d. Aligning feet 222a-d with needle lumens 246a-d enables needles 248a-d to be extended from needle lumens 246a-d toward cuffs 240a-d so that needles 248a-d may engage cuffs 240a-d.

Needles 248a-d can be advanced through needle lumens 246a-d using plunger 216. More specifically, plunger 216 may be linked to or operably associated with needles 248a-d such that needles 248a-d advance out of needle lumens 246a-d as plunger 216 is moved distally (i.e., towards distal end 204). Likewise, plunger 216 may be adapted to withdraw needles 248a-d back into needle lumens 246a-d when plunger 216 is moved proximally (i.e., away from distal end 204).

When feet 222a-d are in the deployed position within a body lumen, needles 248a-d can be deployed from elongate member 206 into the patient. As needles 248a-d penetrate the lumen wall, each needle 222a-d engages and connects to a cuff 240a-d in a manner similar to that described above in connection with needles 142 and cuffs 132. Once needles 248a-d are connected to cuffs 240a-d, needles 248a-d and connected cuffs 240a-d are withdrawn out of the patient. Drawing cuffs 240a-d out of the patient pulls sutures 242, 244 through the lumen wall so that sutures 242, 244 may be tied to close a puncture in the lumen wall.

As with device 100, device 200 may have a corresponding number of cuffs, needles, and needle lumens as discussed above. Also, like device 100, device 200 may also include non-corresponding numbers of cuffs, needles, and needle lumens. For instance, device 200 may include one or more needles that have multiple needle tips configured to retrieve or withdraw through a lumen wall more than one cuff as described herein.

With reference to FIGS. 21-25, one exemplary method of using device 200 will be discussed. In light of the foregoing discussion, it will be understood that device 200, as used in the following method, may include a plurality of individual needles (e.g., needles 248) delivered through individual needle lumens (e.g., 246), or may include one or more multi-tip needles (similar to needles 154) delivered through one or more needle lumens (similar to needle lumens 160). For simplicity, the following exemplary method will be described with reference to needles 248 and needle lumens 246. Nevertheless, it will be appreciated that needles 248 may be representative of two or more individual-tip or multi-tip needles. Likewise, needle lumens 246 may also be representative of two or more needle lumens through which individual-tip or multi-tip needles can be advanced As shown in FIG. 21, distal end 204 of device 200 is at least partially inserted into a patient such that foot portion 220 passes at least partially through a puncture 250 in a lumen wall 252. As with many translumninal procedures, device 200 may be introduced into the body lumen using a guidewire. Once foot portion 220 is positioned within the body lumen, feet 222a-d are moved from the delivery position shown in FIG. 21 to the deployed position shown in FIG. 22. As discussed above, feet 222a-d may be moved to the deployed position by actuating lever 218. Once feet 222a-d are in the deployed position, device 200 may be moved proximally so that feet 222a-d engage the interior surface of lumen wall 252. In this manner, feet 222a-d may be used as locators to ensure proper placement of distal end 204 within the body lumen.

Figure 23:
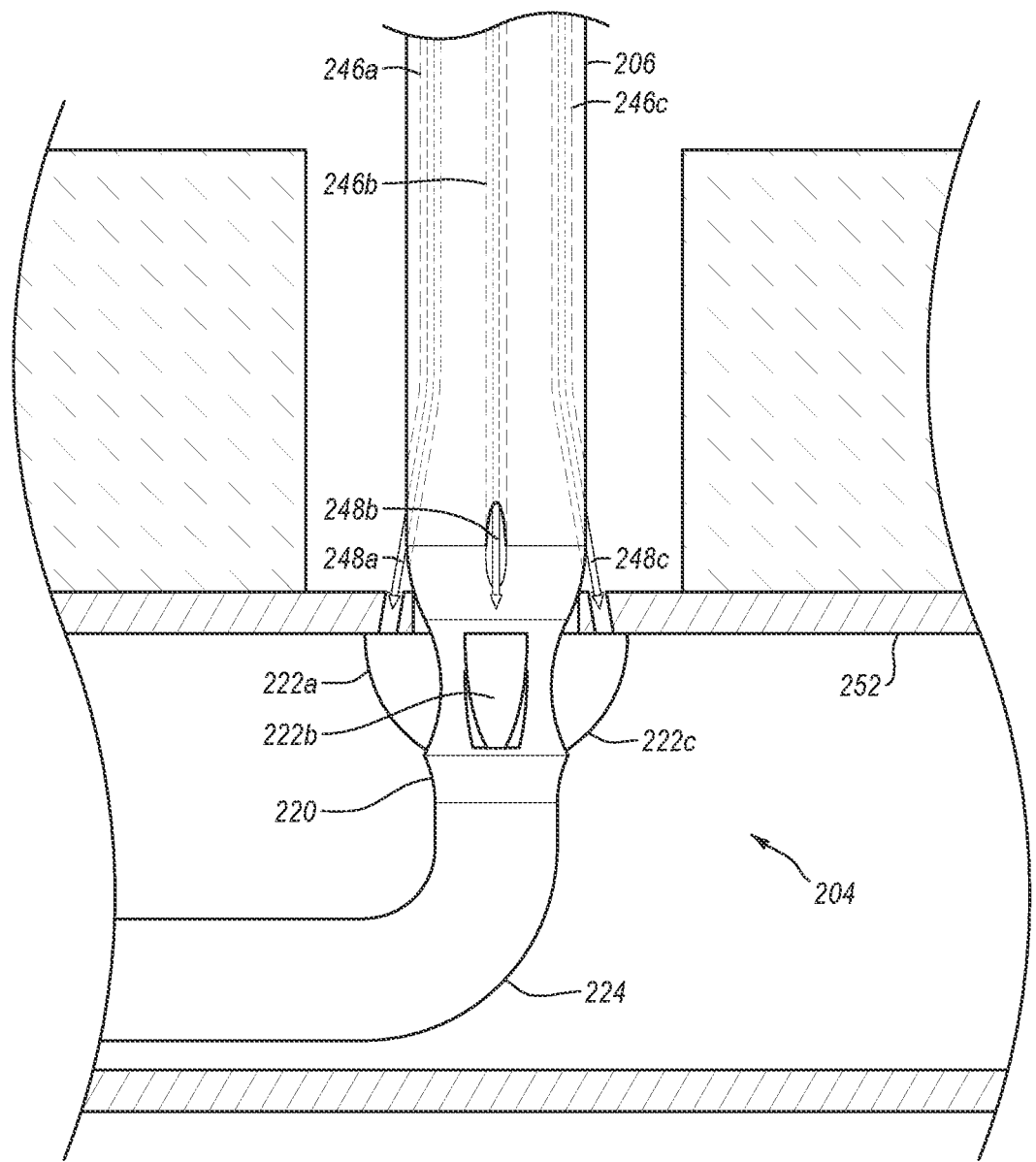
FIG. 23 is a view similar to FIG. 22, except that needles have been deployed partially through the vessel wall toward the cuffs mounted in the foot lobes.

Once feet 222a-d have been deployed and positioned within the body lumen as desired, needles 248a-d are advanced from needle lumens 246a-d as shown in FIG. 23. As discussed above, needles 248a-d may be advanced out of needle lumens 246a-d by moving plunger 216 (FIG. 1) distally. The advancement of needles 248a-d out of needle lumens 246a-d causes needles 248a-d to extend distally and at least partially radially away from elongate member 206. More specifically, as shown in FIG. 23, needles 248a-d extend out of needle lumens 246a-d at an angle relative to elongate member 206 so that needles 248a-d pass through lumen wall 252 and toward cuffs 240a-d in feet 222a-d as needles 248a-d advance out of needle lumens 246a-d.

Figure 24:
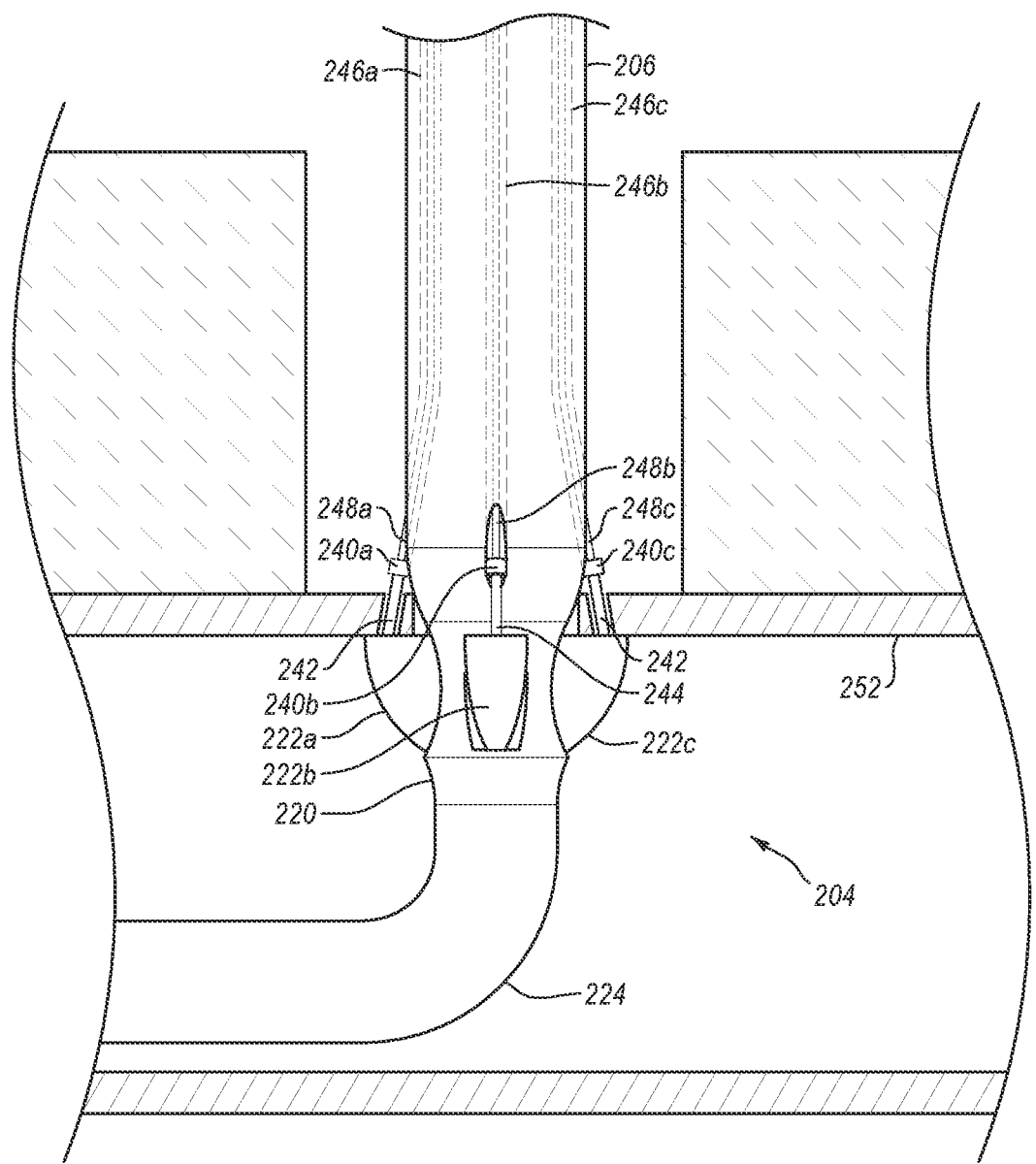
FIG. 24 is a view similar to FIG. 23, except that the needles have been drawn proximally after engaging the cuffs, thereby drawing the cuffs and attached sutures through the vessel wall.

As needles 248a-d engage cuffs 240a-d in feet 222a-d, the needle tips of needles 248a-d (whether single tip or multi-tip needles) securely engage cuffs 240a-d to connect cuffs 240a-d to needles 248a-d. With the needle tips securely connected to cuffs 240a-d, needles 248a-d are withdrawn out of the patient by moving plunger 216 (FIG. 1) proximally. As needles 248a-d are withdrawn, cuffs 240a-d are also withdrawn out of the patient. More specifically, since cuffs 240a-d are securely connected to needles 248a-d, withdrawal of needles 248a-d also causes cuffs 240a-d to be withdrawn. Even more specifically, as shown in FIG. 24, as needles 248a-d are drawn back through lumen wall 252, cuffs 240a-d are likewise drawn therethrough. As can also be seen in FIG. 24, since sutures 242, 244 are connected between cuffs 240a-d, the ends of suture 242, 244 are also drawn through lumen wall 252. As a result, the opposing ends of each suture 242, 244 extend through lumen wall 252 on opposing sides of puncture site 250 so that each suture 242, 244 spans puncture site 250.

Figure 25:
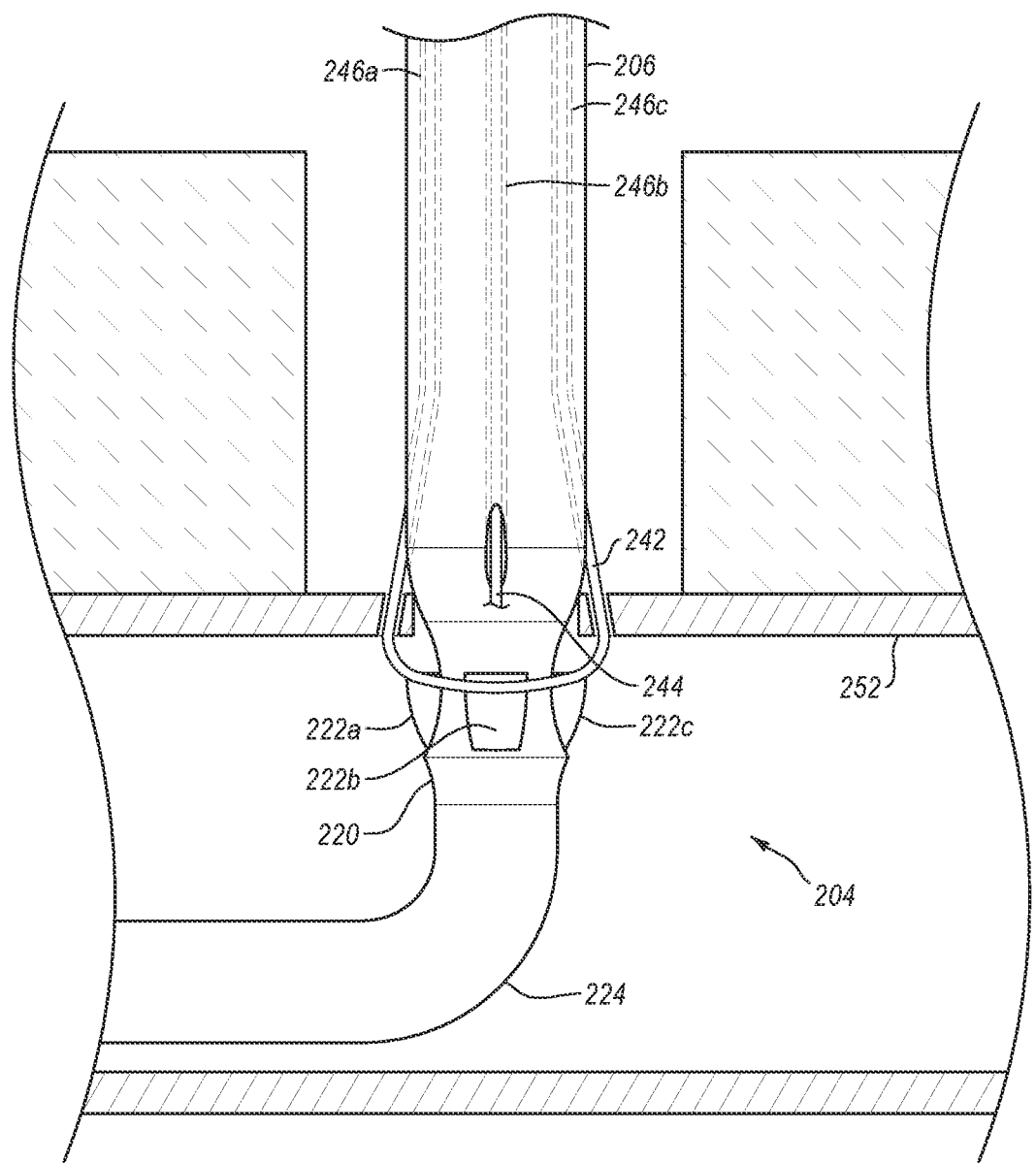
FIG. 25 illustrates the needles completely withdrawn into the elongate member and the foot lobes withdrawn back into the delivery position prior to removal of the distal end from the vessel.

Needles 248a-d may be withdrawn completely back into needle lumens 246a-d along with cuffs 240a-d as shown in FIG. 25. Feet 222a-d are then moved back to the delivery position as also shown in FIG. 25. As discussed above, feet 222a-d are moved from the deployed position to the delivery position by moving lever 218 from the position shown in FIG. 19 to the position shown in FIG. 18. Once feet 222a-d are in the delivery position, distal end 204 is removed from the patient, leaving sutures 242, 244 spanning puncture site 250 and extending out of lumen wall 252. Sutures 242, 244 are then secured to close puncture 250 as shown in FIGS. 17-17C. Sutures 242, 244 can be secured in any suitable manner, including by tying or with clamps, clips, or other closure devices.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. It shall be further understood that although the present invention has been described in relation to vessel closure, it is contemplated that the closure component of the present invention may be utilized to close other openings in the body such as PFO openings, or openings formed in organs such as the stomach for certain surgical procedures.

What is claimed is:

1. A method for closing an opening in tissue, comprising: positioning a first elongate member at least partially within a patient; and moving a needle assembly in relation to the first elongate member and within a first lumen of the first elongate member to locate a plurality of sutures, which are selectively mounted to the needle assembly, within the first lumen of the first elongate member, the needle assembly comprising a needle base, and a plurality of needle portions internally formed with and extending from the needle base, the plurality of needle portions comprising a first needle portion, a second portion, and a third needle portion, wherein when viewed in a direction transverse to a longitudinal axis of the first elongate member the second needle portion is disposed between the first needle portion and the second third needle portion and the first needle portion and the third need portion are arranged toward a periphery of the needle base.

2. The method of claim 1, wherein the needle portions and the needle base each have a generally circular cross-sectional shape.

3. The method of claim 1, wherein one of the needle portions is offset from another needle portion of the plurality of needle portions.

4. The method of claim 1, wherein the needle assembly frictionally engages with a plurality of suture carriers, each of the suture carriers having one of the plurality of sutures attached thereto.

5. The method of claim 1, further comprising moving a plunger operatively associated with needle assembly to slidably move the needle assembly.

6. A method for closing an opening in tissue, comprising:
positioning a first elongate member at least partially within a patient;
positioning a needle capture assembly in relation to the opening, the needle capture assembly comprising a plurality of tapered surfaces each configured to engage a needle; and
advancing a needle assembly comprising a needle base and a plurality of needle portions extending from the needle base in relation to the first elongate member and the needle capture assembly, to locate a plurality of sutures, which are selectively mounted to the needle assembly, within a first lumen of the first elongate member and mount each needle portion of the needle assembly into the needle capture assembly, the needle base being generally cylindrical with the plurality of needle portions being integral with and extending from an end of the needle base, at least three of the plurality of needle portions being disposed circumferentially around the needle base.

7. The method for closing the opening in tissue as recited in claim 6, further comprising withdrawing the plurality of sutures through tissue adjacent to the opening.

8. The method for closing the opening in tissue as recited in claim 7, wherein the needle assembly is detachably coupled to a plunger configured to move within the first elongate member.

9. The method for closing the opening in tissue as recited in claim 6, wherein the needle base has a generally rectangular cross-sectional shape.

10. The method for closing the opening in tissue as recited in claim 6, wherein the needle base has a generally V-shaped cross-sectional shape.

11. The method for closing the opening in tissue as recited in claim 6, wherein the needle assembly is configured to cooperate with a suture carrier having the plurality of sutures extending therefrom.

12. A method for closing an opening in tissue, comprising:
positioning a first elongate member at least partially within a patient;
positioning a needle capture assembly in relation to the opening, the needle capture assembly comprising a plurality of tapered surfaces; and
advancing a needle assembly, comprising a needle base and a plurality of needles each with a needle tip, in relation to the first elongate member and the needle capture assembly to locate a plurality of sutures, which are selectively mounted to the needle assembly, within a first lumen of the first elongate member and mount each needle tip of the needle assembly into engagement with a tapered surface of the plurality of tapered surfaces of the needle capture assembly, the needle base being generally cylindrical with the plurality of needle portions extending from an end of the needle base, a semi-circular region of the end of the needle base comprising three of the plurality of needles disposed circumferentially around the semi-circular region of the needle base.

13. The method for closing the opening in tissue as recited in claim 12, wherein advancing the needle assembly further comprises advancing the needle base towards the needle capture assembly to frictionally fit each needle tip to the tapered surface of the needle assembly.

14. The method for closing the opening in tissue as recited in claim 13, further comprising retracting the needle assembly from the needle capture assembly.

15. The method for closing the opening in tissue as recited in claim 14, further comprising withdrawing the plurality of sutures through tissue adjacent to the opening.

16. The method for closing the opening in tissue as recited in claim 14, further comprising withdrawing each needle tip through a tissue tract adjacent the opening in tissue.

17. The method for closing the opening in tissue as recited in claim 16, further comprising closing the opening in tissue by forming at least one knot using the plurality of sutures.

\* \* \* \* \*